United States Patent
Christensen et al.

(10) Patent No.: US 10,604,766 B2
(45) Date of Patent: Mar. 31, 2020

(54) DROUGHT AND HEAT TOLERANCE IN PLANTS

(71) Applicant: Ceres, Inc., Thousand Oaks, CA (US)

(72) Inventors: Cory Christensen, Shorewood, OR (US); Wuyi Wang, Newbury Park, CA (US); Dennis Yang, Ballwin, MO (US)

(73) Assignee: CERES, INC., Thousand Oaks, CA (US)

( * ) Notice: Subject to any disclaimer, the term of this patent is extended or adjusted under 35 U.S.C. 154(b) by 0 days.

(21) Appl. No.: 13/785,345

(22) Filed: Mar. 5, 2013

(65) Prior Publication Data

US 2013/0174298 A1 Jul. 4, 2013

Related U.S. Application Data

(60) Division of application No. 12/856,204, filed on Aug. 13, 2010, now abandoned, which is a continuation of application No. PCT/US2009/034068, filed on Feb. 13, 2009.

(60) Provisional application No. 61/029,048, filed on Feb. 15, 2008.

(51) Int. Cl.
   *C12N 15/82* (2006.01)

(52) U.S. Cl.
   CPC ................. *C12N 15/8273* (2013.01)

(58) Field of Classification Search
   None
   See application file for complete search history.

(56) References Cited

U.S. PATENT DOCUMENTS

| 5,538,880 | A | 7/1996 | Lundquist et al. |
| 5,766,847 | A | 6/1998 | Jackle et al. |
| 5,878,215 | A | 3/1999 | Kling et al. |
| 6,013,863 | A | 1/2000 | Lundquist et al. |
| 6,455,253 | B1 | 9/2002 | Patten et al. |
| 6,906,244 | B2 | 6/2005 | Fischer et al. |
| 7,173,121 | B2 | 2/2007 | Fang |
| 7,179,904 | B2 | 2/2007 | Kwok |
| 7,214,789 | B2 | 5/2007 | Pennell |
| 7,312,376 | B2 | 12/2007 | Apuya et al. |

(Continued)

FOREIGN PATENT DOCUMENTS

| EP | 0 534 858 | 3/1993 |
| EP | 1 033 405 | 9/2000 |

(Continued)

OTHER PUBLICATIONS

Vij et al. Genome wide analysis of the stress associated protein (SAP) gene family containing A20/AN1 zinc-finger(s) in rice and their phylogenetic relationship with *Arabidopsis*. Molecular Genetics and Genomics. 2006. 276: 565-575.*

(Continued)

*Primary Examiner* — Ashley K Buran
(74) *Attorney, Agent, or Firm* — Dentons US LLP

(57) ABSTRACT

Methods and materials for modulating heat and/or drought tolerance in plants are disclosed. For example, nucleic acids encoding heat and/or drought-tolerance polypeptides are disclosed as well as methods for using such nucleic acids to transform plant cells. Also disclosed are plants having increased heat and/or drought tolerance and plant products produced from plants having increased heat and/or drought tolerance.

13 Claims, 30 Drawing Sheets

Specification includes a Sequence Listing.

```
SEQ-ID-NO-1201   MAQRDKK--EE PTELRAPE-H T------LCAN NCGFPGNPAT QNLCQSCFSA  43
SEQ-ID-NO-1207   MAQRDKKVEE PTELRAPE-L T------LCAN SCGFPGNPAT NNLCQACFQA  44
SEQ-ID-NO-1195   MAQRTEK--E ETEFKVPETL T------LCVN NCGVTGNPAT NNMCQKCFSA  43
SEQ-ID-NO-749    MAQRTEK--E ETEFKVLETL TTTTTTLCTN NCGVTANPAT NNMCQKCFNA  48

SEQ-ID-NO-1201   ATASMSSSPT S--SSSSTA PAPA------ PPQPRPAPAE LASPADAAVA  86
SEQ-ID-NO-1207   ATASSASASV SPPSPSSSLS PSPAVFKFDE QQHARPSATA -VFADRPAEQ  93
SEQ-ID-NO-1195   TTAATSSSSS S--SSTNNTA TSATD------ DKSSRSTPTR -SQDNRSDSA  85
SEQ-ID-NO-749    SLVSAAAGVV E----SGSFL ---------- KRSARSVNLR -SSPAKVVLR  83

SEQ-ID-NO-1201   APAPEAAKAP ART------- ---------- -SANRCSSCR KRVGLTGFRC 118
SEQ-ID-NO-1207   PPAPASARPI RTTS------ ------TSSS SSVNRCQSCR KRVGLTGFRC 131
SEQ-ID-NO-1195   PPTTAATTAT ATTNSPMTAS NRSGYDTAEK KSVNRCSGCR KRVGLTGFRC 135
SEQ-ID-NO-749    PREI DAMKKR DQQ------- ---------- -IVNRCSGCR KKVGLTGFRC 115

SEQ-ID-NO-1201   RCGELFCGAH RYSDRHQCSY DYKQAARDAI ARENPVVRAA KIVRF  163
SEQ-ID-NO-1207   RCGELFCGAH RYSDRHDCQF DYKAVGRDAI ARENPVVRAA KIVRF  176
SEQ-ID-NO-1195   RCGELFCSDH RYSDRHDCSY DYKAAGREAI ARENPVVKAA KIIRV  180
SEQ-ID-NO-749    RCGELFCSEH RYSDRHDCSY DYKTAGREAI ARENPVVKAA KMVKV  160
```

(56) References Cited

U.S. PATENT DOCUMENTS

| | | |
|---|---|---|
| 7,378,571 B2 | 5/2008 | Apuya |
| 7,385,105 B2 | 6/2008 | Medrano et al. |
| 7,389,805 B2 | 6/2008 | Kakutani et al. |
| 7,402,667 B2 | 7/2008 | Cook et al. |
| 7,429,692 B2 | 9/2008 | Dang |
| 7,598,367 B2 | 10/2009 | Cook et al. |
| 7,838,650 B2 | 11/2010 | Pennell et al. |
| 7,851,608 B2 | 12/2010 | Cook et al. |
| 8,232,380 B2 | 7/2012 | Kwok et al. |
| 8,278,434 B2 | 10/2012 | Cook et al. |
| 2003/0009784 A1 | 1/2003 | Lebel et al. |
| 2005/0032221 A1 | 2/2005 | Chang et al. |
| 2005/0086718 A1 | 4/2005 | Heard et al. |
| 2006/0015970 A1 | 1/2006 | Pennell et al. |
| 2006/0021083 A1 | 1/2006 | Cook et al. |
| 2006/0041952 A1 | 2/2006 | Cook |
| 2006/0260004 A1 | 11/2006 | Fang et al. |
| 2007/0006335 A1 | 1/2007 | Cook et al. |
| 2007/0042387 A1 | 2/2007 | Pennell et al. |
| 2007/0056058 A1 | 3/2007 | Olivier et al. |
| 2007/0056688 A1 | 3/2007 | Kim et al. |
| 2007/0136839 A1 | 6/2007 | Cook et al. |
| 2007/0214517 A1 | 9/2007 | Alexandrov et al. |
| 2008/0235823 A1 | 9/2008 | Medrano et al. |
| 2009/0106866 A1 | 4/2009 | Lu et al. |
| 2009/0181851 A1 | 7/2009 | Cook et al. |
| 2010/0037346 A1 | 2/2010 | Cook et al. |
| 2010/0223692 A1* | 9/2010 | Shirley ............... C07K 14/415 800/278 |
| 2010/0269222 A1 | 10/2010 | Medrano et al. |
| 2011/0016587 A1 | 1/2011 | Cook et al. |
| 2011/0023193 A1 | 1/2011 | Christensen et al. |
| 2011/0041219 A1 | 2/2011 | Cook et al. |
| 2011/0167514 A1* | 7/2011 | Brover et al. .............. 800/278 |
| 2011/0252501 A1* | 10/2011 | Abad ............... C12N 15/8261 800/275 |
| 2013/0031668 A1* | 1/2013 | Brover et al. .............. 800/282 |
| 2013/0117881 A1 | 5/2013 | Cook et al. |
| 2013/0117886 A1* | 5/2013 | Troukhan et al. ........... 800/285 |

FOREIGN PATENT DOCUMENTS

| | | | |
|---|---|---|---|
| EP | 1586645 A2 * | 10/2005 | ............ C12N 15/29 |
| WO | WO 05/002326 | 1/2005 | |
| WO | WO 05/011105 | 2/2005 | |
| WO | WO 05/023639 | 3/2005 | |
| WO | WO 05/034343 | 4/2005 | |
| WO | WO 2005/098007 | 10/2005 | |
| WO | WO 2006/005023 | 1/2006 | |
| WO | WO 2006/034479 | 3/2006 | |
| WO | WO 06/038236 | 4/2006 | |
| WO | WO 06/040572 | 4/2006 | |
| WO | WO 2006/036864 | 4/2006 | |
| WO | WO 2006/066193 | 6/2006 | |
| WO | WO 2007/044988 | 4/2007 | |
| WO | WO 07/049275 | 5/2007 | |
| WO | WO 2007/055826 | 5/2007 | |
| WO | WO 2007/127501 | 11/2007 | |
| WO | WO 2007/120989 | 7/2009 | |

OTHER PUBLICATIONS

Mukhopadhyay et al. Overexpression of a zinc-finger protein gene from rice confers tolerance to cold, dehydration, and salt stress in transgenic tobacco. PNAS. 2004. 101(16): 6309-6314.*
GenBank Accession No. Q9LHJ8. Zinc finger A20 and AN1 domain-containing stress associated protein 5 (AtSAP5). Published Jan. 9, 2007. pp. 1-3.*
U.S. Appl. No. 60/505,689, filed Sep. 23, 2003, Cook et al.
U.S. Appl. No. 60/518,075, filed Nov. 6, 2003, Pennell et al.
U.S. Appl. No. 60/544,771, filed Feb. 13, 2004, Cook et al.
U.S. Appl. No. 60/558,869, filed Apr. 1, 2004, Cook et al.
U.S. Appl. No. 60/583,609, filed Jun. 30, 2004, Alexandrov.
U.S. Appl. No. 60/583,691, filed Jun. 30, 2004, Alexandrov et al.
U.S. Appl. No. 60/612,891, filed Sep. 23, 2004, Kwok.
U.S. Appl. No. 60/637,140, filed Dec. 16, 2004, Feldmann.
U.S. Appl. No. 60/757,544, filed Jan. 9, 2006, Dang.
U.S. Appl. No. 60/776,307, filed Feb. 24, 2006, Kwok.
Authorized Officer J. Krüger, Supplementary European Search Report, Application No. EP 09710460.8, dated Oct. 11, 2011, 9 pages.
Authorized Officer C. H. Lee. International Search Report & Written Opinion, PCT/US2009/034068, dated Sep. 25, 2009, 13 pages.
Authorized officer Simin Baharlou, International Preliminary Report on Patentability from PCT/US2009/034068, dated Aug. 17, 2010, 7 pages.
Abler et al. "Isolation and characterization of a genomic sequence encoding the maize Cat3 catalase gene" Plant Mol. Biol., 22:1031-1038 (1993).
Alonso-Blanco et al., "The use of recombinant inbred lines (RILs) for genetic mapping," In Methods in Molecular Biology (J.M. Martinez-Zapater and J. Salinas, Humana Press, Totowa, NJ., 1998), 82: 137-146.
Baerson et al., "Developmental regulation of an acyl carrier protein gene promoter in vegetative and reproductive tissues" Plant Mol. Biol., 22(2):255-267 (1993).
Bateman et al., "Pfam 3.1: 1313 multiple alignments and profile HMMs match the majority of proteins" Nucl. Acids Res., 27(1):260-262 (1999).
Bechtold et al., "In planta Agrobacterium mediated gene transfer by infiltration of adult *Arabidopsis thaliana* plants" C.R. Acad. Sci. Paris, 316:1194-1199 (1993).
Berry & Bjorkman, "Photosynthetic response and adaptation to temperature in higher plants," Ann. Rev. Plant Physiol., 1980, 31: 491-543.
Braga et al., "Expression of the Cry1Ab protein in genetically modified sugarcane for the control of diatraea saccharalis," Journal of New Seeds, 2003, 5: 209-221.
Burr et al., "Gene mapping with recombinant inbreds in maize," Genetics, 1988, 118: 519-526.
Burr et al., "Mapping Genes with Recombinant Inbreds," In Freeling and Walbot (Ed.), The Maize Handbook, (New York, Springer-Verlag, 1994), pp. 249-254.
Bustos et al., "Regulation of b-glucuronidase expression in transgenic tobacco plants by an A/T-rich, cis-acting sequence found upstream of a French bean b-phaseolin gene" Plant Cell, 1(9):839-854 (1989).
Cerdan et al., "A 146 bp fragment of the tobacco Lhcb1*2 promoter confers very-low-fluence, low-fluence and high-irradiance responses of phytochrom to a minimal CaMV 35S promoter" Plant Mol. Biol., 33:245-255 (1997).
Cheikh and Jones, "Disruption of maize kernel growth and development by heat stress," Plant Physiol, 1994, 106: 45-51.
Chen et al., "Functional analysis of regulatory elements in a plant embryo-specific gene" Proc. Natl. Acad. Sci. USA, 83:8560-8564 (1986).
Chenna et al., "Multiple sequence alignment with the Clustal series of programs" Nucleic Acids Res., 31(13):3497-3500 (2003).
Conkling et al. "Isolation of transcriptionally regulated root-specific genes from tobacco" Plant Physiol., 93:1203-1211, (1990).
Dai et al., "RF2b, a rice bZIP transcription activator, interacts with RF2a and is involved in symptom development of rice tungro disease" Proc. Natl. Acad. Sci. USA, 101(2):687-692 (2004).
Database Accession No. Q9LHJ8, Oct. 2000, 2 pages.
Durbin et al., "3-Markov chains and hidden Markov models; 4-Pairwise alignment using HMMS; 5-Profile HMMs for sequence families" In Biological Sequence Analysis: Probabilistic Models of Proteins and Nucleic Acids, (Cambridge University Press, Cambridge, UK, 1998), pp. 47-134.
Fejes et al., "A 268 bp upstream sequence mediates the circadian clock-regulated transcription of the wheat Cab-1 gene in transgenic plants" Plant Mol. Biol., 15:921-932 (1990).
Fromm et al., "An octopine synthase enhancer element directs tissue-specific expression and binds ASF-1, a factor from tobacco nuclear extracts" The Plant Cell, 1:977-984 (1989).

(56) References Cited

OTHER PUBLICATIONS

GenBank Accession No. AF096096, dated Jan. 25, 1999, 2 pages.
GenBank Accession No. AF129516, dated Apr. 6, 1999, 2 pages.
GenBank Accession No. L05934, dated Oct. 22, 1993, 3 pages.
GenBank Accession No. U93215, dated Feb. 27, 2002, 42 pages.
Green et al., "Binding site requirements for pea nuclear protein factor GT-1 correlate with sequences required for light-dependent transcriptional activation of the rbcS-3A gene" EMBO J., 7:4035-4044 (1988).
Hong et al., "Promoter sequences from two different *Brassica napus* tapetal oleosin-like genes direct tapetal expression of ß-glucuronidase in transgenic *Brassica* plants" Plant Mol Biol., 1997 34(3):549-555.
Hwang et al, "Aleurone- and embryo-specific expression of the ß-glucuronidase gene controlled by the barley Chi26 and Ltp1 promoters in transgenic rice" Plant Cell Rep. 20(7):647-654 (2001).
Jang et al., "Expression of a bifunctional fusion of the *Escherichia coli* genes for trehalose-6-phosphate synthase and trehalose-6-phosphate phosphatase in transgenic rice plants increases trehalose accumulation and abiotic stress tolerance without stunting growth," Plant Physiology, 2003, 131: 516-524.
Jordano et al., "A sunflower helianthinin gene upstream sequence ensemble contains an enhancer and sites of nuclear protein interaction" Plant Cell, 1:855-866 (1989).
Kang et al., "*Arabidopsis* SAP5 functions as a positive regulator of stress responses and exhibits E3 ubiquitin ligase activity," Plant Mol. Biol., 2011, 75: 451-466.
Kasuga et al., "Improving plant drought, salt, and freezing tolerance by gene transfer of a single stress-inducible transcription factor," Nature Biotech, 1999, 17: 287-291.
Keller and Baumgartner, "Vascular-specific expression of the bean GRP 1.8 gene is negatively regulated" Plant Cell, 3(10):1051-1061 (1991).
Lam et al., "Site-specific mutations in alter in vitro factor binding and change promoter expression pattern in transgenic plants" Proc. Natl. Acad. Sci. USA, 86:7890-7894 (1989).
Luan et al., "A rice cab gene promoter contains separate cis-acting elements that regulate expression in dicot and monocot plants" The Plant Cell, 4:971-981 (1992).
Lubberstedt et al., "Promoters from genes for plastid proteins possess regions with different sensitivities toward red and blue light" Plant Physiol., 104:997-1006 (1994).
Maestri et al., "Molecular genetics of heat tolerance and heat shock proteins in cereals," Plant Mol. Biol., 2002, 48; 667-681.
Matsuoka et al., "Tissue-specific light-regulated expression directed by the promoter of a C4 gene, maize pyruvate, orthophosphate dikinase, in a C3 plant, rice" Proc. Natl. Acad. Sci. USA, 90:9586-9590 (1993).
Medberry et al., "The Commelina yellow mottle virus promoter is a strong promoter in vascular and reproductive tissues" Plant Cell, 4(2):185-192 (1992).
Meier et al., "Elicitor-inducible and constitutive in vivo DNA footprints indicate novel cis-acting elements in the promoter of a parsley gene encoding pathogenesis-related protein 1" Plant Cell, 3:309-316 (1991).
Refseth et al., "Hybridization capture of microsatellites directly from genomic DNA" Electrophoresis, 18:1519-1523 (1997).
Riggs et al., "Cotyledon nuclear proteins bind to DNA fragments harboring regulatory elements of phytohemagglutinin genes" Plant Cell, 1(6):609-621 (1989).
Rivera et al, "Genomic evidence for two functionally distinct gene classes" Proc. Natl. Acad. Sci. USA ,95:6239-6244 (1998).
Sheridan, "The mac1 Gene: Controlling the commitment to the meiotic pathway in Maize" Genetics, 142:1009-1020 (1996).
Slocombe et al., "Temporal and tissue-specific regulation of a *Brassica napus* stearoyl-acyl carrier protein desaturase gene" Plant Physiol., 104(4):1167-1176 (1994).
Sonnhammer et al., "Pfam: A comprehensive database of protein domain families based on seed alignments" Proteins, 28:405-420 (1997).

Sonnhammer et al., "Pfam: multiple sequence alignments and HMM-profiles of protein domains" Nucl. Acids Res., 26:320-322 (1998).
Suh et al., "Structural features required for the interaction of the Hsp70 molecular chaperone DnaK with its cochaperone DnaJ," *J Biol. Chem.*, 1999, 274(43):30534-30539.
Truernit et al., "The promoter of the *Arabidopsis thaliana* SUC2 sucrose-H+ symporter gene directs expression of ß-glucuronidase to the phloem: Evidence for phloem loading and unloading by SUC2" Planta. 196:564-570 (1995).
Urao et al. "Molecular cloning and characterization of a gene that encodes a MYC-related protein in *Arabidopsis*" Plant Mol. Biol., 32:571-576 (1996).
Vij and Tyagi, "Genome-wide analysis of the stress associated protein (SAP) gene family containing A20/AN1 zinc-finger(s) in rice and their phylogenetic relationship with *Arabidopsis*," Mol. Gen. Genomics, 2006, 276: 565-575.
Vogel et al., "Trehalose-6-phosphate phosphatases from *Arabidopsis thaliana*: identification by functional complementation of the yeast tps2 mutant," The Plant Journal, 1998, 13(5): 673-683.
Yamamoto et al., "The promoter of a pine photosynthetic gene allows expression of a ßglucuronidase reporter gene in transgenic rice plants in a light-independent but tissue-specific manner" Plant Cell Physiol., 1994, 35:773-778.
Zhang et al., "DNA sequences that activate isocitrate lyase gene expression during late embryogenesis and during postgerminative growth," Plant Physiology, 110:1069-1079 (1996).
Zheng et al., "SPK1 Is an Essential S-Phase-Specific Gene of *Saccharomyces cerevisiae* that encodes a nuclear serine/threonine/tyrosine kinase" Mol. Cell Biol., 1993, 13:5829-5842.
'Turf Screen' [online]. "Impact of Turf Screen on Drought Tolerance & Recovery of Turf," May 29, 2014, [retrieved on Jun. 18, 2014]. Retrieved from the Internet: URL http://turfscreen.com/blog/impact-of-turf-screen-on-drought-tolerance-recovery-of-turf/, 2 pages.
Day et al., "Transgene integration into the same chromosome location can produce alleles that express at a predictable level, or alleles that are differentially silenced," Genes Development, 2000, 14:2869-2880.
Frost et al., "The Tonoplast-Localized Sucrose Transporter in Populus (PtaSUT4) Regulates Whole-Plant Water Relations, Responses to Water Stress, and Photosynthesis," PLos ONE, 2012, 7(8):e44467, 10 pages.
Harb et al., "Molecular and Physiological Analysis of Drought Stress in *Arabidopsis* Reveals Early Responses Leading to Acclimation in Plant Growth," Plant Physiol., Nov. 2010, 154:1254-1271.
Hignight et al., "Turfgrass Water Conservation Protocol," Turfgrass Water Conservation Alliance, Retrieved on Jun. 18, 2014, 9 pages.
Industry News, "TWCA hosts AASCO seed control officials," Lawn & Landscape: Market Leadership, Sep. 9, 2010, 2 pages.
NTEP, "Drought Tolerance Testing of Cool-Season Grasses," NTEP Drought Tolerance Draft Proposal, Apr. 21, 2009, 2 pages.
Poudel, "Testing of Clonal Bermuda grass Cultivars and Experimental Genotypes for Differences in Drought Performance," Thesis, Oklahoma State Univ., Dec. 2010, 102 pages.
Unknown, "Zinc finger A20 and AN1 domain-containing stress-associated protein 5", Uniprot Accession No. Q9LHJ8, http://www.uniprot.org/uniprot/Q9LHJ8, Oct. 1, 2000.
Vij et al., "Genome-wide analysis of the stress associated protein (SAP) gene family containing A20/AN1 zinc-finger(s) in rice and their phylogenetic relationship with *Arabidopsis*," *Mol. Genet Genomics* 276(6):565-575, 2006.
Mukhopadhyay et al., "Overexpression of a zinc-finger protein gene from rice confers tolerance to cold, dehydration, and salt stress in transgenic tobacco," *Proc. Nat'l. Acad. Sci. USA* 101(16):6309-6314, 2004.
GenPept Accession No. NP_566429.1, dated Mar. 20, 2017.
Alfonso et al., "Unusual tolerance to high temperatures in a new herbicide-resistant D1 mutant from *Glycine max* (L.) Merr. cell cultures deficient in fatty acid desaturation," *Planta* 212:573-582, 2001.
Cho et al., "Constitutive expression of abiotic stress-inducible hot pepper CaXTH3, which encodes a xyloglucan endotransglucosylase/

(56) References Cited

OTHER PUBLICATIONS hydrolase homolog, improves drought and salt tolerance in transgenic *Arabidopsis* plants," *FEBS Letters* 580:3136-3144 2006.
Clarke et al., "Salicylic acid dependent signaling promotes basal thermotolerance but is not essential for acquired thermotolerance in *Arabidopsis thaliana*," *The Plant Journal* 38:432-447, 2004.

* cited by examiner

```
SEQ ID NO:584   MRK---VLV------AVLIVSMVAS|HFENVA|------------GPGDCYDGCS|TACVQRDPRK   22
SEQ ID NO:568   MMKKQVTIVA----ALLIMMALCS|SLNMVAEAQL------------------------------   50
SEQ ID NO:578   MKK---MVVA----MMLIFLLIST|QMESVE|----------------------------------   23

SEQ ID NO:584   ------------------SDAS----------GSGVSEQIDN|XMMKKQVTIV|AALLILVALS   26
SEQ ID NO:568   TSRCDRKCSI|RCGPDAARAS|-------------------------------------------   100
SEQ ID NO:578   ------------------PDAA----------------------------------------   27

SEQ ID NO:584   ----------|DCMDAC|--------|TTCVQSNTR|LTSRCDLKCG|RCGPDSEVEI|        62
SEQ ID NO:568   SNLDMVAEAQ|LGPGD|CYDGC|STACVQRDSR|KTSRCDRKCSI|RCGPDAKKA|         150
SEQ ID NO:578   ----------|DCLDGC|--------|TTACVQSDSR|LQARCDRKCSI|RCGPDSTIK|       63

SEQ ID NO:584   DHTFG--        66
SEQ ID NO:568   GETGA--        155
SEQ ID NO:578   EDMG---        67
```

|  |  |  |  |  |  |  |
|---|---|---|---|---|---|---|
| SEQ ID NO:682 | | | | | | 348 |
| SEQ ID NO:674 | | | | | | 332 |
| SEQ ID NO:634 | | | | | | 337 |
| SEQ ID NO:590 | YSSLPESI KK | SNCREVYIYR | NPFNVVASWF | | | 359 |
| SEQ ID NO:623 | | | | HFSNVEGEPE | KLDEEYF | 410 |
| SEQ ID NO:632 | | | | | | 348 |
| SEQ ID NO:627 | | | | | | 344 |

Figure 4 (continued)

| | | | | | | |
|---|---|---|---|---|---|---|
| SEQ ID NO:707 | MASNKVSFFL | VLCLCI L LAG | ECI ESPI FTG | NKCSDPT GMD | KDGKCLD YCH | 50 |
| SEQ ID NO:705 | MASNKVSFFL | VLCLCVLSTA | EFGEAQI LTG | IKCPDPNGHD | KEDKCN YCL | 50 |
| SEQ ID NO:706 | MASNKVSFF F | LFL CVLSTA | EFGEAQNPRG | RKCEDPNGVD | QKAKCY YCN | 50 |

| | | | | |
|---|---|---|---|---|
| SEQ ID NO:707 | AQGYP GGSCI | GFI DQGYMCV | CK VG | 74 |
| SEQ ID NO:705 | NQN Y MGGSCQ | GYKNH-YMCE | CYVG | 73 |
| SEQ ID NO:706 | EQGFLGGSCQ | GYT NH-YMCE | CYVG | 73 |

| SEQ_ID_NO:999 | SDRHGCSYDY | KSAARDAIAR | DNPVVRAAKI | VRF | 170 |
| --- | --- | --- | --- | --- | --- |
| SEQ_ID_NO:759 | SDRHDCSFDY | KAAGRESIAR | QNPVVKAAKI | IRL | 170 |
| SEQ_ID_NO:1215 | TDRHDCSYDY | KTVGREAIAK | ENPVVKAAKI | VKV | 137 |
| SEQ_ID_NO:799 | ADKHACTFDF | KKSDREKIAK | ENPLIVAPKI | TKF | 224 |
| SEQ_ID_NO:1010 | AEKHACDFDF | KAAGREKIAK | NNPLVVAAKI | | 193 |
| SEQ_ID_NO:857 | PEKHECSFDF | KFVGRGAIAK | ANPVVKADKV | | 175 |
| SEQ_ID_NO:796 | PGTTCLCLDL | | | | 137 |
| SEQ_ID_NO:801 | PEQHDCEFDF | KSLGKEQIAK | ANPVVKGEKL | QRI | 159 |
| SEQ_ID_NO:892 | PEQHGCGFDF | KGMGREEIAK | ANPVVKGEKL | NKI | 170 |
| SEQ_ID_NO:859 | PEKHACGFDF | KAVGREEIAR | ANPVIKGEKL | RRI | 164 |
| SEQ_ID_NO:763 | PENHGCTFDF | KKVGREEIAK | ANPLVKAEKL | EKI | 161 |
| SEQ_ID_NO:742 | PEVHGCTFDF | KSAGREEIAK | ANPLVIAAKL | QKI | 161 |
| SEQ_ID_NO:912 | PEVHGCTFDY | KKVAREQIAK | ANPLVVAAKL | QKI | 160 |
| SEQ_ID_NO:955 | TDSHQCTFDY | KKVAREQIAK | QNPVVMAEKI | NKI | 163 |
| SEQ_ID_NO:1000 | TDSHECTFDY | HVAAQEAIAK | ANPVVIAEKI | NKI | 159 |
| SEQ_ID_NO:1306 | ADVHNCSFDY | RSAAQDAIAK | ANPVVKADKL | DKL | 168 |
| SEQ_ID_NO:798 | SDKHDCPFDY | HTAARDIAK | ANPVVKAEKL | EKI | 173 |
| SEQ_ID_NO:953 | SDKHDCPYDY | HTAARDVAK | ANPVVKADKL | DKL | 173 |
| SEQ_ID_NO:988 | SDKHDCQFDY | RTAARDAIAK | ANPVVKAEKL | EKI | 171 |
| SEQ_ID_NO:991 | SDKHDCQFDY | RTAARDAIAK | ANPVVKAEKL | DKI | 171 |

| | | | | | | |
|---|---|---|---|---|---|---|
| SEQ ID NO:933 | QGRKVFEIRP | MIEWDKGKAL | EFLLESLGFG | NSNNVEPVYI | GDDRTDEDAF | 314 |
| SEQ ID NO:1142 | NGRMVLEVRP | VIDWDKGKAV | EFLLQSLGLN | DSENVIPIYI | GDDRTDEDAF | 323 |
| SEQ ID NO:1146 | NGRMVLEVRP | VIDWDKGKAV | EFLLOSLGLN | DSENVIPIYI | GDDRTDEDAF | 320 |
| SEQ ID NO:1140 | NGRMVLEVRP | VIDWDKGKAV | EFLLRSLGLN | DSEDVVPIYI | GDDRTDEDAF | 321 |
| SEQ ID NO:1144 | HGRKVLEVRP | VIDWDKGKAV | EFLLESLGLN | ESDDVLPIYI | GDDKTDEDAF | 333 |
| SEQ ID NO:926 | HGRKVLEVRP | VIDWNKGKAV | EFLLESLGLS | DRDDVLPIYV | GDDRTDEDAF | 337 |
| SEQ ID NO:1129 | HGRKVLEVRP | VIDWDKGKAV | TFLLESLGL- | NCEDVLPIYV | GDDRTDEDAF | 336 |
| SEQ ID NO:1148 | HGRKVLEVRP | VIDWDKGKAV | TFLLESLGL- | NCDDVLAYV | GDDRTDEDAF | 332 |
| SEQ ID NO:1150 | HGRKVLEIRP | ANWDKGKAL | EFLLESLGLDLS | NCDDVLPIYV | GDDRTDEDAF | 338 |
| SEQ ID NO:1182 | HGRKVLEVRP | VLNWDKGKAV | EFLLESLGLK | NCDDVLPIYV | GDDRTDEDAF | 333 |

| | | | | | | |
|---|---|---|---|---|---|---|
| SEQ ID NO:933 | KLLRDR-GEG | CGVLVSKFPK | DTDASTYLQD | PSEASDEFLA | TIGGVEITNA | 363 |
| SEQ ID NO:1142 | KVLRQR-NCG | YGILVSQVPK | ETEAFYSLRD | PSEV-MEFLN | FLVRWKKHSV | 371 |
| SEQ ID NO:1146 | KVLRKR-NCG | YGILVSQVPK | DTEAFYSLRD | PSEV-MAFLN | SLVRWKKHSL | 368 |
| SEQ ID NO:1140 | KVLRER-SCG | YGILVSSVPK | DTEAFYSLRD | PSEV-MGFLN | SLVRWKKHPL | 369 |
| SEQ ID NO:1144 | KVLKAN-NHG | FGILVSSVPK | DSDAFYSLRD | PSEV-MEFLR | TLAWKEGSS | 381 |
| SEQ ID NO:926 | KVLKEC-NMG | YGILVSSVPK | ESNAFSVRD | PSEV-KKFLK | ALVRWKRLEE | 386 |
| SEQ ID NO:1129 | KVLRDCPNHG | YGILVSAVPK | DSNAFYSLRD | PSEV-MEFLK | SLVTWKRSMG | 385 |
| SEQ ID NO:1148 | KVLKEA-NKG | YGILVSRAPK | ESNAYYSLRD | PSEV-MEFLT | SLAEWKSSLQ | 382 |
| SEQ ID NO:1150 | KVLRER-NCG | CGILVSKSPK | ESSAFYSLRD | PAEV-MEFLK | SLVTWKKSSA | 387 |
| SEQ ID NO:1182 | KVLREC-NKG | YGILVSAPK | ESSAFYSLRD | PSEV-MEFLK | CLVSWKKSSC | 384 |

| | |
|---|---|
| SEQ ID NO:933 | KSVKRMYV 371 |
| SEQ ID NO:1142 | -------- 371 |
| SEQ ID NO:1146 | -------- 368 |
| SEQ ID NO:1140 | -------- 369 |
| SEQ ID NO:1144 | A------- 381 |
| SEQ ID NO:926 | -------- 386 |
| SEQ ID NO:1129 | AR------ 385 |
| SEQ ID NO:1148 | L------- 382 |
| SEQ ID NO:1150 | FSY----- 387 |
| SEQ ID NO:1182 | -------- 384 |

Figure 9 (continued)

| SEQ ID NO | | | | | | |
|---|---|---|---|---|---|---|
| SEQ ID NO:74 | MYATLPSPFL | PKSLHAFSPN | KTSSSLRTSA | RAASFKSATA | TEGNS----- | 45 |
| SEQ ID NO:60 | -------MAGTL | VNSAGRFSPG | NCILPQQRTA | RFYSGTARFP | TGAPSFKAS- | 44 |
| SEQ ID NO:915 | -------MAGTL | VNSAGRFSPG | NCILPQQRTA | RFYSGTARFP | TGAPSFKAS- | 44 |
| SEQ ID NO:62 | -----MSGTLYS | AVNSLRSSPG | NS-LRQPKPT | RLHNGNAREP | TGATSFRASA | 47 |
| SEQ ID NO:152 | -----MSGTLYL | GVINSLRSSPG | NS-LRQPKPT | RLHNGNARLS | TGATSFRASA | 47 |
| SEQ ID NO:98 | ------MLSSLPTS | NSLLS----- | SI-SPPSA | SRIRFRPPLA | AASTAYFTSK | 41 |
| SEQ ID NO:102 | ---MSPRPAM | SPSFLAFRPG | SP-AASPPPS | PRLNGPPPLS | ASFSA---- | 42 |
| SEQ ID NO:104 | --------MA-FS | SSSSPCFFP- | ---SHNLTNL | RYNKHNSPM | SASFA---- | 35 |

| SEQ ID NO | | | | | | |
|---|---|---|---|---|---|---|
| SEQ ID NO:74 | AQTLNAEPAV | --AAVALAGS | LYEILRVERT | ASLNEIKTAY | RSLAKVYHPD | 83 |
| SEQ ID NO:60 | AQTLNAEPAV | TESVRRRVSS | LYELLKVNET | ASLTEIKTAY | RSLAKVVYHPD | 94 |
| SEQ ID NO:915 | AQTLNAEPAV | TESVRRRVSS | LYELLKVNET | ASLTEIKTAY | RSLAKVVYHPD | 94 |
| SEQ ID NO:62 | AQTLNAEPAV | TESVRRRASS | LYELLRVDET | ASLTEIKTAY | RSLAKVHHPD | 97 |
| SEQ ID NO:152 | AQTLNAEPAV | TESVRRRASN | LYELLRVDEI | ASLTEIKTAY | RSLAKVHHPD | 97 |
| SEQ ID NO:98 | QQKASPSGYL | SRPGMACTS | LYEVLGLSVG | ASNQEIKAAY | RRLARVCHPD | 91 |
| SEQ ID NO:102 | ---STAVTA | PDHAAJASS | FMDVLGLRPG | ASPREIKTAY | RRLALAVHPD | 88 |
| SEQ ID NO:104 | --TSERPGT | ARSTRATPSS | LYEVLGLQIG | ADTMEIKSAY | RRLARVMHPD | 82 |

| SEQ ID NO | | | | | | |
|---|---|---|---|---|---|---|
| SEQ ID NO:74 | A--------- | GRDFIEIRNA | YATLSDPTAR | AVYDMSLGVR | ---ARRIR-- | 125 |
| SEQ ID NO:60 | A--------- | GRDFMEIHKA | YATLADPTTR | AIYDSTLRVP | --RRRVHAGA | 137 |
| SEQ ID NO:915 | A--------- | GRDFMEIHKA | YATLADPTTR | AIYDSTLRVP | --RRRVHAGA | 137 |
| SEQ ID NO:62 | A--------- | GRDFMEIHKA | YATLADPTTR | AIYDSTLGAR | --GRRMHAGA | 141 |
| SEQ ID NO:152 | A--------- | ADEFMKIHAA | YATLADPTTR | AIYDSTLGAR | --GRRVHAGA | 141 |
| SEQ ID NO:98 | VTIDRKDSS | AEDFIRVHAA | YSTLSDPDKR | AVYDMSKL-W | ---RCQR-- | 134 |
| SEQ ID NO:102 | AP-HPASSS | AEDFMKVHSA | YSTLSDPDKR | ADYDRLLS | AGRRRAHPA- | 137 |
| SEQ ID NO:104 | V--GNLNSS | ADEFMKVHSA | YATLSDPGKR | ADYDRSLFV | ---RPEM-- | 122 |

| SEQ ID NO | | | |
|---|---|---|---|
| SEQ ID NO:74 | --TRVYP-- | ---RRWETDQ | CW | 140 |
| SEQ ID NO:60 | MGRSGRVYA- | TTRRWETDQ | CW | 157 |
| SEQ ID NO:915 | MGRSGRVYA- | TTRRWETDQ | CW | 157 |
| SEQ ID NO:62 | TGRTSRVYP- | TTRRWETDQ | CW | 161 |
| SEQ ID NO:152 | MGRTSRVYP- | TTRRWETDQ | CW | 161 |
| SEQ ID NO:98 | PLTSASMFSG | YTGRSWETDQ | CW | 156 |
| SEQ ID NO:102 | LGRSPSFPAR | RSRRTWETDQ | CW | 159 |
| SEQ ID NO:104 | VGRSCS-PVG | YSGRRWETDQ | CW | 143 |

| SEQ ID NO | | | | | | |
|---|---|---|---|---|---|---|
| SEQ ID NO:408 | QKRRLTMTP- | | | | | 235 |
| SEQ ID NO:364 | RKRRLTSTP- | | | | | 250 |
| SEQ ID NO:407 | RKRRLTASP- | | | | | 247 |
| SEQ ID NO:421 | RRLKQDGIAE | TTEQATPPDG | QIVKYQPMMN | ETAKAMLRKI | MKWDTPRVES | 287 |
| SEQ ID NO:410 | RRRPI-DNTP- | | | | | 253 |
| SEQ ID NO:413 | RRRPI-DNMP- | | | | | 249 |
| SEQ ID NO:408 | ---------- | ---------- | ---------- | ---------- | ---------- | 250 |
| SEQ ID NO:364 | ---------- | SVTG | SDQPM-NYSS | SL- | ---------- | 262 |
| SEQ ID NO:407 | ---------- | SLGT | MEENL- | ---HD- | ---------- | 270 |
| SEQ ID NO:421 | FNKNPDNYLI | GDCTSPSSAM | LQEVASVALG | SSQFVDYMN- | SVQSTQIPMS | 337 |
| SEQ ID NO:410 | -------FY | SDG------- | DSSSSTSWNS | GVTLQEVPPS | ---------- | 280 |
| SEQ ID NO:413 | -------FY | -EISEQ | LDSQDKMFES | GV-LNGLNE- | GI-------- | 281 |
| | | DPGETSQTEQ | LDSPY-LFDS | CV-LNELSEP | | |
| SEQ ID NO:408 | ---------- | ---------- | ---------- | ---------- | ---------- | 250 |
| SEQ ID NO:364 | ---------- | ---------- | ---------- | ---------- | ---------- | 262 |
| SEQ ID NO:407 | ---------- | ---------- | ---------- | ---------- | ---------- | 270 |
| SEQ ID NO:421 | TGTQGHIPSA | EKPEILSVPQ | AAASANVMKD | GTHAASTIPT | SQADVIMPDI | 387 |
| SEQ ID NO:410 | ---------- | ---------- | ---------- | ---------- | ---------- | 280 |
| SEQ ID NO:413 | ---------- | ---------- | ---------- | ---------- | ---------- | 281 |
| SEQ ID NO:408 | ---------- | ---------- | QESEAELAS- | EMLFSAAMD | NESSSNVRPD | 279 |
| SEQ ID NO:364 | ---------- | ---------- | QEFDRMKDD | MEMLFAAAID | DEANNSM--- | 288 |
| SEQ ID NO:407 | ---------- | ---------- | QDLPTIENE- | METLFSAVLD | NESSSDIKDP | 299 |
| SEQ ID NO:421 | PSVPEIVPKS | ILDIPEDNYM | APETDDGFMD | PSSLGSLPDD | ---LDC---- | 430 |
| SEQ ID NO:410 | ---------- | ---------- | PELENLAVN- | QELGKGSID | ---DGN---- | 302 |
| SEQ ID NO:413 | ---------- | ---------- | PELENLAVN- | QDLGKGKVD | ---EER---- | 303 |
| SEQ ID NO:408 | SV-------- | GTDMEPVADD | WEELLSEDL | ISGDRAAEEV | VVVEQPEFD | 324 |
| SEQ ID NO:364 | ---PTKE-- | EQCLEAMNVM | MRDGNL | ---EAAID- | ---------- | 313 |
| SEQ ID NO:407 | IASSMDTASG | GSTLDAVNET | WEELLTDDL | VSGE--PNEV | VVSDEPEVD- | 346 |
| SEQ ID NO:421 | ---LSPG--- | ADIDDLSNS | WDDLLQTPL | PEDF------ | ---EANLDE- | 464 |
| SEQ ID NO:410 | ---LTQV--- | SDQSE-LNDD | FMAELLVEDF | GDKA------ | GQPELE---- | 335 |
| SEQ ID NO:413 | ---QNQT--- | NCQAE-LGDD | FMAELLVEDF | TGKE------ | EQSELD---- | 336 |

| SEQ ID NO | Sequence | Position |
|---|---|---|
| SEQ-ID-NO:282 | VVLLYLLISA FCCGLSLPSC RS | 221 |
| SEQ-ID-NO:256 | LVIVYIALFF VCHGFTLPTC R | 221 |
| SEQ-ID-NO:268 | LVIIYVVLVF VCHGFTLPTC R | 221 |
| SEQ-ID-NO:294 | TMIYVVLMF MCHGFTLPTC L | 221 |
| SEQ-ID-NO:160 | LVIYIAVAF LCHGPTLPSC F | 219 |
| SEQ-ID-NO:242 | LVIVYVVLAF VCHGPALPSC F | 219 |
| SEQ-ID-NO:253 | VIAYVVLAF VCHGPALPTC F | 219 |
| SEQ-ID-NO:162 | LIIYVVLAF VCHGITLPTC K | 220 |
| SEQ-ID-NO:184 | LVIYVVLAF VCHGLTLPTC LK | 220 |

| | | | | | |
|---|---|---|---|---|---|
| SEQ ID NO: 1201 | MAQRDKK--EE | PTELRAPEL- | ---------- | ---------- | NCGFPGNPAT | QNLCQSCFSA | 43 |
| SEQ ID NO: 1207 | MAQRDKKVEE- | PTELRAPEL- | ---------- | T--------- | SCGFPGNPAT | NNLCQACFQA | 44 |
| SEQ ID NO: 1195 | MAQRTEK---- | ETEFKVPETL | ---------- | T--------- | NCGVTGNPAT | NNMCQKCFSA | 43 |
| SEQ ID NO: 749  | MAQRTEK---E | ETEFKVLETL | ---------- | TTTTTLCTN- | NCGVTANPAT | NNMCQKCFNA | 48 |

| SEQ ID NO: 1201 | ATASMSSSPI- | S--SSSSTA- | ---------- | PAPAA----- | PPQPRPAPAE | LASPADAAVA | 86 |
| SEQ ID NO: 1207 | ATASSSASV-- | SPPSPSSSLS | ---------- | PSPAVFKFDE | QQHARPSATA | -VFADRPAEQ | 93 |
| SEQ ID NO: 1195 | TTAATSSSSS- | S--SSTNNTA | ---------- | TSATD----- | DKSSRSTPTR | -SQDNRSDSA | 85 |
| SEQ ID NO: 749  | SLVSAAAGVM- | E--SGSIL-- | ---------- | ---------- | KRSARSVNLR | -SSPAKVVLR | 83 |

| SEQ ID NO: 1201 | APAPEAAKAP  | ARIT------ | ---------- | ---------- | -SANRCSSCR | KRVGLTGFRC | 118 |
| SEQ ID NO: 1207 | PPAPASARPI  | RITTS----- | ---------- | ---------- | SSVNRCSGCR | KRVGLTGFRC | 131 |
| SEQ ID NO: 1195 | PPITAATTAT  | ATTNSPMTAS | NRSGYDIAEK | TSSS------ | KSVNRCSGCR | KIVGLTGFRC | 135 |
| SEQ ID NO: 749  | PREIDAVKKR  | DQQ------- | ---------- | ---------- | VNRCSGCR   | KKVGLTGFRC | 115 |

| SEQ ID NO: 1201 | RCGELFCGAH | RYSDRHGCSY | DYKCAARDAI | ARENPVVRAA | KIVRF | 163 |
| SEQ ID NO: 1207 | RCGELFCGAH | RYSDRHDCCF | DYKAVGRDAI | ARENPVVRAA | KIVRF | 176 |
| SEQ ID NO: 1195 | RCGELFCSDH | RYSDRHDCSY | DYKAAGREAI | ARENPVVKAA | KIIRV | 180 |
| SEQ ID NO: 749  | RCGELFCSEH | RYSDRHDCSY | DYKITAGREAI | ARENPVVKAA | KMVKV | 160 |

Figure 15

| | | | | | |
|---|---|---|---|---|---|
|SEQ_ID_NO:1360|MAL-QISKKR|KFVADGVFLA|ELNEMLTREL|GEDGFAGVEI|RVTPMRTEII 49|
|SEQ_ID_NO:1340|MAT-QISKKK|KFVSDGVFYA|ELNEMLTREL|AEDGYSGVEV|RVTPMRTEII 49|
|SEQ_ID_NO:1347|MAT-QISKKR|KFVSDGVFYA|ELNEVLTREL|AEDGYSGVEV|RVTPMRTEII 49|
|SEQ_ID_NO:1311|MAT-QISKKR|KFVADGVFYA|ELNEVLTREL|AEDGYSGVEV|RVTPMRTEII 49|
|SEQ_ID_NO:1313|MAT-QMSKKR|KFVADGVFYA|ELNEVLTREL|AEDGYSGVEV|RVTPMRTEII 49|
|SEQ_ID_NO:1353|MAT-QISKKR|KFVADGVFFA|ELNEVLTREL|AEDGYSGVEV|RVTPMRTEII 49|
|SEQ_ID_NO:1331|MATAQISKKR|KFVADGVFEA|ELNEVLTREL|AEDGYSGVEV|RVTPMRTEII 50|

| | | | | | |
|---|---|---|---|---|---|
|SEQ_ID_NO:1360|RATRTQNVL|GEKGRRIREL|TSVVQKRFNF|PDGGVELYAE|KVLNRGLCAV 99|
|SEQ_ID_NO:1340|RATRTQNVL|GEKGRRIREL|TSVVQKRFNF|PENGVELYAE|KVVNRGLCAI 99|
|SEQ_ID_NO:1347|RATRTQNVL|GEKGRRIREL|TSVVQKRFNF|PENGVELYAE|KVANRGLCAI 99|
|SEQ_ID_NO:1311|RATRTQNVL|GEKGRRIREL|TSLVQKRFKF|PQDSVELYAE|KVANRGLCAI 99|
|SEQ_ID_NO:1313|RATRTQNVL|GEKGRRIREL|TSLVQKRFRF|PQDSVELYAE|KVANRGLCAI 99|
|SEQ_ID_NO:1353|RATRTQAVL|GEKGRRIREL|TSVVQKRFKF|PENSVELYAE|KVNHRGLCAI 99|
|SEQ_ID_NO:1331|RATRTQNVL|GEKGRRIREL|TSVVQKRFKF|PENSVELYAE|KVNNRGLCAI 100|

| | | | | | |
|---|---|---|---|---|---|
|SEQ_ID_NO:1360|AQAESLRYKL|GGLAVRRAC|YGVLRFVMES|GAKGCEVIVS|GKLRAQRAKS 149|
|SEQ_ID_NO:1340|AQAESLRYKL|GGLAVRRAC|YGVLRFVMES|GAKGCEVIVS|GKLRAQRAKS 149|
|SEQ_ID_NO:1347|AQAESLRYKL|GGLAVRRAC|YGVLRFVMES|GAKGCEVIVS|GKLRAQRAKS 149|
|SEQ_ID_NO:1311|AQAESLRYKL|GGLAVRRAC|YGVLRYVMES|GAKGCEVIVS|GKLRAARAKS 149|
|SEQ_ID_NO:1313|AQAESLRYKL|GGLAVRRAC|YGVLRFVMES|GAKGCEVIVS|GKLRAARAKE 148|
|SEQ_ID_NO:1353|AQAESLRYKL|GGLAVRRMC|YGVLRFVMES|GAKGCEVIVS|GKLRAQRAKS 149|
|SEQ_ID_NO:1331|AQAESLRYKL|GGLAVRRAC|YGVLREIMES|GAKGCEVIVS|GKLRAQRAKS 150|

| | | | | | |
|---|---|---|---|---|---|
|SEQ_ID_NO:1360| | | | | 149|
|SEQ_ID_NO:1340|MKFKDGYMIS|SGQPVNEYID|AAVRHVLLRQ|GVLGIKVKIM|LDWDPK 195|
|SEQ_ID_NO:1347|MKFKDGYMIS|SGQPVNEYLD| | | 169|
|SEQ_ID_NO:1311|ML| | | | 148|
|SEQ_ID_NO:1313|MKFKDGYMIS|SGQPVKDYID|SAVRHVLLRQ|GVI| 150|
|SEQ_ID_NO:1353|MKFKDGYMIS|SGHPVNEYLD|SAVRHVLLRF| | 181|
|SEQ_ID_NO:1331| | | | | 179|

Figure 16

DROUGHT AND HEAT TOLERANCE IN PLANTS

CROSS-REFERENCE TO RELATED APPLICATIONS

This application is a divisional of U.S. application Ser. No. 12/856,204, filed on Aug. 13, 2010, which is a continuation of International Application No. PCT/US2009/034068, filed Feb. 13, 2009, which claims the benefit of U.S. Provisional Application No. 61/029,048, filed Feb. 15, 2008. The contents of all of the foregoing applications are hereby incorporated by reference in their entireties.

TECHNICAL FIELD

This document relates to methods and materials involved in modulating drought and/or heat tolerance in plants. For example, this document provides plants having increased drought and/or heat tolerance as well as materials and methods for making plants having increased drought and/or heat tolerance.

BACKGROUND

Due to their sessile nature, plants are constantly under the threat of temperature stress when they are subjected to a wide range of temperature variation in different habitats and climates during growing seasons and even diurnally. Most economically valuable plants, including those used in agriculture, horticulture, forestry, biomass for bioconversion, and other industries (e.g., the paper industry or pharmaceutical/chemical industries where plants are used as production factories for proteins or other compounds) are exposed to higher than optimal temperatures, or heat stress, during some stages of their life cycle from seed germination to seed maturation (Maestri et al. *Plant Mol. Biol.* 48:667-681 (2002)). Heat stress is one of the most common stresses in crop production. Under heat stress, plants can succumb to a variety of physiological and developmental damages, including dehydration due to increased transpiration, impairment of photosynthetic carbon assimilation, inhibition of translocation of assimilates, increased respiration, reduced organ size due to a decrease in the duration of developmental phases, disruption of seed development, and a reduction in fertility (Berry and Bjorkman, *Ann. Rev. Plant Physiol.* 31:491-543 (1980); Cheikh and Jones, *Plant Physiol.* 106: 45-51 (1994)). Thus, exposure to heat stress often results in reduced yield and overall decreased crop quality (Maestri et al. *Plant Mol. Biol.* 48:667-681 (2002)).

In the field, heat stress is often associated with other stresses, such as drought and high light, which presents even greater challenge to plants. Plants exposed to low water or drought conditions typically have low yields of plant material, seeds, fruit and other edible products. Some areas of the world consistently have very low rainfall and therefore have problems growing sufficient food crops for their population.

Thus, there is a need for methods of increasing drought and/or heat tolerance in plants.

SUMMARY

This document provides methods and materials related to plants having increased heat and/or drought tolerance. For example, this document provides transgenic plants and plant cells having increased heat and/or drought tolerance, nucleic acids used to generate transgenic plants and plant cells having increased heat and/or drought tolerance, and methods for making plants and plant cells having increased heat and/or drought tolerance. Such plants having increased heat and/or drought tolerance may be useful to produce biomass which may be converted to a liquid fuel or other chemicals and/or to produce crops with increased yield and/or quality.

Methods of producing a plant are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-16. The plant has a difference in drought tolerance or heat tolerance as compared to a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO: 2, 3, 4, 5, 6, 7, 8, 9, 10, 11, 13, 15, 17, 19, 21, 23, 25, 27, 29, 31, 33, 35, 37, 39, 41, 43, 45, 47, 49, 51, 53, 55, 57, 60, 62, 63, 64, 65, 66, 67, 68, 69, 70, 71, 73, 74, 76, 78, 80, 82, 84, 86, 88, 90, 92, 94, 96, 98, 100, 102, 104, 106, 108, 110, 112, 114, 116, 118, 120, 122, 124, 126, 127, 130, 132, 134, 136, 138, 139, 142, 144, 146, 148, 150, 152, 154, 156, 158, 160, 162, 164, 166, 168, 170, 172, 174, 176, 178, 179, 180, 182, 184, 186, 188, 190, 192, 194, 196, 198, 200, 202, 204, 206, 208, 209, 212, 214, 216, 218, 220, 222, 224, 225, 228, 229, 231, 233, 234, 235, 237, 239, 240, 242, 244, 246, 248, 250, 252, 253, 254, 256, 258, 260, 262, 264, 266, 268, 269, 271, 273, 275, 277, 279, 280, 282, 284, 286, 288, 289, 290, 291, 292, 293, 294, 295, 296, 297, 298, 299, 300, 301, 302, 303, 304, 305, 307, 309, 311, 312, 314, 315, 316, 317, 319, 320, 321, 322, 323, 325, 326, 327, 329, 330, 332, 334, 335, 336, 337, 338, 339, 340, 341, 343, 344, 346, 348, 349, 350, 351, 353, 355, 356, 358, 360, 362, 364, 366, 368, 369, 370, 371, 373, 375, 377, 379, 381, 383, 385, 387, 389, 390, 392, 394, 396, 398, 400, 401, 402, 404, 405, 407, 408, 410, 412, 413, 414, 416, 418, 419, 420, 421, 422, 423, 424, 426, 428, 430, 431, 432, 433, 434, 435, 436, 438, 440, 442, 443, 445, 447, 449, 451, 453, 455, 457, 459, 461, 463, 465, 467, 469, 470, 472, 474, 476, 478, 480, 481, 483, 485, 487, 489, 490, 491, 492, 494, 496, 498, 500, 502, 504, 506, 508, 510, 512, 514, 515, 516, 518, 519, 520, 522, 524, 526, 528, 530, 531, 533, 535, 536, 538, 540, 541, 543, 545, 547, 548, 550, 552, 553, 555, 557, 558, 559, 561, 562, 564, 566, 568, 569, 570, 572, 574, 576, 578, 580, 582, 584, 586, 588, 590, 591, 592, 593, 594, 595, 596, 597, 598, 599, 600, 602, 603, 604, 605, 607, 608, 610, 612, 614, 615, 616, 617, 618, 619, 620, 621, 623, 625, 627, 629, 631, 632, 634, 635, 636, 638, 640, 642, 644, 646, 647, 648, 650, 651, 653, 654, 655, 656, 658, 660, 661, 662, 663, 664, 665, 666, 667, 668, 669, 671, 673, 674, 675, 676, 678, 680, 682, 684, 685, 687, 688, 690, 691, 692, 694, 696, 698, 700, 702, 705, 706, 707, 708, 709, 711, 712, 714, 715, 717, 719, 721, 723, 725, 726, 727, 729, 731, 733, 734, 735, 737, 738, 740, 741, 742, 743, 744, 745, 746, 747, 748, 749, 751, 752, 753, 754, 755, 756, 757, 759, 760, 761, 763, 765, 767, 768, 769, 771, 773, 774, 775, 777, 779, 781, 783, 785, 787, 789, 791, 793, 795, 796, 797, 798, 799, 801, 803, 805, 807, 808, 809, 810, 811, 812, 813, 815, 816, 817, 819, 821, 823, 825, 827, 829, 832, 834, 836, 839, 840, 841, 842, 843, 844, 845, 846, 848, 849, 850, 851, 852, 853, 854, 856, 857, 859, 861, 863, 865, 867, 869, 870, 871, 872, 873, 874, 876, 878, 880, 882, 885, 886, 887, 888, 889, 890, 891, 892, 893, 894, 896, 897, 898, 900, 901, 902, 904, 906, 908, 910, 912, 913, 914, 915, 916, 918, 920, 922, 924, 926, 929, 931, 932, 933, 935, 937, 939, 941, 943, 944, 945, 947, 949, 951, 952, 953, 955, 957, 958, 959, 960, 961, 962, 963, 964, 966, 968, 969, 970, 971, 973, 974, 975, 977, 978, 979, 980, 981, 983, 985, 987, 988, 989, 990, 991, 992, 993, 995, 997, 998, 999, 1000, 1001, 1003, 1005, 1007, 1010, 1012, 1013, 1014, 1015, 1016, 1018, 1020, 1022, 1023, 1025, 1027, 1028, 1030, 1031, 1033, 1035, 1037, 1039, 1041, 1043, 1045, 1046, 1048, 1050, 1051, 1053, 1055, 1056, 1058, 1059, 1061, 1062, 1064, 1066, 1068, 1069, 1071, 1073, 1075, 1077, 1079, 1080, 1082, 1084, 1086, 1088, 1090, 1092, 1093, 1094, 1096, 1098, 1100, 1102, 1104, 1106, 1108, 1110, 1112, 1113, 1114, 1116, 1117, 1118, 1119, 1121, 1123, 1125, 1129, 1130, 1131, 1132, 1133, 1134, 1135, 1136, 1137, 1138, 1140, 1142, 1144, 1146, 1148, 1150, 1151, 1152, 1153, 1154, 1156, 1157, 1158, 1159, 1160, 1161, 1162, 1164, 1166, 1168, 1170, 1172, 1174, 1175, 1177, 1179, 1181, 1182, 1184, 1186, 1188, 1189, 1191, 1193, 1195, 1197, 1199, 1201, 1203, 1205, 1207, 1209, 1210, 1212, 1214, 1215, 1216, 1218, 1219, 1221, 1222, 1223, 1225, 1226, 1228, 1230, 1231, 1232, 1234, 1236, 1238, 1240, 1242, 1244, 1246, 1248, 1250, 1252, 1254, 1256, 1258, 1262, 1264, 1265, 1267, 1269, 1271, 1273, 1274, 1276, 1277, 1279, 1281, 1283, 1285, 1286, 1287, 1288, 1290, 1292, 1293, 1294, 1296, 1298, 1300, 1302, 1304, 1306, 1311, 1313, 1315, 1317, 1319, 1321, 1323, 1324, 1325, 1326, 1327, 1329, 1331, 1333, 1334, 1336, 1338, 1340, 1342, 1343, 1345, 1347, 1349, 1350, 1351, 1353, 1354, 1356, 1358, 1360, or 1361. A plant produced from the plant cell has a difference in drought tolerance or heat tolerance compared to a control plant that does not comprise the exogenous nucleic acid.

In another aspect, the polypeptide can comprise a sulfotransferase 1 domain having 70 percent or greater sequence identity to the sulfotransferase 1 domain of SEQ ID NO:590 or orthologs thereof such as those identified in the sequence listing; an AN1-like zinc finger domain having 70 percent or greater sequence identity to the AN1-like zinc finger domain of SEQ ID NO:742 or SEQ ID NO:749 or orthologs thereof such as those identified in the sequence listing and an A20-like zinc finger domain having 70 percent or greater sequence identity to the A20-like zinc finger domain of SEQ ID NO:742 or SEQ ID NO:749 or orthologs thereof such as those identified in the sequence listing; a short chain dehydrogenase domain having 70 percent or greater sequence identity to the short chain dehydrogenase domain of SEQ ID NO:1012 or orthologs thereof such as those identified in the sequence listing; a trehalose-phosphatase domain having 70 percent or greater sequence identity to the trehalose-phosphatase domain of or SEQ ID NO:1129 or orthologs thereof such as those identified in the sequence listing; a synaptobrevin-related polypeptide having 70 percent or greater sequence identity to the synaptobrevin-related polypeptide of SEQ ID NO:160 or orthologs thereof such as those identified in the sequence listing; an HSF-type DNA-binding domain having 70 percent or greater sequence identity to the HSF-type DNA-binding domain of SEQ ID NO:311 or SEQ ID NO:364 or orthologs thereof such as those identified in the sequence listing; a DnaJ domain having 70 percent or greater sequence identity to the DnaJ domain of SEQ ID NO:60 or orthologs thereof such as those identified in the sequence listing; or a KH_2 domain having 70 percent or greater sequence identity to the KH_2 domain of SEQ ID NO:1311 or orthologs thereof such as those identified in the sequence listing.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO: 1, 12, 14, 16, 18, 20, 22, 24, 26, 28, 30, 32, 34, 36, 38, 40, 42, 44, 46, 48, 50, 52, 54, 56, 58, 59, 61, 72, 75, 77, 79, 81, 83, 85, 87, 89, 91, 93, 95, 97, 99, 101, 103, 105, 107, 109, 111, 113, 115, 117, 119, 121, 123, 125, 128, 129, 131, 133, 135, 137, 140, 141, 143, 145, 147, 149, 151, 153, 155, 157, 159, 161, 163, 165, 167, 169, 171, 173, 175, 177, 181, 183, 185, 187, 189, 191, 193, 195, 197, 199, 201, 203, 205, 207, 210, 211, 213, 215, 217, 219, 221, 223, 226, 227, 230, 232, 236, 238, 241, 243, 245, 247, 249, 251, 255, 257, 259, 261, 263, 265, 267, 270, 272, 274, 276, 278, 281, 283, 285, 287, 306, 308, 310, 313, 318, 324, 328, 331, 333, 342, 345, 347, 352, 354, 357, 359, 361, 363, 365, 367, 372, 374, 376, 378, 380, 382, 384, 386, 388, 391, 393, 395, 397, 399, 403, 406, 409, 411, 415, 417, 425, 427, 429, 437, 439, 441, 444, 446, 448, 450, 452, 454, 456, 458, 460, 462, 464, 466, 468, 471, 473, 475, 477, 479, 482, 484, 486, 488, 493, 495, 497, 499, 501, 503, 505, 507, 509, 511, 513, 517, 521, 523, 525, 527, 529, 532, 534, 537, 539, 542, 544, 546, 549, 551, 554, 556, 560, 563, 565, 567, 571, 573, 575, 577, 579, 581, 583, 585, 587, 589, 601, 606, 609, 611, 613, 622, 624, 626, 628, 630, 633, 637, 639, 641, 643, 645, 649, 652, 657, 659, 670, 672, 677, 679, 681, 683, 686, 689, 693, 695, 697, 699, 701, 703, 704, 710, 713, 716, 718, 720, 722, 724, 728, 730, 732, 736, 739, 750, 758, 762, 764, 766, 770, 772, 776, 778, 780, 782, 784, 786, 788, 790, 792, 794, 800, 802, 804, 806, 814, 818, 820, 822, 824, 826, 828, 830, 831, 833, 835, 837, 838, 847, 855, 858, 860, 862, 864, 866, 868, 875, 877, 879, 881, 883, 884, 895, 899, 903, 905, 907, 909, 911, 917, 919, 921, 923, 925, 927, 928, 930, 934, 936, 938, 940, 942, 946, 948, 950, 954, 956, 965, 967, 972, 976, 982, 984, 986, 994, 996, 1002, 1004, 1006, 1008, 1009, 1011, 1017, 1019, 1021, 1024, 1026, 1029, 1032, 1034, 1036, 1038, 1040, 1042, 1044, 1047, 1049, 1052, 1054, 1057, 1060, 1063, 1065, 1067, 1070, 1072, 1074, 1076, 1078, 1081, 1083, 1085, 1087, 1089, 1091, 1095, 1097, 1099, 1101, 1103, 1105, 1107, 1109, 1111, 1115, 1120, 1122, 1124, 1126, 1127, 1128, 1139, 1141, 1143, 1145, 1147, 1149, 1155, 1163, 1165, 1167, 1169, 1171, 1173, 1176, 1178, 1180, 1183, 1185, 1187, 1190, 1192, 1194, 1196, 1198, 1200, 1202, 1204, 1206, 1208, 1211, 1213, 1217, 1220, 1224, 1227, 1229, 1233, 1235, 1237, 1239, 1241, 1243, 1245, 1247, 1249, 1251, 1253, 1255, 1257, 1259, 1260, 1261, 1263, 1266, 1268, 1270, 1272, 1275, 1278, 1280, 1282, 1284, 1289, 1291, 1295, 1297, 1299, 1301, 1303, 1305, 1312, 1314, 1316, 1318, 1320, 1322, 1328, 1330, 1332, 1335, 1337, 1339, 1341, 1344, 1346, 1348, 1352, 1355, 1357, 1359 or 1362, or a fragment thereof. A plant produced from the plant cell has a difference in drought tolerance or heat tolerance as compared to a control plant that does not comprise the exogenous nucleic acid.

Methods of modulating drought in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-16. A plant produced from the plant cell has a difference in drought tolerance as compared to a control plant that does not comprise the exogenous nucleic acid.

In another aspect, a method of modulating drought tolerance comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NO: 442, 443, 445, 447, 449, 451, 453, 455, 457, 459, 461, 463, 465, 469, 470, 472, 474, 476, 478, 480, 481, 483, 485, 487, 966, 968, 969, 970, 902, 904, 906, 908, 910, 913, 914, 920, 748, 749, 797, 803, 821, 1189, 1191, 1193, 1195, 1197, 1199, 1201, 1203, 1205, 1207, 1209, 1210, 1212, 1214, 1215, 1216, 1218, 1219, 1221, 1222, 1223, 1225, 1226, 1228, 1230, 1231, 1232, 1234, 1236, 1238, 1240, 1244, 1246, 1248, 1250, 1252, 1254, 1256, 1258, 1296, 1298, 1300, 1302, 1304, 489, 490, 491, 492, 494, 496, 498, 500, 502, 504, 506, 508, 510, 512, 514, 515, 516, 518, 519, 520, 522, 524, 526, 528, 530, 531, 533, 535, 536, 538, 540, 541, 543, 545, 547, 548, 550, 552, 553, 555, 557, 558, 561, 562, 564, 566, 856, 869, 870, 871, 872, 873, 874, 568, 569, 570, 572, 574, 576, 578, 580, 582, 584, 586, 588, 795, 590, 591, 592, 593, 594, 595, 596, 597, 598, 599, 600, 602, 603, 604, 605, 607, 608, 610, 612, 614, 615, 616, 617, 618, 619, 620, 621, 623, 625, 627, 629, 631, 632, 634, 635, 636, 638, 640, 642, 644, 646, 647, 650, 651, 653, 654, 655, 656, 658, 660, 661, 662, 663, 664, 665, 666, 667, 668, 669, 671, 673, 674, 675, 676, 678, 680, 682, 684, 685, 687, 688, 690, 691, 692, 694, 696, 698, 700, 702, 971, 974, 975, 978, 979, 980, 981, 983, 985, 987, 995, 997, 705, 706, 707, 708, 709, 711, 712, 714, 715, 717, 719, 721, 723, 725, 727, 729, 731, 733, 734, 735, 737, 738, 740, 746, 747, 751, 752, 787, 742, 743, 744, 745, 757, 759, 761, 763, 767, 771, 796, 798, 799, 801, 805, 807, 808, 809, 810, 811, 812, 813, 815, 816, 817, 819, 823, 825, 832, 834, 836, 839, 846, 848, 857, 859, 863, 885, 892, 900, 912, 918, 939, 944, 953, 955, 957, 973, 977, 988, 989, 990, 991, 992, 993, 999, 1000, 1010, 1242, 922, 924, 929, 931, 935, 937, 941, 943, 947, 949, 951, 952, 958, 959, 960, 961, 962, 963, 964, 1012, 1013, 1014, 1015, 1016, 1018, 1020, 1022, 1023, 1025, 1027, 1028, 1030, 1031, 1033, 1035, 1037, 1039, 1041, 1045, 1048, 1050, 1051, 1053, 1055, 1056, 1058, 1061, 1062, 1064, 1066, 1068, 1071, 1073, 1075, 1077, 1079, 1080, 1082, 1084, 1086, 1088, 1090, 1092, 1093, 1094, 1096, 1098, 1100, 1102, 1104, 1106, 1108, 1110, 1112, 1113, 1114, 1116, 1117, 1118, 1119, 1121, 1123, 1125, 1292, 63, 73, 96, 127, 139, 179, 180, 209, 467, 559, 648, 726, 741, 765, 773, 781, 827, 829, 840, 841, 842, 843, 844, 845, 849, 850, 851, 852, 853, 854, 861, 865, 867, 896, 916, 926, 932, 933, 1043, 1046, 1059, 1069, 1129, 1130, 1131, 1132, 1133, 1134, 1135, 1136, 1137, 1138, 1140, 1142, 1144, 1146, 1148, 1150, 1151, 1152, 1153, 1154, 1156, 1157, 1158, 1159, 1160, 1161, 1162, 1164, 1166, 1168, 1170, 1172, 1174, 1175, 1177, 1179, 1181, 1182, 1184, 1186, 1294, 1311, 1313, 1315, 1317, 1319, 1321, 1323, 1324, 1325, 1326, 1327, 1329, 1331, 1333, 1334, 1336, 1338, 1340, 1342, 1343, 1345, 1347, 1349, 1350, 1351, 1353, 1354, 1356, 1358, 1360, or 1361. A plant produced from the plant cell has a difference in drought tolerance as compared to a control plant that does not comprise the exogenous nucleic acid.

In another aspect, a method of modulating drought tolerance comprises introducing into a plant cell an exogenous nucleic acid, that comprises a regulatory region operably linked to a nucleotide sequence having 80 percent or greater sequence identity to a nucleotide sequence set forth in SEQ ID NO: 923, 994, 905, 921, 804, 837, 828, 930, 996, 928, 868, 645, 641, 695, 505, 1067, 501, 466, 718, 860, 503, 624, 628, 630, 639, 686, 806, 479, 764, 1060, 1052, 1120, 1105, 546, 780, 460, 814, 800, 499, 643, 670, 679, 1253, 927, 716, 1081, 128, 585, 581, 864, 1049, 1107, 523, 1076, 652, 1095, 1099, 1101, 497, 830, 507, 622, 140, 772, 532, 542, 549, 226, 1149, 210, 587, 583, 866, 527, 1097, 1103, 1141, 1019, 486, 1229, 1249, 739, 697, 701, 1011, 563, 1122, 1243, 1208, 1247, 1009, 1124, 699, 1206, 72, 565, 1245, 1021, 1008, 942, 948, 818, 794, 967, 986, 786, 936, 940, 984, 855, 946, 982, 1291, 919, 822, 824, 907, 750, 909, 934, 903, 826, 95, 965, 950, 611, 575, 1190, 484, 454, 1036, 722, 444, 456, 1192, 1034, 720, 831, 911, 838, 917, 468, 1257, 659, 1173, 1139, 1176, 938, 1063, 1032, 862, 758, 450, 509, 554, 1259, 458, 1217, 972, 477, 462, 954, 1163, 956, 525, 556, 1145, 1165, 1065, 677, 609, 762, 537, 1169, 884, 1198, 1085, 1109, 1211, 1029, 689, 1070, 1233, 770, 1047, 1194, 551, 446, 633, 1167, 1078, 1213, 730, 448, 766, 895, 511, 925, 495, 1239, 1235, 1057, 1074, 1202, 544, 1083, 1024, 1220, 1224, 1200, 613, 683, 672, 976, 517, 1227, 471, 1255, 1237, 473, 728, 521, 464, 1241, 1155, 681, 736, 539, 1017, 513, 835, 657, 534, 1044, 649, 1026, 560, 1171, 579, 1038, 529, 1091, 1147, 637, 452, 1072, 1180, 833, 1040, 1089, 482, 493, 732, 1115, 626, 899, 606, 1178, 1087, 1042, 1111, 577, 1251, 475, 858, 724, 1183, 693, 1143, 1185, 1054, 1187, 571, 713, 847, 1196, 573, 1204, 601, 441, 488, 567, 589, 703, 704, 710, 1260, 1126, 1127, 1128, 1295, 802, 1303, 1297, 1301, 1299, 820, 1312, 1314, 1316, 1318, 1320, 1322, 1328, 1330, 1332, 1335, 1337, 1339, 1341, 1344, 1346, 1348, 1352, 1355, 1357, 1359 or 1362, or a fragment thereof. A plant produced from the plant cell has a difference in drought tolerance as compared to a control plant that does not comprise the exogenous nucleic acid.

Methods of modulating heat in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 10-14. A plant produced from the plant cell has a difference in heat tolerance as compared to a control plant that does not comprise the exogenous nucleic acid.

In another aspect, a method of modulating heat tolerance comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NO: 60, 62, 64, 65, 66, 67, 68, 69, 70, 71, 74, 76, 78, 80, 82, 84, 86, 88, 90, 92, 94, 98, 100, 102, 104, 106, 108, 110, 112, 114, 116, 118, 120, 122, 124, 126, 130, 132, 134, 136, 138, 142, 144, 146, 148, 150, 152, 154, 156, 158, 915, 364, 366, 368, 369, 370, 371, 373, 375, 377, 379, 381, 383, 385, 387, 389, 390, 392, 394, 396, 398, 400, 401, 402, 404, 405, 407, 408, 410, 412, 413, 414, 416, 418, 419, 420, 421, 422, 423, 424, 426, 428, 430, 431, 432, 433, 434, 435, 436, 438, 440, 753, 754, 755, 756, 760, 768, 769, 774, 775, 777, 779, 783, 785, 789, 791, 793, 945, 1293, 311, 312, 314, 315, 316, 317, 319, 320, 321, 322, 323, 325, 326, 327, 329, 330, 332, 334, 335, 336, 337, 338, 339, 340, 341, 343, 344, 346, 348, 349, 350, 351, 353, 355, 356, 358, 360, 362, 876, 878, 880, 882, 886, 887, 888, 889, 890, 891, 893, 894, 897, 898, 901, 160, 162, 164, 166, 168, 170, 172, 174, 176, 178, 182, 184, 186, 188, 190, 192, 194, 196, 198, 200, 202, 204, 206, 208, 212, 214, 216, 218, 220, 222, 224, 225, 228, 229, 231, 233, 234, 235, 237, 239, 240, 242, 244, 246, 248, 250, 252, 253, 254, 256, 258, 260, 262, 264, 266, 268, 269, 271, 273, 275, 277, 279, 280, 282, 284, 286, 288, 289, 290, 291, 292, 293, 294, 295, 296, 297, 298, 299, 300, 301, 302, 303, 304, 305, 307, 309, 998, 1001, 1003, 1005, 1007, 1188, 1262, 1264, 1265, 1267, 1269, 1271, 1273, 1274, 1276, 1277, 1279, 1281, 1283, 1285, 1286, 1287, 1288, 1290, 2, 3, 4, 5, 6, 7, 8, 9, 10, 11, 13, 15, 17, 19, 21, 23, 25, 27, 29, 31, 33, 35, 37, 39, 41, 43, 45, 47, 49, 51, 53, 55, 902, 904, 906, 908, 910, 913, 914, or 920. A plant produced from the plant cell has a difference in heat tolerance as compared to a control plant that does not comprise the exogenous nucleic acid.

In another aspect, a method of modulating heat tolerance comprises introducing into a plant cell an exogenous nucleic acid, that comprises a regulatory region operably linked to a nucleotide sequence having 80 percent or greater sequence identity to a nucleotide sequence set forth in SEQ ID NO: 877, 1263, 790, 1261, 875, 792, 201, 354, 85, 77, 75, 415, 46, 207, 333, 203, 382, 83, 411, 81, 425, 406, 189, 93, 223, 44, 345, 79, 199, 417, 42, 219, 352, 185, 193, 89, 205, 386, 365, 91, 211, 195, 217, 429, 213, 187, 221, 359, 40, 197, 357, 331, 215, 183, 191, 367, 318, 87, 378, 48, 157, 155, 306, 361, 439, 52, 50, 437, 308, 54, 153, 1002, 782, 1266, 1268, 1275, 881, 784, 1278, 1280, 1004, 778, 879, 1282, 1006, 1289, 1284, 1270, 788, 883, 1272, 776, 135, 259, 109, 245, 121, 28, 115, 261, 151, 145, 328, 313, 24, 20, 391, 99, 409, 272, 1, 342, 347, 374, 131, 372, 111, 103, 107, 388, 125, 117, 18, 380, 123, 129, 26, 399, 143, 283, 30, 167, 403, 287, 137, 281, 169, 161, 14, 165, 181, 12, 38, 163, 173, 324, 177, 34, 97, 175, 171, 101, 285, 36, 276, 274, 232, 56, 270, 376, 278, 58, 59, 16, 230, 141, 32, 267, 227, 159, 241, 133, 249, 397, 247, 263, 149, 393, 395, 257, 243, 251, 113, 265, 119, 384, 427, 147, 255, 61, 22, 238, 236, 105, 310, or 363, or a fragment thereof. A plant produced from the plant cell has a difference in heat tolerance as compared to a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-16. A plant produced from the cells has a difference in drought tolerance or heat tolerance as compared to a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO: 2, 3, 4, 5, 6, 7, 8, 9, 10, 11, 13, 15, 17, 19, 21, 23, 25, 27, 29, 31, 33, 35, 37, 39, 41, 43, 45, 47, 49, 51, 53, 55, 57, 60, 62, 63, 64, 65, 66, 67, 68, 69, 70, 71, 73, 74, 76, 78, 80, 82, 84, 86, 88, 90, 92, 94, 96, 98, 100, 102, 104, 106, 108, 110, 112, 114, 116, 118, 120, 122, 124, 126, 127, 130, 132, 134, 136, 138, 139, 142, 144, 146, 148, 150, 152, 154, 156, 158, 160, 162, 164, 166, 168, 170, 172, 174, 176, 178, 179, 180, 182, 184, 186, 188, 190, 192, 194, 196, 198, 200, 202, 204, 206, 208, 209, 212, 214, 216, 218, 220, 222, 224, 225, 228, 229, 231, 233, 234, 235, 237, 239, 240, 242, 244, 246, 248, 250, 252, 253, 254, 256, 258, 260, 262, 264, 266, 268, 269, 271, 273, 275, 277, 279, 280, 282, 284, 286, 288, 289, 290, 291, 292, 293, 294, 295, 296, 297, 298, 299, 300, 301, 302, 303, 304, 305, 307, 309, 311, 312, 314, 315, 316, 317, 319, 320, 321, 322, 323, 325, 326, 327, 329, 330, 332, 334, 335, 336, 337, 338, 339, 340, 341, 343, 344, 346, 348, 349, 350, 351, 353, 355, 356, 358, 360, 362, 364, 366, 368, 369, 370, 371, 373, 375, 377, 379, 381, 383, 385, 387, 389, 390, 392, 394, 396, 398, 400, 401, 402, 404, 405, 407, 408, 410, 412, 413, 414, 416, 418, 419, 420, 421, 422, 423, 424, 426, 428, 430, 431, 432, 433, 434, 435, 436, 438, 440, 442, 443, 445, 447, 449, 451, 453, 455, 457, 459, 461, 463, 465, 467, 469, 470, 472, 474, 476, 478, 480, 481, 483, 485, 487, 489, 490, 491, 492, 494, 496, 498, 500, 502, 504, 506, 508, 510, 512, 514, 515, 516, 518, 519, 520, 522, 524, 526, 528, 530, 531, 533, 535, 536, 538, 540, 541, 543, 545, 547, 548, 550, 552, 553, 555, 557, 558, 559, 561, 562, 564, 566, 568, 569, 570, 572, 574, 576, 578, 580, 582, 584, 586, 588, 590, 591, 592, 593, 594, 595, 596, 597, 598, 599, 600, 602, 603, 604, 605, 607, 608, 610, 612, 614, 615, 616, 617, 618, 619, 620, 621, 623, 625, 627, 629, 631, 632, 634, 635, 636, 638, 640, 642, 644, 646, 647, 648, 650, 651, 653, 654, 655, 656, 658, 660, 661, 662, 663, 664, 665, 666, 667, 668, 669, 671, 673, 674, 675, 676, 678, 680, 682, 684, 685, 687, 688, 690, 691, 692, 694, 696, 698, 700, 702, 705, 706, 707, 708, 709, 711, 712, 714, 715, 717, 719, 721, 723, 725, 726, 727, 729, 731, 733, 734, 735, 737, 738, 740, 741, 742, 743, 744, 745, 746, 747, 748, 749, 751, 752, 753, 754, 755, 756, 757, 759, 760, 761, 763, 765, 767, 768, 769, 771, 773, 774, 775, 777, 779, 781, 783, 785, 787, 789, 791, 793, 795, 796, 797, 798, 799, 801, 803, 805, 807, 808, 809, 810, 811, 812, 813, 815, 816, 817, 819, 821, 823, 825, 827, 829, 832, 834, 836, 839, 840, 841, 842, 843, 844, 845, 846, 848, 849, 850, 851, 852, 853, 854, 856, 857, 859, 861, 863, 865, 867, 869, 870, 871, 872, 873, 874, 876, 878, 880, 882, 885, 886, 887, 888, 889, 890, 891, 892, 893, 894, 896, 897, 898, 900, 901, 902, 904, 906, 908, 910, 912, 913, 914, 915, 916, 918, 920, 922, 924, 926, 929, 931, 932, 933, 935, 937, 939, 941, 943, 944, 945, 947, 949, 951, 952, 953, 955, 957, 958, 959, 960, 961, 962, 963, 964, 966, 968, 969, 970, 971, 973, 974, 975, 977, 978, 979, 980, 981, 983, 985, 987, 988, 989, 990, 991, 992, 993, 995, 997, 998, 999, 1000, 1001, 1003, 1005, 1007, 1010, 1012, 1013, 1014, 1015, 1016, 1018, 1020, 1022, 1023, 1025, 1027, 1028, 1030, 1031, 1033, 1035, 1037, 1039, 1041, 1043, 1045, 1046, 1048, 1050, 1051, 1053, 1055, 1056, 1058, 1059, 1061, 1062, 1064, 1066, 1068, 1069, 1071, 1073, 1075, 1077, 1079, 1080, 1082, 1084, 1086, 1088, 1090, 1092, 1093, 1094, 1096, 1098, 1100, 1102, 1104, 1106, 1108, 1110, 1112, 1113, 1114, 1116, 1117, 1118, 1119, 1121, 1123, 1125, 1129, 1130, 1131, 1132, 1133, 1134, 1135, 1136, 1137, 1138, 1140, 1142, 1144, 1146, 1148, 1150, 1151, 1152, 1153, 1154, 1156, 1157, 1158, 1159, 1160, 1161, 1162, 1164, 1166, 1168, 1170, 1172, 1174, 1175, 1177, 1179, 1181, 1182, 1184, 1186, 1188, 1189, 1191, 1193, 1195, 1197, 1199, 1201, 1203, 1205, 1207, 1209, 1210, 1212, 1214, 1215, 1216, 1218, 1219, 1221, 1222, 1223, 1225, 1226, 1228, 1230, 1231, 1232, 1234, 1236, 1238, 1240, 1242, 1244, 1246, 1248, 1250, 1252, 1254, 1256, 1258, 1262, 1264, 1265, 1267, 1269, 1271, 1273, 1274, 1276, 1277, 1279, 1281, 1283, 1285, 1286, 1287, 1288, 1290, 1292, 1293, 1294, 1296, 1298, 1300, 1302, 1304, or 1311, 1313, 1315, 1317, 1319, 1321, 1323, 1324, 1325, 1326, 1327, 1329, 1331, 1333, 1334, 1336, 1338, 1340, 1342, 1343, 1345, 1347, 1349, 1350, 1351, 1353, 1354, 1356, 1358, 1360, or 1361. A plant produced from the plant cell has a difference in drought tolerance or heat tolerance as compared to a control plant that does not comprise the exogenous nucleic acid.

In another aspect, the exogenous nucleic acid comprises a regulatory region operably linked to a nucleotide sequence having 80 percent or greater sequence identity to a nucleotide sequence selected from the group consisting of SEQ ID NO: 1, 12, 14, 16, 18, 20, 22, 24, 26, 28, 30, 32, 34, 36, 38, 40, 42, 44, 46, 48, 50, 52, 54, 56, 58, 59, 61, 72, 75, 77, 79, 81, 83, 85, 87, 89, 91, 93, 95, 97, 99, 101, 103, 105, 107, 109, 111, 113, 115, 117, 119, 121, 123, 125, 128, 129, 131, 133, 135, 137, 140, 141, 143, 145, 147, 149, 151, 153, 155, 157, 159, 161, 163, 165, 167, 169, 171, 173, 175, 177, 181, 183, 185, 187, 189, 191, 193, 195, 197, 199, 201, 203, 205, 207, 210, 211, 213, 215, 217, 219, 221, 223, 226, 227, 230, 232, 236, 238, 241, 243, 245, 247, 249, 251, 255, 257, 259, 261, 263, 265, 267, 270, 272, 274, 276, 278, 281, 283, 285, 287, 306, 308, 310, 313, 318, 324, 328, 331, 333, 342, 345, 347, 352, 354, 357, 359, 361, 363, 365, 367, 372, 374, 376, 378, 380, 382, 384, 386, 388, 391, 393, 395, 397, 399, 403, 406, 409, 411, 415, 417, 425, 427, 429, 437, 439, 441, 444, 446, 448, 450, 452, 454, 456, 458, 460, 462, 464, 466, 468, 471, 473, 475, 477, 479, 482, 484, 486, 488, 493, 495, 497, 499, 501, 503, 505, 507, 509, 511, 513, 517, 521, 523, 525, 527, 529, 532, 534, 537, 539, 542, 544, 546, 549, 551, 554, 556, 560, 563, 565, 567, 571, 573, 575, 577, 579, 581, 583, 585, 587, 589, 601, 606, 609, 611, 613, 622, 624, 626, 628, 630, 633, 637, 639, 641, 643, 645, 649, 652, 657, 659, 670, 672, 677, 679, 681, 683, 686, 689, 693, 695, 697, 699, 701, 703, 704, 710, 713, 716, 718, 720, 722, 724, 728, 730, 732, 736, 739, 750, 758, 762, 764, 766, 770, 772, 776, 778, 780, 782, 784, 786, 788, 790, 792, 794, 800, 802, 804, 806, 814, 818, 820, 822, 824, 826, 828, 830, 831, 833, 835, 837, 838, 847, 855, 858, 860, 862, 864, 866, 868, 875, 877, 879, 881, 883, 884, 895, 899, 903, 905, 907, 909, 911, 917, 919, 921, 923, 925, 927, 928, 930, 934, 936, 938, 940, 942, 946, 948, 950, 954, 956, 965, 967, 972, 976, 982, 984, 986, 994, 996, 1002, 1004, 1006, 1008, 1009, 1011, 1017, 1019, 1021, 1024, 1026, 1029, 1032, 1034, 1036, 1038, 1040, 1042, 1044, 1047, 1049, 1052, 1054, 1057, 1060, 1063, 1065, 1067, 1070, 1072, 1074, 1076, 1078, 1081, 1083, 1085, 1087, 1089, 1091, 1095, 1097, 1099, 1101, 1103, 1105, 1107, 1109, 1111, 1115, 1120, 1122, 1124, 1126, 1127, 1128, 1139, 1141, 1143, 1145, 1147, 1149, 1155, 1163, 1165, 1167, 1169, 1171, 1173, 1176, 1178, 1180, 1183, 1185, 1187, 1190, 1192, 1194, 1196, 1198, 1200, 1202, 1204, 1206, 1208, 1211, 1213, 1217, 1220, 1224, 1227, 1229, 1233, 1235, 1237, 1239, 1241, 1243, 1245, 1247, 1249, 1251, 1253, 1255, 1257, 1259, 1260, 1261, 1263, 1266, 1268, 1270, 1272, 1275, 1278, 1280, 1282, 1284, 1289, 1291, 1295, 1297, 1299, 1301, 1303, 1312, 1314, 1316, 1318, 1320, 1322, 1328, 1330, 1332, 1335, 1337, 1339, 1341, 1344, 1346, 1348, 1352, 1355, 1357, 1359 or 1362, or a fragment thereof. A plant produced from the plant cell has a difference in drought or heat tolerance as compared to a control plant that does not comprise the exogenous nucleic acid. A transgenic plant comprising such a plant cell is also provided.

Transgenic plants of any aspect provided herein can be a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Isolated nucleic acids are also provided. In one aspect, an isolated nucleic acid comprises a nucleotide sequence having 80% or greater sequence identity to the nucleotide sequence set forth in SEQ ID NO: 1, 12, 14, 16, 18, 20, 22, 24, 26, 28, 30, 32, 34, 36, 38, 40, 42, 44, 46, 48, 50, 52, 54, 56, 58, 59, 61, 72, 75, 77, 79, 81, 83, 85, 87, 89, 91, 93, 95, 97, 99, 101, 103, 105, 107, 109, 111, 113, 115, 117, 119, 121, 123, 125, 128, 129, 131, 133, 135, 137, 140, 141, 143, 145, 147, 149, 151, 153, 155, 157, 159, 161, 163, 165, 167, 169, 171, 173, 175, 177, 181, 183, 185, 187, 189, 191, 193, 195, 197, 199, 201, 203, 205, 207, 210, 211, 213, 215, 217, 219, 221, 223, 226, 227, 230, 232, 236, 238, 241, 243, 245, 247, 249, 251, 255, 257, 259, 261, 263, 265, 267, 270, 272, 274, 276, 278, 281, 283, 285, 287, 306, 308, 310, 313, 318, 324, 328, 331, 333, 342, 345, 347, 352, 354, 357, 359, 361, 363, 365, 367, 372, 374, 376, 378, 380, 382, 384, 386, 388, 391, 393, 395, 397, 399, 403, 406, 409, 411, 415, 417, 425, 427, 429, 437, 439, 441, 444, 446, 448, 450, 452, 454, 456, 458, 460, 462, 464, 466, 468, 471, 473, 475, 477, 479, 482, 484, 486, 488, 493, 495, 497, 499, 501, 503, 505, 507, 509, 511, 513, 517, 521, 523, 525, 527, 529, 532, 534, 537, 539, 542, 544, 546, 549, 551, 554, 556, 560, 563, 565, 567, 571, 573, 575, 577, 579, 581, 583, 585, 587, 589, 601, 606, 609, 611, 613, 622, 624, 626, 628, 630, 633, 637, 639, 641, 643, 645, 649, 652, 657, 659, 670, 672, 677, 679, 681, 683, 686, 689, 693, 695, 697, 699, 701, 703, 704, 710, 713, 716, 718, 720, 722, 724, 728, 730, 732, 736, 739, 750, 758, 762, 764, 766, 770, 772, 776, 778, 780, 782, 784, 786, 788, 790, 792, 794, 800, 802, 804, 806, 814, 818, 820, 822, 824, 826, 828, 830, 831, 833, 835, 837, 838, 847, 855, 858, 860, 862, 864, 866, 868, 875, 877, 879, 881, 883, 884, 895, 899, 903, 905, 907, 909, 911, 917, 919, 921, 923, 925, 927, 928, 930, 934, 936, 938, 940, 942, 946, 948, 950, 954, 956, 965, 967, 972, 976, 982, 984, 986, 994, 996, 1002, 1004, 1006, 1008, 1009, 1011, 1017, 1019, 1021, 1024, 1026, 1029, 1032, 1034, 1036, 1038, 1040, 1042, 1044, 1047, 1049, 1052, 1054, 1057, 1060, 1063, 1065, 1067, 1070, 1072, 1074, 1076, 1078, 1081, 1083, 1085, 1087, 1089, 1091, 1095, 1097, 1099, 1101, 1103, 1105, 1107, 1109, 1111, 1115, 1120, 1122, 1124, 1126, 1127, 1128, 1139, 1141, 1143, 1145, 1147, 1149, 1155, 1163, 1165, 1167, 1169, 1171, 1173, 1176, 1178, 1180, 1183, 1185, 1187, 1190, 1192, 1194, 1196, 1198, 1200, 1202, 1204, 1206, 1208, 1211, 1213, 1217, 1220, 1224, 1227, 1229, 1233, 1235, 1237, 1239, 1241, 1243, 1245, 1247, 1249, 1251, 1253, 1255, 1257, 1259, 1260, 1261, 1263, 1266, 1268, 1270, 1272, 1275, 1278, 1280, 1282, 1284, 1289, 1291, 1295, 1297, 1299, 1301, 1303, 1312, 1314, 1316, 1318, 1320, 1322, 1328, 1330, 1332, 1335, 1337, 1339, 1341, 1344, 1346, 1348, 1352, 1355, 1357, 1359 or 1362, or a fragment thereof.

In another aspect, an isolated nucleic acid comprises a nucleotide sequence encoding a polypeptide having 80% or greater sequence identity to the amino acid sequence set forth in SEQ ID NO: 2, 3, 4, 5, 6, 7, 8, 9, 10, 11, 13, 15, 17, 19, 21, 23, 25, 27, 29, 31, 33, 35, 37, 39, 41, 43, 45, 47, 49, 51, 53, 55, 57, 60, 62, 63, 64, 65, 66, 67, 68, 69, 70, 71, 73, 74, 76, 78, 80, 82, 84, 86, 88, 90, 92, 94, 96, 98, 100, 102, 104, 106, 108, 110, 112, 114, 116, 118, 120, 122, 124, 126, 127, 130, 132, 134, 136, 138, 139, 142, 144, 146, 148, 150, 152, 154, 156, 158, 160, 162, 164, 166, 168, 170, 172, 174, 176, 178, 179, 180, 182, 184, 186, 188, 190, 192, 194, 196, 198, 200, 202, 204, 206, 208, 209, 212, 214, 216, 218, 220, 222, 224, 225, 228, 229, 231, 233, 234, 235, 237, 239, 240, 242, 244, 246, 248, 250, 252, 253, 254, 256, 258, 260, 262, 264, 266, 268, 269, 271, 273, 275, 277, 279, 280, 282, 284, 286, 288, 289, 290, 291, 292, 293, 294, 295, 296, 297, 298, 299, 300, 301, 302, 303, 304, 305, 307, 309, 311, 312, 314, 315, 316, 317, 319, 320, 321, 322, 323, 325, 326, 327, 329, 330, 332, 334, 335, 336, 337, 338, 339, 340, 341, 343, 344, 346, 348, 349, 350, 351, 353, 355, 356, 358, 360, 362, 364, 366, 368, 369, 370, 371, 373, 375, 377, 379, 381, 383, 385, 387, 389, 390, 392, 394, 396, 398, 400, 401, 402, 404, 405, 407, 408, 410, 412, 413, 414, 416, 418, 419, 420, 421, 422, 423, 424, 426, 428, 430, 431, 432, 433, 434, 435, 436, 438, 440, 442, 443, 445, 447, 449, 451, 453, 455, 457, 459, 461, 463, 465, 467, 469, 470, 472, 474, 476, 478, 480, 481, 483, 485, 487, 489, 490, 491, 492, 494, 496, 498, 500, 502, 504, 506, 508, 510, 512, 514, 515, 516, 518, 519, 520, 522, 524, 526, 528, 530, 531, 533, 535, 536, 538, 540, 541, 543, 545, 547, 548, 550, 552, 553, 555, 557, 558, 559, 561, 562, 564, 566, 568, 569, 570, 572, 574, 576, 578, 580, 582, 584, 586, 588, 590, 591, 592, 593, 594, 595, 596, 597, 598, 599, 600, 602, 603, 604, 605, 607, 608, 610, 612, 614, 615, 616, 617, 618, 619, 620, 621, 623, 625, 627, 629, 631, 632, 634, 635, 636, 638, 640, 642, 644, 646, 647, 648, 650, 651, 653, 654, 655, 656, 658, 660, 661, 662, 663, 664, 665, 666, 667, 668, 669, 671, 673, 674, 675, 676, 678, 680, 682, 684, 685, 687, 688, 690, 691, 692, 694, 696, 698, 700, 702, 705, 706, 707, 708, 709, 711, 712, 714, 715, 717, 719, 721, 723, 725, 726, 727, 729, 731, 733, 734, 735, 737, 738, 740, 741, 742, 743, 744, 745, 746, 747, 748, 749, 751, 752, 753, 754, 755, 756, 757, 759, 760, 761, 763, 765, 767, 768, 769, 771, 773, 774, 775, 777, 779, 781, 783, 785, 787, 789, 791, 793, 795, 796, 797, 798, 799, 801, 803, 805, 807, 808, 809, 810, 811, 812, 813, 815, 816, 817, 819, 821, 823, 825, 827, 829, 832, 834, 836, 839, 840, 841, 842, 843, 844, 845, 846, 848, 849, 850, 851, 852, 853, 854, 856, 857, 859, 861, 863, 865, 867, 869, 870, 871, 872, 873, 874, 876, 878, 880, 882, 885, 886, 887, 888, 889, 890, 891, 892, 893, 894, 896, 897, 898, 900, 901, 902, 904, 906, 908, 910, 912, 913, 914, 915, 916, 918, 920, 922, 924, 926, 929, 931, 932, 933, 935, 937, 939, 941, 943, 944, 945, 947, 949, 951, 952, 953, 955, 957, 958, 959, 960, 961, 962, 963, 964, 966, 968, 969, 970, 971, 973, 974, 975, 977, 978, 979, 980, 981, 983, 985, 987, 988, 989, 990, 991, 992, 993, 995, 997, 998, 999, 1000, 1001, 1003, 1005, 1007, 1010, 1012, 1013, 1014, 1015, 1016, 1018, 1020, 1022, 1023, 1025, 1027, 1028, 1030, 1031, 1033, 1035, 1037, 1039, 1041, 1043, 1045, 1046, 1048, 1050, 1051, 1053, 1055, 1056, 1058, 1059, 1061, 1062, 1064, 1066, 1068, 1069, 1071, 1073, 1075, 1077, 1079, 1080, 1082, 1084, 1086, 1088, 1090, 1092, 1093, 1094, 1096, 1098, 1100, 1102, 1104, 1106, 1108, 1110, 1112, 1113, 1114, 1116, 1117, 1118, 1119, 1121, 1123, 1125, 1129, 1130, 1131, 1132, 1133, 1134, 1135, 1136, 1137, 1138, 1140, 1142, 1144, 1146, 1148, 1150, 1151, 1152, 1153, 1154, 1156, 1157, 1158, 1159, 1160, 1161, 1162, 1164, 1166, 1168, 1170, 1172, 1174, 1175, 1177, 1179, 1181, 1182, 1184, 1186, 1188, 1189, 1191, 1193, 1195, 1197, 1199, 1201, 1203, 1205, 1207, 1209, 1210, 1212, 1214, 1215, 1216, 1218, 1219, 1221, 1222, 1223, 1225, 1226, 1228, 1230, 1231, 1232, 1234, 1236, 1238, 1240, 1242, 1244, 1246, 1248, 1250, 1252, 1254, 1256, 1258, 1262, 1264, 1265, 1267, 1269, 1271, 1273, 1274, 1276, 1277, 1279, 1281, 1283, 1285, 1286, 1287, 1288, 1290, 1292, 1293, 1294, 1296, 1298, 1300, 1302, 1304, or 1311, 1313, 1315, 1317, 1319, 1321, 1323, 1324, 1325, 1326, 1327, 1329, 1331, 1333, 1334, 1336, 1338, 1340, 1342, 1343, 1345, 1347, 1349, 1350, 1351, 1353, 1354, 1356, 1358, 1360, or 1361.

In another aspect, methods of identifying a genetic polymorphism associated with variation in drought tolerance or heat tolerance are provided. The methods include providing a population of plants, and determining whether one or more genetic polymorphisms in the population are genetically linked to the locus for a polypeptide selected from the group consisting of the polypeptides depicted in FIGS. 1-16 and functional homologs thereof. The correlation between variation in drought tolerance or heat tolerance in plants of the population and the presence of the one or more genetic polymorphisms in plants of the population is measured, thereby permitting identification of whether or not the one or more genetic polymorphisms are associated with such variation. The population can be a population of switchgrass, sorghum, sugar cane, or miscanthus plants.

In another aspect, methods of making a plant line are provided. The methods include determining whether one or more genetic polymorphisms in a population of plants is associated with the locus for a polypeptide selected from the group consisting of the polypeptides depicted in FIGS. 1-16 and functional homologs thereof; identifying one or more plants in said population in which the presence of at least one allele at the one or more genetic polymorphisms is associated with variation in drought tolerance or heat tolerance; crossing each of the one or more identified plants with itself or a different plant to produce seed; crossing at least one progeny plant grown from the seed with itself or a different plant; and repeating the crossing steps for an additional 0-5 generations to make the plant line, where at least one allele is present in the plant line. The population can be a population of switchgrass, sorghum, sugar cane, or miscanthus plants.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or by "consisting of," according to standard practice in patent law.

DESCRIPTION OF THE DRAWINGS

FIG. 1 is an alignment of Ceres SEEDLINE ID no. ME00029 (SEQ ID NO:442) with homologous and/or orthologous sequences, including, Public GI ID no. 72384401 (SEQ ID NO:443), Ceres CLONE ID no. 1079382 (SEQ ID NO:445), Ceres CLONE ID no. 1853461 (SEQ ID NO:447), Ceres CLONE ID no. 1626485 (SEQ ID NO:451), Ceres CLONE ID no. 1713920 (SEQ ID NO:459), Ceres CLONE ID no. 1772747 (SEQ ID NO:463), Ceres CLONE ID no. 225960 (SEQ ID NO:465), Public GI ID no. 115443807 (SEQ ID NO:470), and Ceres CLONE ID no. 569388 (SEQ ID NO:483). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of Ceres SEEDLINE ID no. ME00045 (SEQ ID NO:489) with homologous and/or orthologous sequences, including, Ceres CLONE ID no. 571200 (SEQ ID NO:494), Ceres CLONE ID no. 1928532 (SEQ ID NO:496), Ceres ANNOT ID no. 1490637 (SEQ ID NO:498), Ceres CLONE ID no. 295496 (SEQ ID NO:514), Public GI ID no. 115463637 (SEQ ID NO:515), and Ceres CLONE ID no. 1999444 (SEQ ID NO:518).

FIG. 3 is an alignment of Ceres SEEDLINE ID no. ME02190 (SEQ ID NO:568) with homologous and/or orthologous sequences, including Ceres CLONE ID no. 695006 (SEQ ID NO:578) and Ceres ANNOT ID no. 1527488 (SEQ ID NO:584).

FIG. 4 is an alignment of Ceres SEEDLINE ID no. ME02549 (SEQ ID NO:590) with homologous and/or orthologous sequences, including, Ceres ANNOT ID no.

1501305 (SEQ ID NO:623), Ceres CLONE ID no. 607280 (SEQ ID NO:627), Public GI ID no. 92887174 (SEQ ID NO:632), Ceres CLONE ID no. 1857162 (SEQ ID NO:634), Public GI ID no. 115477272 (SEQ ID NO:674), and Ceres CLONE ID no. 264002 (SEQ ID NO:682).

FIG. 5 is an alignment of Ceres SEEDLINE ID no. ME02865 (SEQ ID NO:705) with homologous and/or orthologous sequences, including, Public GI ID no. 79320952 (SEQ ID NO:706) and Public GI ID no. 79320957 (SEQ ID NO:707).

Figure 6:
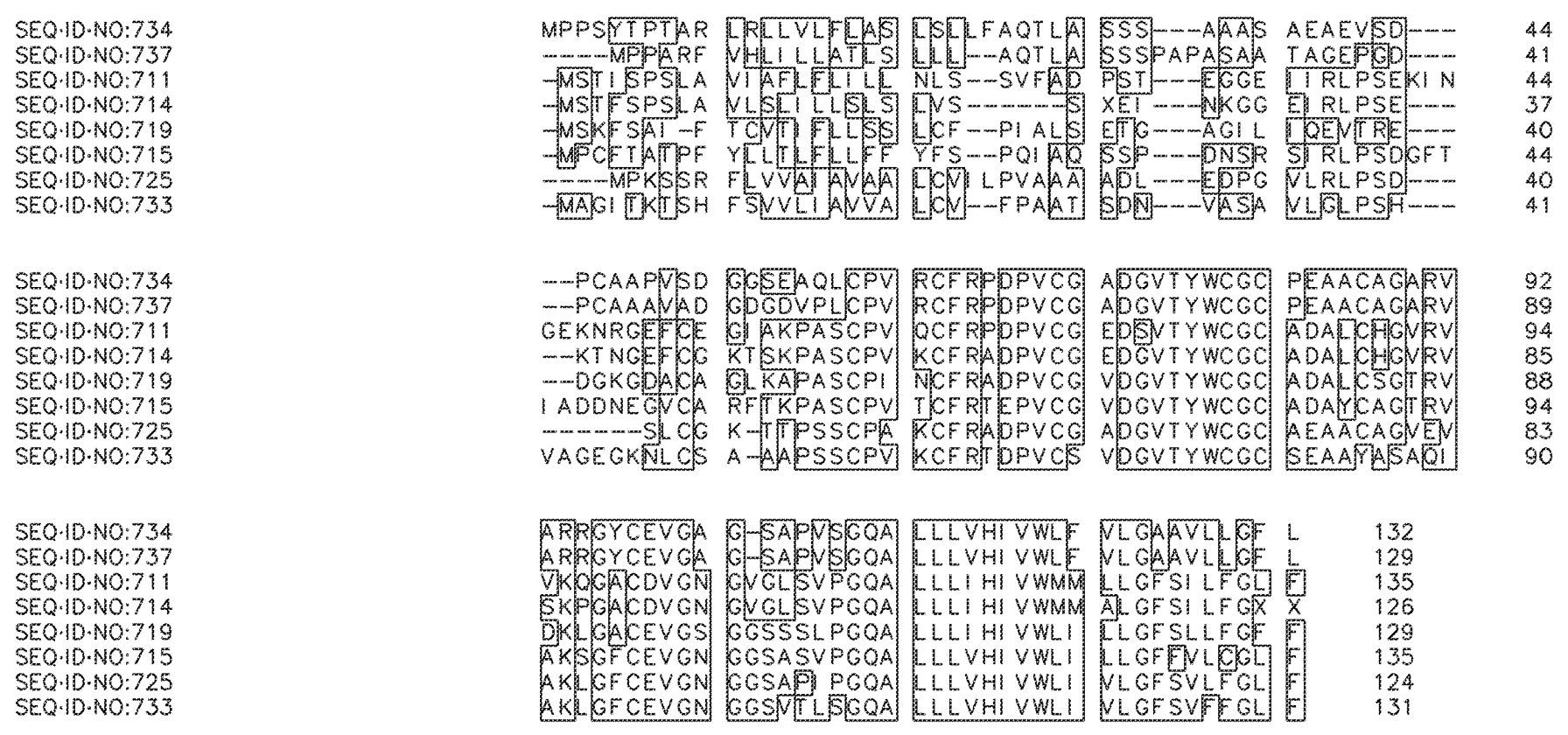

FIG. 6 is an alignment of Ceres SEEDLINE ID no. ME03227 (SEQ ID NO:711) with homologous and/or orthologous sequences, including, Ceres CLONE ID no. 964616 (SEQ ID NO:714), Ceres CLONE ID no. 100009667 (SEQ ID NO:715), Ceres ANNOT ID no. 1444568 (SEQ ID NO:719), Ceres CLONE ID no. 719489 (SEQ ID NO:725), Ceres CLONE ID no. 587748 (SEQ ID NO:733), Public GI ID no. 125528114 (SEQ ID NO:734), and Ceres CLONE ID no. 274172 (SEQ ID NO:737).

Figure 7:
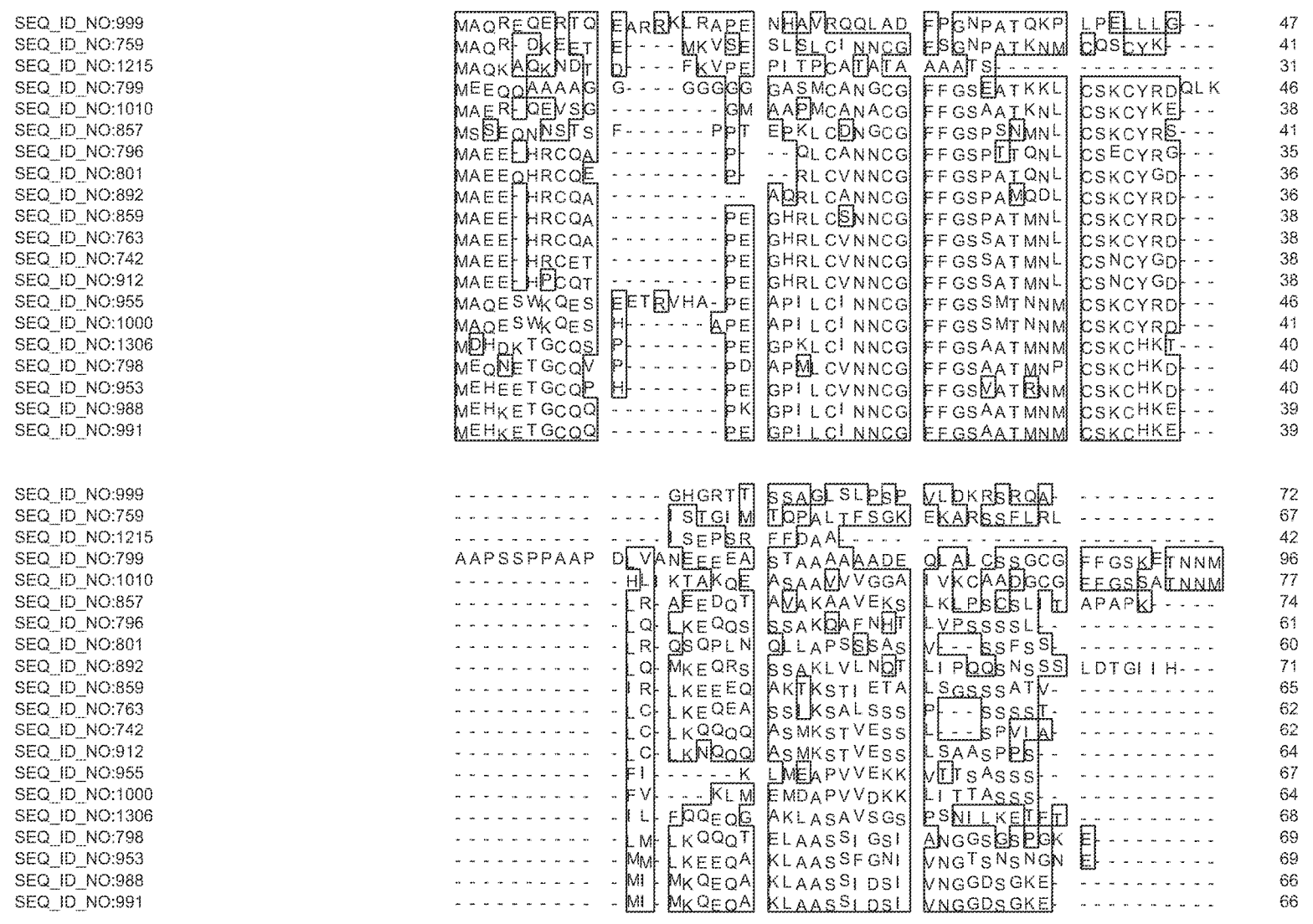
Figure 7:
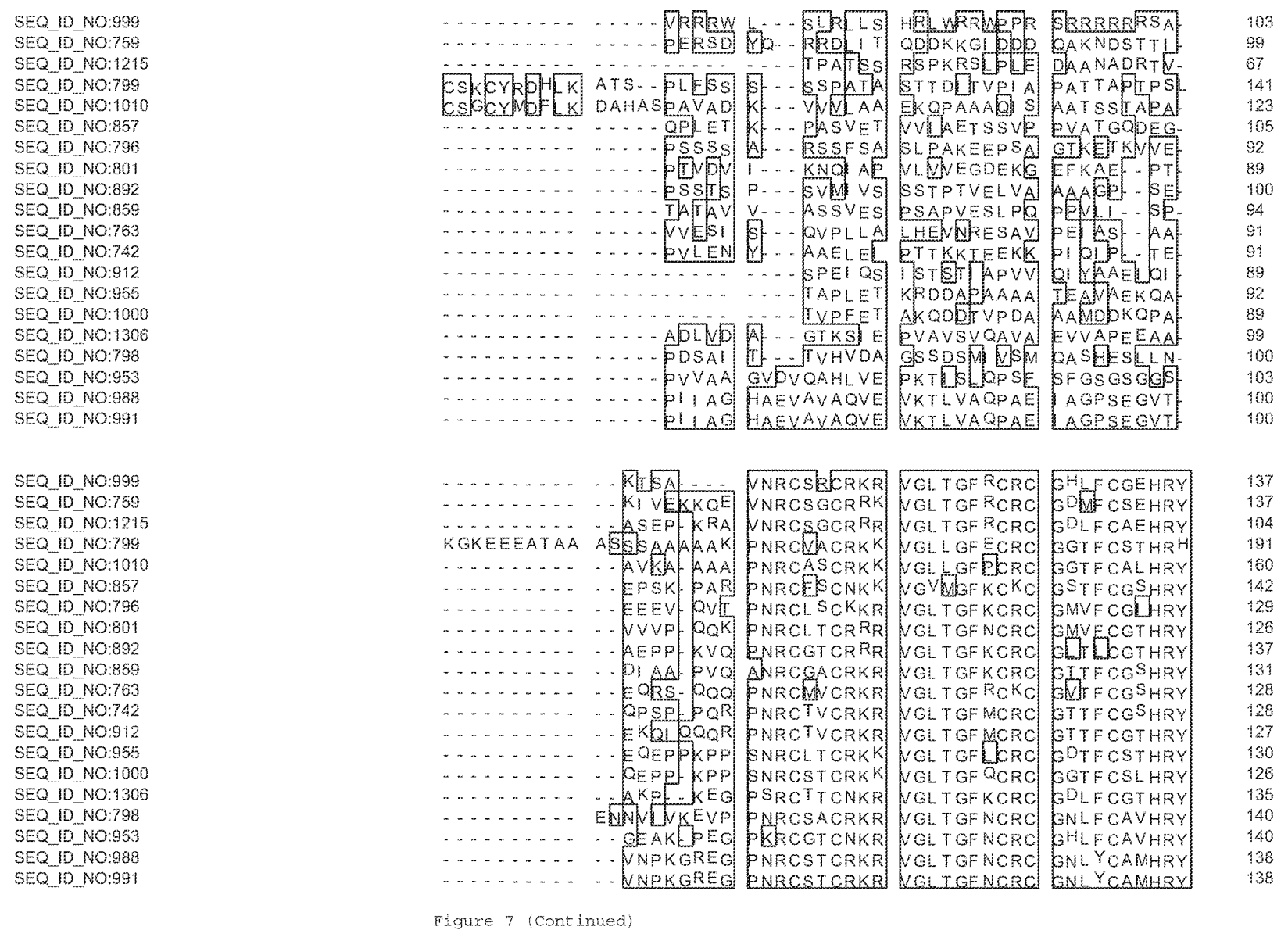

FIG. 7 is an alignment of Ceres SEEDLINE ID no. ME04477 (SEQ ID NO:742) with homologous and/or orthologous sequences, including, Ceres CLONE ID no. 1620215 (SEQ ID NO: 759); Public GI ID no. 38016527 (SEQ ID NO: 796); Ceres CLONE ID no. 1798756 (SEQ ID NO: 763); Public GI ID no. 75133829 (SEQ ID NO: 799); Ceres ANNOT ID no. 1460527 (SEQ ID NO: 801); Public GI ID no. 119720772 (SEQ ID NO: 857); Ceres CLONE ID no. 708446 (SEQ ID NO: 859); Public GI ID no. 92896423 (SEQ ID NO: 892); Ceres CLONE ID no. 1387149 (SEQ ID NO: 912); Public GI ID no. 5031281 (SEQ ID NO: 953); Ceres CLONE ID no. 1775820 (SEQ ID NO: 955); Public GI ID no. 35187687 (SEQ ID NO: 988); Public GI ID no. 115468934 (SEQ ID NO: 991); Public GI ID no. 118424243 (SEQ ID NO: 1000); Ceres ANNOT ID no. 6063957 (SEQ ID NO: 1010); CeresClone:1030374 (SEQ ID NO: 1306); Public GI ID no. 113196593 (SEQ ID NO: 798); Public GI ID no. 112819496 (SEQ ID NO: 999), and Public GI ID no. 169363 (SEQ ID NO: 1215).

Figure 8:
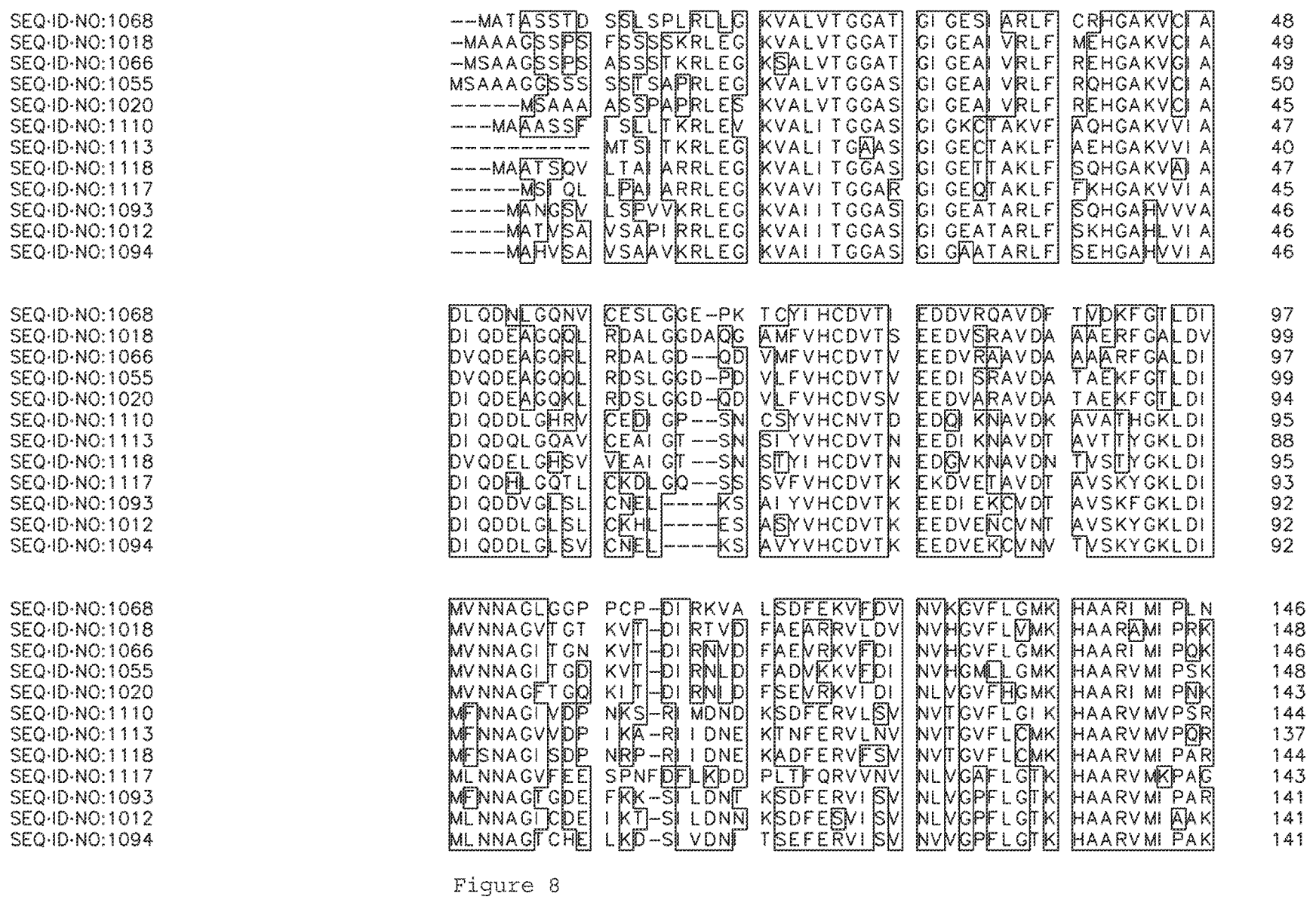
Figure 8:
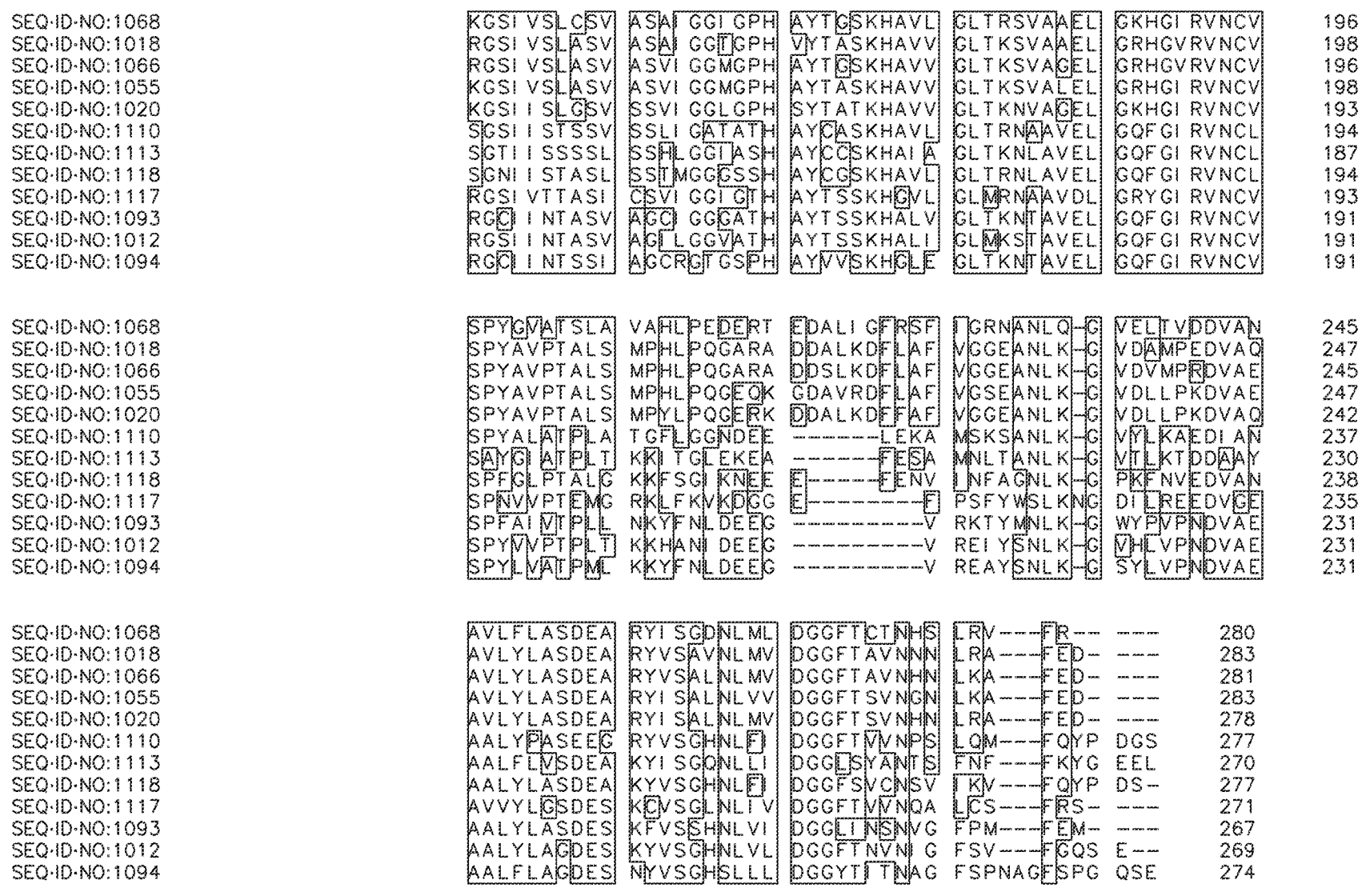

FIG. 8 is an alignment of Ceres SEEDLINE ID no. ME18396 (SEQ ID NO:1012) with homologous and/or orthologous sequences, including, Ceres CLONE ID no. 287430 (SEQ ID NO:1018), Ceres ANNOT ID no. 451889 (SEQ ID NO:1020), Ceres CLONE ID no. 936084 (SEQ ID NO:1055), Ceres CLONE ID no. 1792501 (SEQ ID NO:1066), Ceres ANNOT ID no. 1437875 (SEQ ID NO:1068), Public GI ID no. 1853968 (SEQ ID NO:1093), Public GI ID no. 27530032 (SEQ ID NO:1094), Ceres CLONE ID no. 1834483 (SEQ ID NO:1110), Public GI ID no. 84579418 (SEQ ID NO:1113), Public GI ID no. 15077030 (SEQ ID NO:1117), and Public GI ID no. 13752458 (SEQ ID NO:1118).

Figure 9:
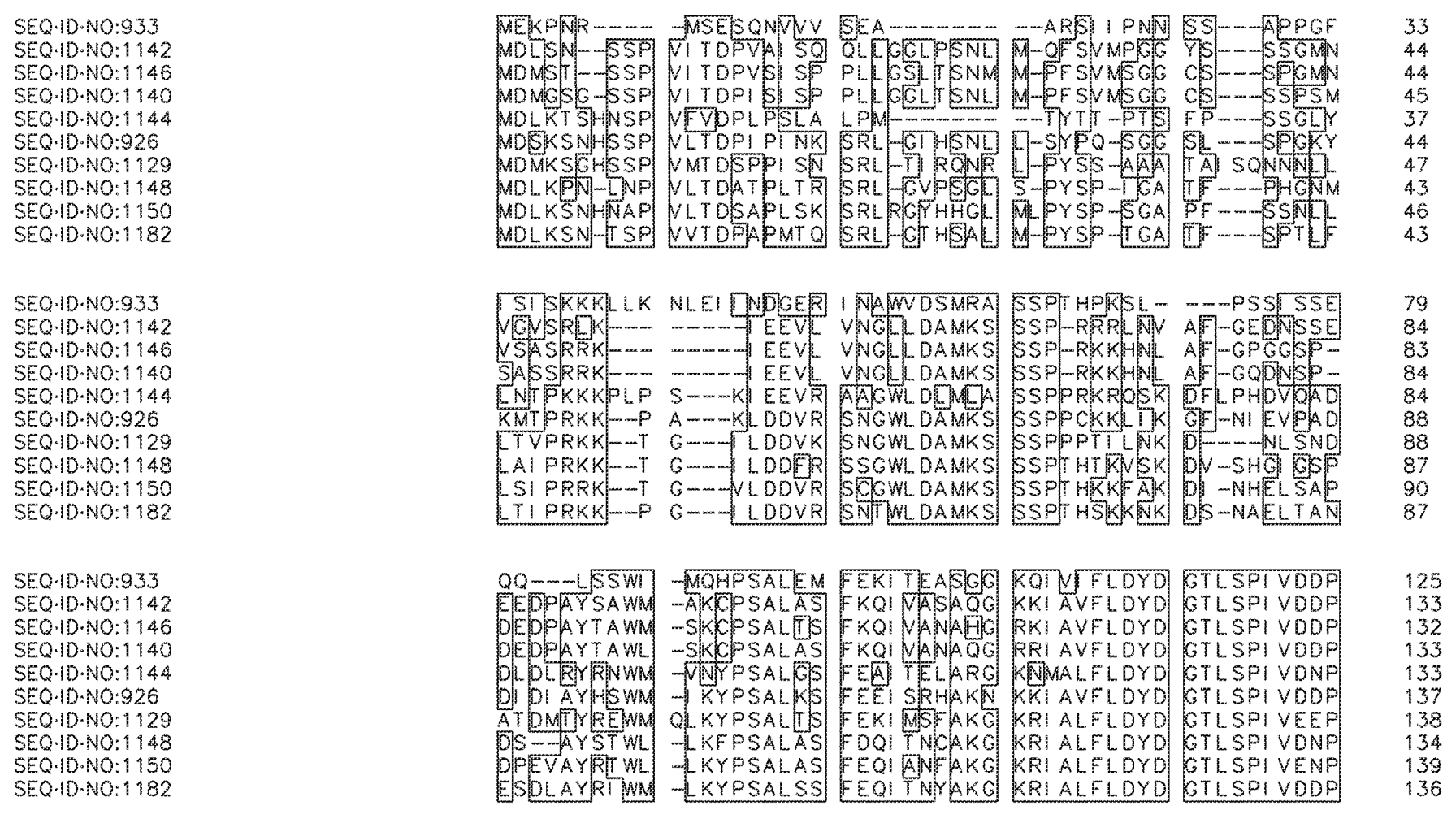

FIG. 9 is an alignment of Ceres SEEDLINE ID no. ME20095 (SEQ ID NO:1129) with homologous and/or orthologous sequences, including, Public GI ID no. 72255610 (SEQ ID NO:933), Ceres CLONE ID no. 1927040 (SEQ ID NO:926), Ceres CLONE ID no. 1562633 (SEQ ID NO:1140), Ceres ANNOT ID no. 1692728 (SEQ ID NO:1142), Ceres CLONE ID no. 921110 (SEQ ID NO:1144), Ceres CLONE ID no. 1791180 (SEQ ID NO:1146), Ceres CLONE ID no. 527891 (SEQ ID NO:1148), Ceres ANNOT ID no. 1522414 (SEQ ID NO:1150), and Public GI ID no. 51458330 (SEQ ID NO:1182).

FIG. 10 is an alignment of Ceres CLONE ID no. 31309 (SEQ ID NO:60) with homologous and/or orthologous sequences, including, Ceres CLONE ID no. 872030 (SEQ ID NO:62), Ceres CLONE ID no. 100029223 (SEQ ID NO:74), Ceres CLONE ID no. 1939845 (SEQ ID NO:98), Ceres CLONE ID no. 2015383 (SEQ ID NO:102), Ceres CLONE ID no. 1607893 (SEQ ID NO:104), Ceres CLONE ID no. 1075133 (SEQ ID NO:152), and Ceres CLONE ID no. 1218065 (SEQ ID NO:915).

Figure 11:
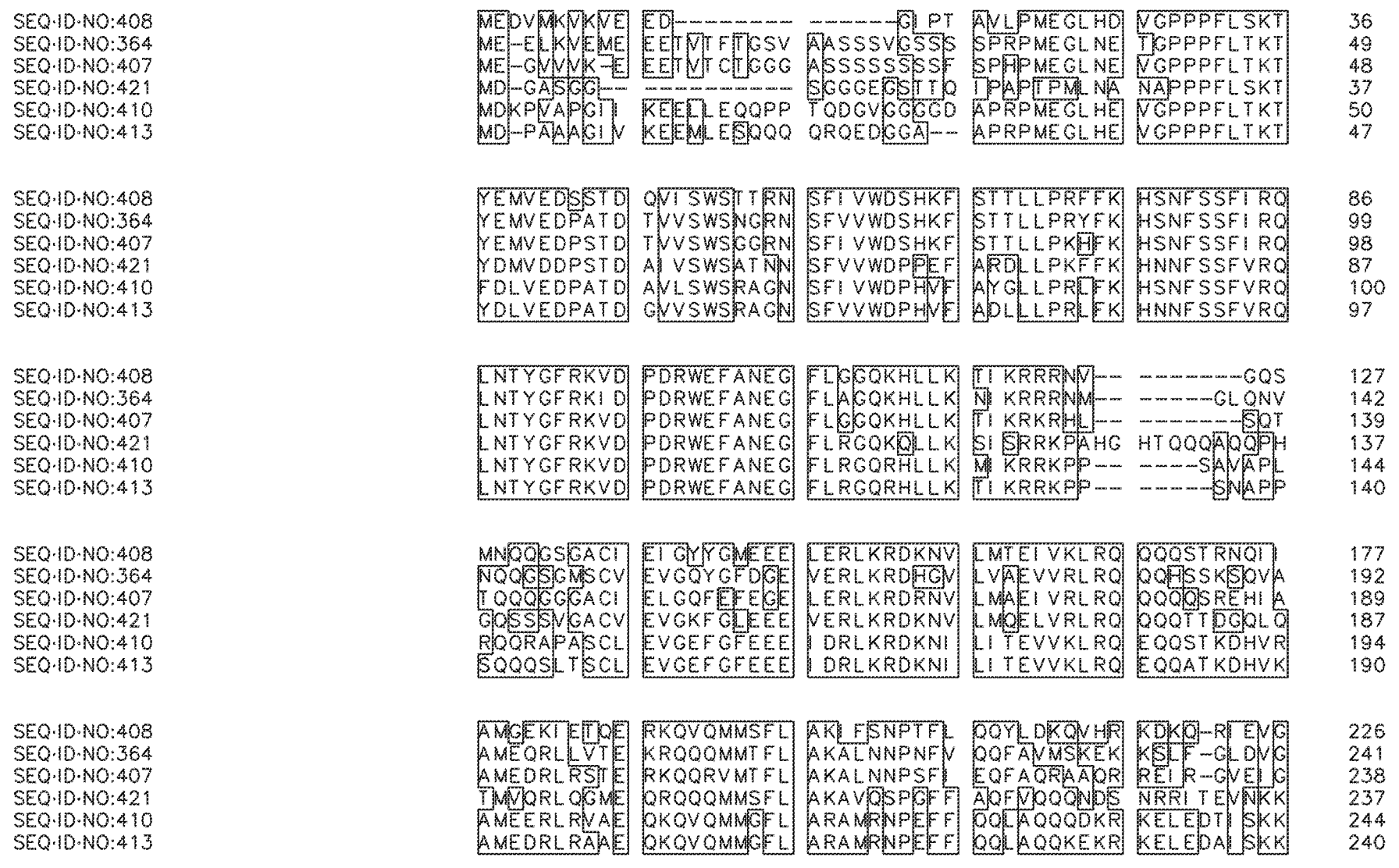
Figure 11:
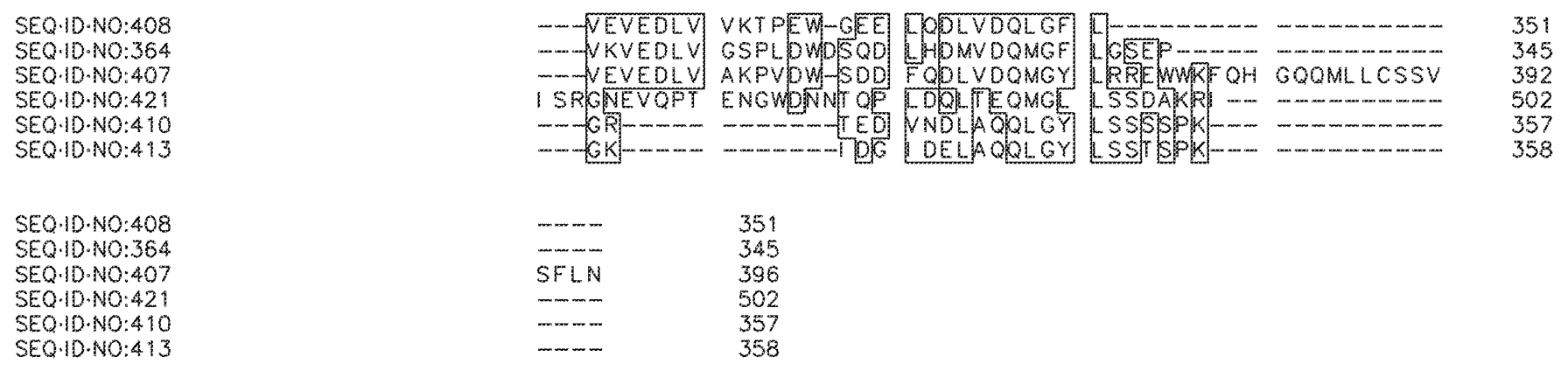

FIG. 11 is an alignment of Ceres LOCUS ID no. At2g26150 (SEQ ID NO:364) with homologous and/or orthologous sequences, including, Ceres ANNOT ID no. 1455221 (SEQ ID NO:407), Public GI ID no. 729774 (SEQ ID NO:408), Ceres CLONE ID no. 1414288 (SEQ ID NO:410), Public GI ID no. 115482048 (SEQ ID NO:413), and Public GI ID no. 56117815 (SEQ ID NO:421).

Figure 12:
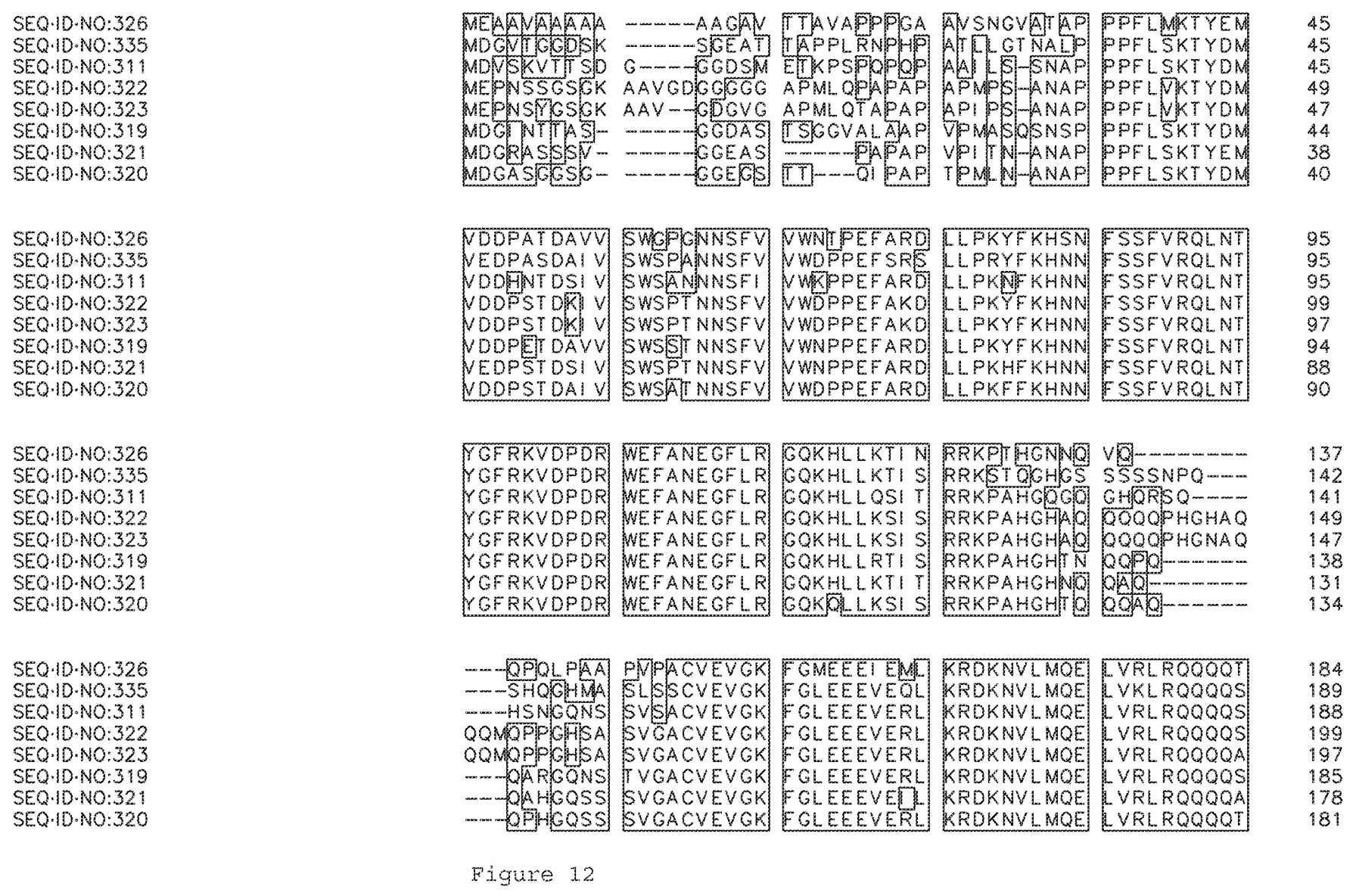
Figure 12:
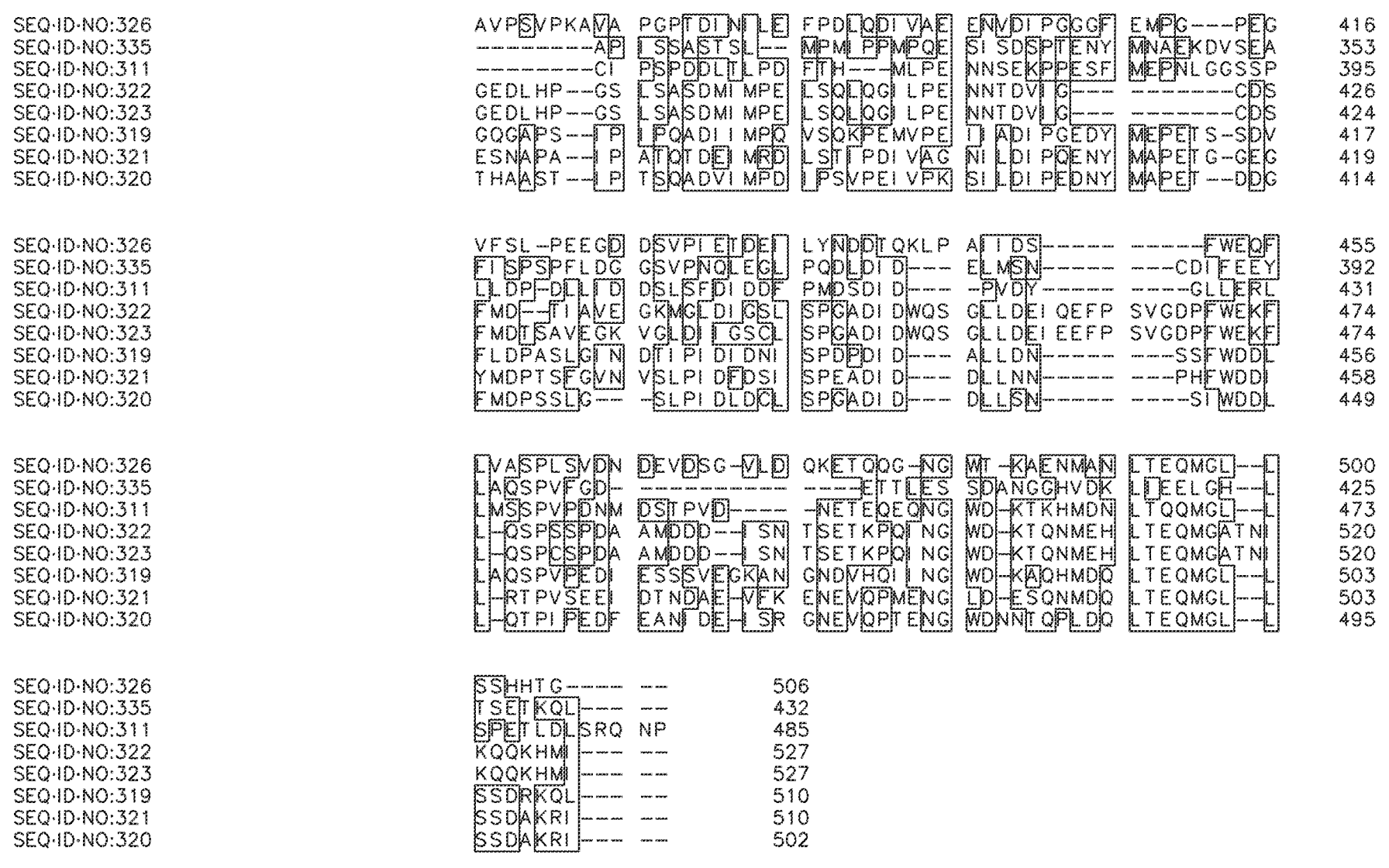

FIG. 12 is an alignment of Ceres LOCUS ID no. At1g32330 (SEQ ID NO:311) with homologous and/or orthologous sequences, including, Ceres ANNOT ID no. 1538958 (SEQ ID NO:319), Public GI ID no. 115521213 (SEQ ID NO:320), Public GI ID no. 42415865 (SEQ ID NO:321), Public GI ID no. 729775 (SEQ ID NO:322), Public GI ID no. 11386827 (SEQ ID NO:323), Public GI ID no. 115456675 (SEQ ID NO:326), and Public GI ID no. 89274218 (SEQ ID NO:335).

Figure 13:
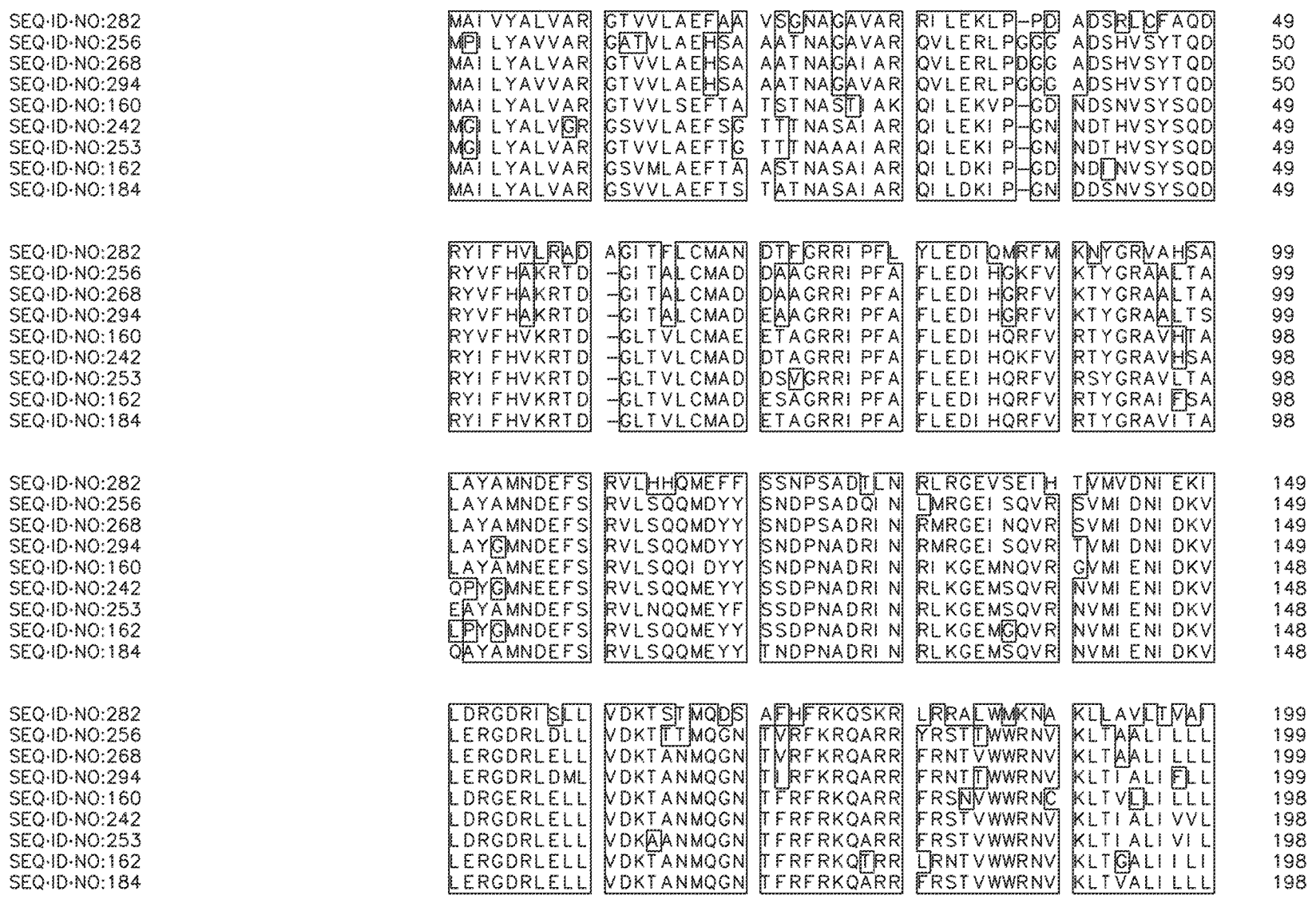

FIG. 13 is an alignment of Ceres CLONE ID no. 41543 (SEQ ID NO:160) with homologous and/or orthologous sequences, including, Ceres CLONE ID no. 1837065 (SEQ ID NO:162), Ceres ANNOT ID no. 1531178 (SEQ ID NO:184), Ceres CLONE ID no. 470694 (SEQ ID NO:242), Public GI ID no. 92867368 (SEQ ID NO:253), Ceres CLONE ID no. 859707 (SEQ ID NO:256), Ceres CLONE ID no. 392275 (SEQ ID NO:268), Ceres CLONE ID no. 1828394 (SEQ ID NO:282), and Public GI ID no. 115466694 (SEQ ID NO:294).

Figure 14:
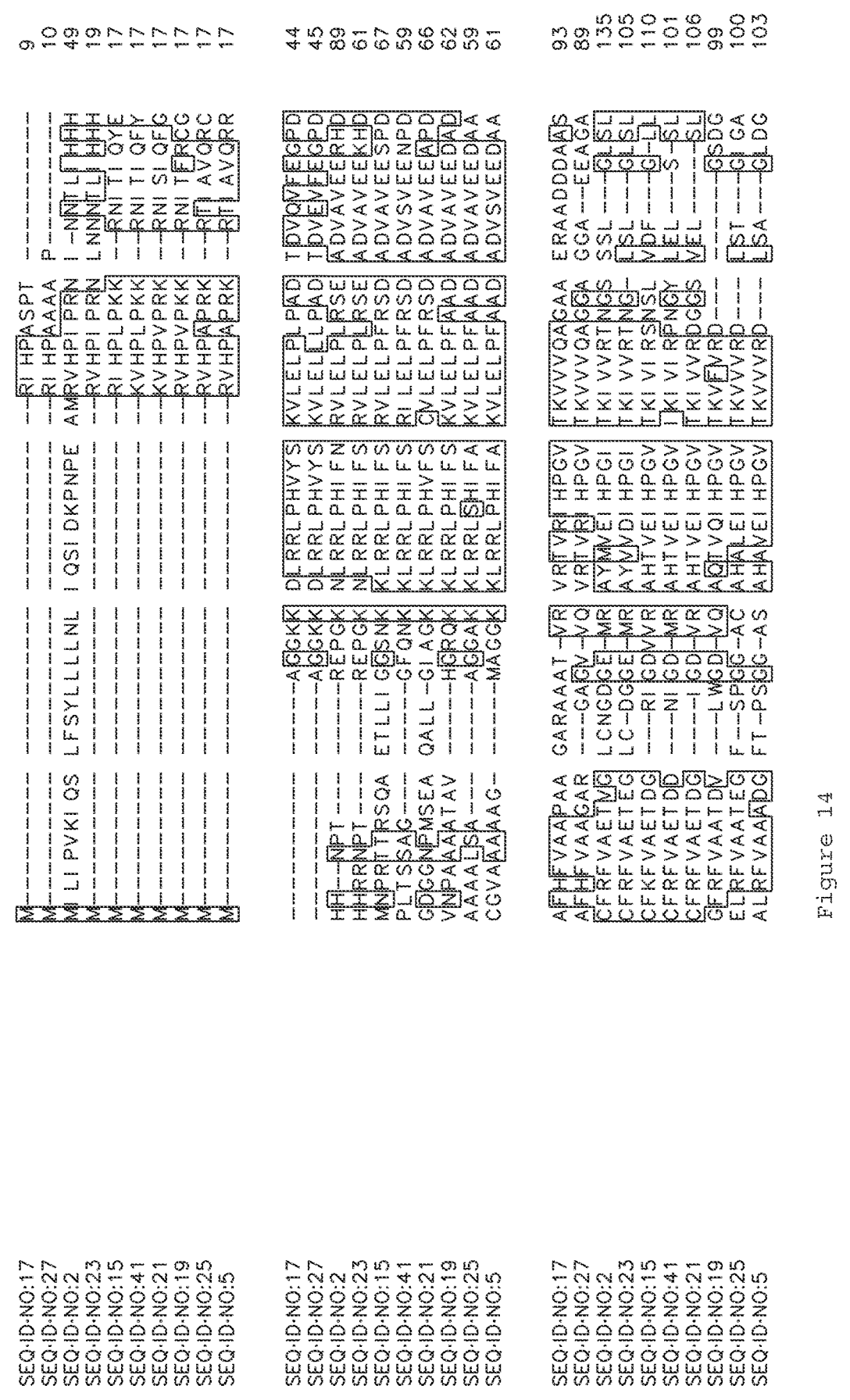
Figure 14:
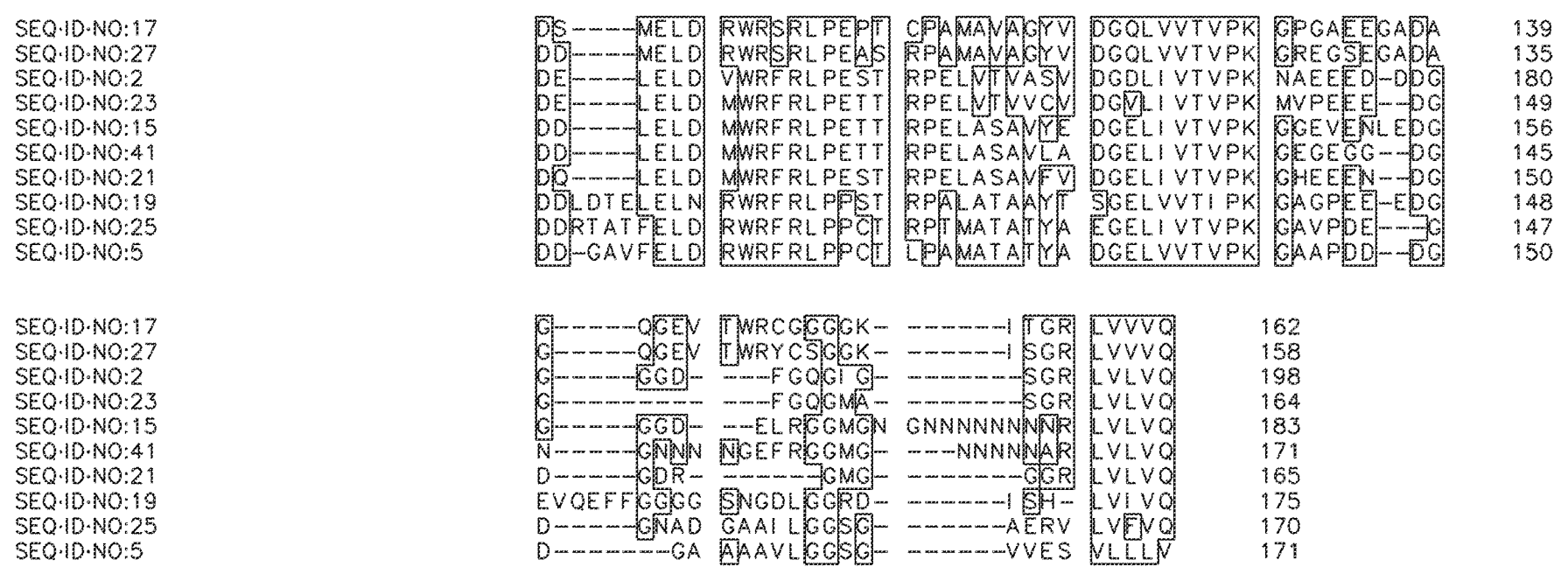

FIG. 14 is an alignment of Ceres CLONE ID no. 14572 (SEQ ID NO:2) with homologous and/or orthologous sequences, including, Public GI ID no. 115470807 (SEQ ID NO:5), Ceres CLONE ID no. 1842931 (SEQ ID NO:15), Ceres CLONE ID no. 321308 (SEQ ID NO:17), Ceres CLONE ID no. 1725811 (SEQ ID NO:19), Ceres CLONE ID no. 1357455 (SEQ ID NO:21), Ceres CLONE ID no. 943370 (SEQ ID NO:23), Ceres CLONE ID no. 1327712 (SEQ ID NO:25), Ceres CLONE ID no. 1764692 (SEQ ID NO:27), and Ceres ANNOT ID no. 1512656 (SEQ ID NO:41).

FIG. 15 is an alignment of Ceres SEEDLINE ID no. ME02401 (SEQ ID NO:749) with homologous and/or orthologous sequences, including, Ceres CLONE ID no. 1847516 (SEQ ID NO:1195), Ceres CLONE ID no. 1961986 (SEQ ID NO:1201), and Ceres ANNOT ID no. 6091930 (SEQ ID NO:1207).

FIG. 16 is an alignment of Ceres SEEDLINE ID no. ME004246 (SEQ ID NO:1311) with homologous and/or orthologous sequences, including, CeresClone:971761 (SEQ ID NO: 1313), CeresClone:1946574 (SEQ ID NO: 1331), CeresClone:2055551 (SEQ ID NO: 1340), CeresClone:100045499 (SEQ ID NO: 1347), CeresClone:1465853 (SEQ ID NO: 1353), and CeresClone:753982 (SEQ ID NO: 1360).

DETAILED DESCRIPTION

The invention features methods and materials related to increasing heat and/or drought tolerance in plants. In some embodiments, the plants may have increased heat and drought tolerance. The methods can include transforming a plant cell with a nucleic acid encoding a heat and/or drought-tolerance polypeptide, wherein expression of the polypeptide results in increased heat and/or drought tolerance. Plant cells produced using such methods can be grown to produce plants having an increased heat and/or drought tolerance. Such plants, and the seeds of such plants, may be used to produce, for example, may be used to produce biomass and/or to produce crops with increased yield and/or quality.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of tolerance to a stimulus (e.g., drought conditions or heat shock conditions) refers to the change in the level of tolerance of the indicated stimulus that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include heat and/or drought-tolerance polypeptides. Heat and/or drought-tolerance polypeptides can be effective to increase heat and/or drought-tolerance when expressed in a plant or plant cell. Such polypeptides typically contain at least one domain indicative of heat and/or drought-tolerance polypeptides, as described in more detail herein. Heat and/or drought-tolerance polypeptides typically have an HMM bit score that is greater than 20 for an HMM model based on one of the alignments set forth in FIGS. 1-16, as described in more detail herein. In some embodiments, heat and/or drought-tolerance polypeptides have greater than 80% identity to SEQ ID NO:442, SEQ ID NO:489, SEQ ID NO:568, SEQ ID NO:590, SEQ ID NO:705, SEQ ID NO:711, SEQ ID NO:742, SEQ ID NO:1012, SEQ ID NO:1129, SEQ ID NO:60, SEQ ID NO:364, SEQ ID NO:311, SEQ ID NO:160, SEQ ID NO:2, SEQ ID NO:749, SEQ ID NO:1311, or SEQ ID NO:57, as described in more detail herein.

A. Domains Indicative of Heat and/or Drought-Tolerance Polypeptides

A drought-tolerance polypeptide can be a RNA polymerase Rpb4 family member. The eukaryotic RNA polymerase subunit RPB4 forms a heterodimer with subunit RPB7 that reversibly associates with the RNA polymerase II core. SEQ ID NO:442 sets forth the amino acid sequence of an *Arabidopsis* clone, identified herein as Ceres SEEDLINE ID No. ME00029 (SEQ ID NO:441), that is predicted to encode a RNA polymerase Rpb4 polypeptide.

A drought-tolerance polypeptide can contain a sulfotransferase 1 domain characteristic of polypeptides belonging to the sulfotransferase family. Members of the sulfotransferase family catalyze the transfer of sulfate groups to specific compounds. SEQ ID NO:590, which sets forth the amino acid sequence of an *Arabidopsis* clone, identified herein as Ceres SEEDLINE ID No. ME02549 (SEQ ID NO:589), is predicted to encode a polypeptide containing a sulfotransferase 1 domain.

A drought-tolerance polypeptide can contain an AN1-like zinc finger (zf-AN1) and an A20-like zinc finger (zf-A20) domain. The AN1-like zinc finger domain was first identified as a zinc finger at the C-terminus of An1, a ubiquitin-like protein in *Xenopus laevis*. The AN1-like zinc finger domain is characterized by the pattern, C-X2-C-X(9-12)-C-X(1-2)-C-X4-C-X2-H-X5-H-X-C Where X can be any amino acid, and numbers in brackets indicate the number of residues. In A20, the A20-like zinc finger domain mediates self-association and IL-1-induced NF-kappa B activation. SEQ ID NO:742, which sets forth the amino acid sequence of an *Arabidopsis* clone, identified herein as Ceres Clone ID No. 24255 (SEQ ID NO:1241), is predicted to encode a polypeptide containing an AN1-like zinc finger domain and a A20-like zinc finger domain. SEQ ID NO:749, which sets forth the amino acid sequence of an *Arabidopsis* clone, identified herein as Ceres SEEDLINE ID No. ME02401, is also predicted to encode a polypeptide containing an AN1-like zinc finger domain and a A20-like zinc finger domain.

A drought-tolerance polypeptide can contain a short chain dehydrogenase (adh_short) domain. Most polypeptides containing a short chain dehydrogenase domain are polypeptides of about 250 to 300 amino acid residues, and are NAD- or NADP-dependent oxidoreductases. SEQ ID NO:1012, which sets forth the amino acid sequence of an *Arabidopsis* clone, identified herein as Ceres SEEDLINE ID No. 18396 (SEQ ID NO:1260), is predicted to encode a polypeptide containing a short chain dehydrogenase domain.

A drought-tolerance polypeptide can contain a trehalose-phosphatase (Trehalose_PPase) domain characteristic of trehalose phosphatase polypeptides. Trehalose phosphatases catalyse the de-phosphorylation of trehalose-6-phosphate to trehalose and orthophosphate. Trehalose is a common disaccharide in bacteria, fungi, and invertebrates that appears to play a role in desiccation tolerance. SEQ ID NO:1129, which sets forth the amino acid sequence of an *Arabidopsis* clone, identified herein as Ceres SEEDLINE ID No. ME20095 (SEQ ID NO:1126), is predicted to encode a polypeptide containing a trehalose-phosphatase domain.

A heat-tolerance polypeptide can be a synaptobrevin-related polypeptide. SEQ ID NO:160, which sets forth the amino acid sequence of an *Arabidopsis* clone, identified herein as Ceres CLONE ID no. 41543 (SEQ ID NO:159), is predicted to encode a synaptobrevin-related polypeptide.

A heat-tolerance polypeptide can contain an HSF-type DNA-binding domain, which is predicted to be characteristic of heat shock factor transcription activator. Heat shock factor transcription activators are often found associated with heat shock protein promoters during heat shock. SEQ ID NO:311, which sets forth the amino acid sequence of an *Arabidopsis* clone, identified herein as Ceres LOCUS ID no. At1g32330 (SEQ ID NO:310), is predicted to encode a polypeptide containing an HSF-type DNA-binding domain. SEQ ID NO:364, which sets forth the amino acid sequence of an *Arabidopsis* clone, identified herein as Ceres LOCUS ID no. At2g26150 (SEQ ID NO:363), is also predicted to encode a polypeptide containing an HSF-type DNA-binding domain.

A heat-tolerance polypeptide can contain a DnaJ domain. The prokaryotic heat shock protein DnaJ interacts with the chaperone hsp70-like DnaK protein. Structurally, the DnaJ protein consists of an N-terminal conserved domain (called 'J' domain) of about 70 amino acids, a glycine-rich region ('G' domain') of about 30 residues, a central domain containing four repeats of a CXXCXGXG motif ('CRR' domain) (SEQ ID NO:1364) and a C-terminal region of 120 to 170 residues. SEQ ID NO:60, which sets forth the amino acid sequence of an *Arabidopsis* clone, identified herein as Ceres CLONE ID no. 31309 (SEQ ID NO:58), is predicted to encode an polypeptide containing a DnaJ domain.

A drought-tolerance polypeptide can contain a KH_2 domain. Most polypeptides containing a KH_2 domain are typically around 70 amino acids and are present in a wide variety of quite diverse nucleic acid-binding proteins. It has been shown to bind RNA. Like many other RNA-binding motifs, KH motifs are found in one or multiple copies, each motif is necessary for in vitro RNA binding activity, suggesting that they may function cooperatively or, in the case of single KH motif proteins (for example, Mer1p), independently. According to structural analysis the KH domain can be separated in two groups. The first group or type-1 contain a beta-alpha-alpha-beta-beta-alpha structure, whereas in the type-2 the two last beta-sheet are located in the N terminal part of the domain (alpha-beta-beta-alpha-alpha-beta). Sequence similarity between these two folds are limited to a short region (VIGXXGXXI, SEQ ID NO:1365) in the RNA binding motif. This motif is located between helices 1 and 2 in type-1 and between helices 2 and 3 in type-2. SEQ ID NO:1311, which sets forth the amino acid sequence of an *Arabidopsis* clone, identified herein as Ceres SEEDLINE ID No. ME04246 (SEQ ID NO:1362), is predicted to encode a polypeptide containing a KH_2 domain.

B. Functional Homologs Identified by Reciprocal BLAST

In some embodiments, one or more functional homologs of a reference heat and/or drought-tolerance polypeptide defined by one or more of the Pfam descriptions indicated above are suitable for use as heat and/or drought-tolerance polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a heat and/or drought-tolerance polypeptide, or by combining domains from the coding sequences for different naturally-occurring heat and/or drought-tolerance polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of heat and/or drought-tolerance polypeptides. Sequence analysis can involve BLAST, Reciprocal BLAST, or PSI-BLAST analysis of nonredundant databases using a heat and/or drought-tolerance polypeptide amino acid sequence as the reference sequence. Amino acid sequence is, in some instances, deduced from the nucleotide sequence. Those polypeptides in the database that have greater than 40% sequence identity are candidates for further evaluation for suitability as a heat and/or drought-tolerance polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in heat and/or drought-tolerance polypeptides, e.g., conserved functional domains.

Conserved regions can be identified by locating a region within the primary amino acid sequence of a heat and/or drought-tolerance polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 20% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
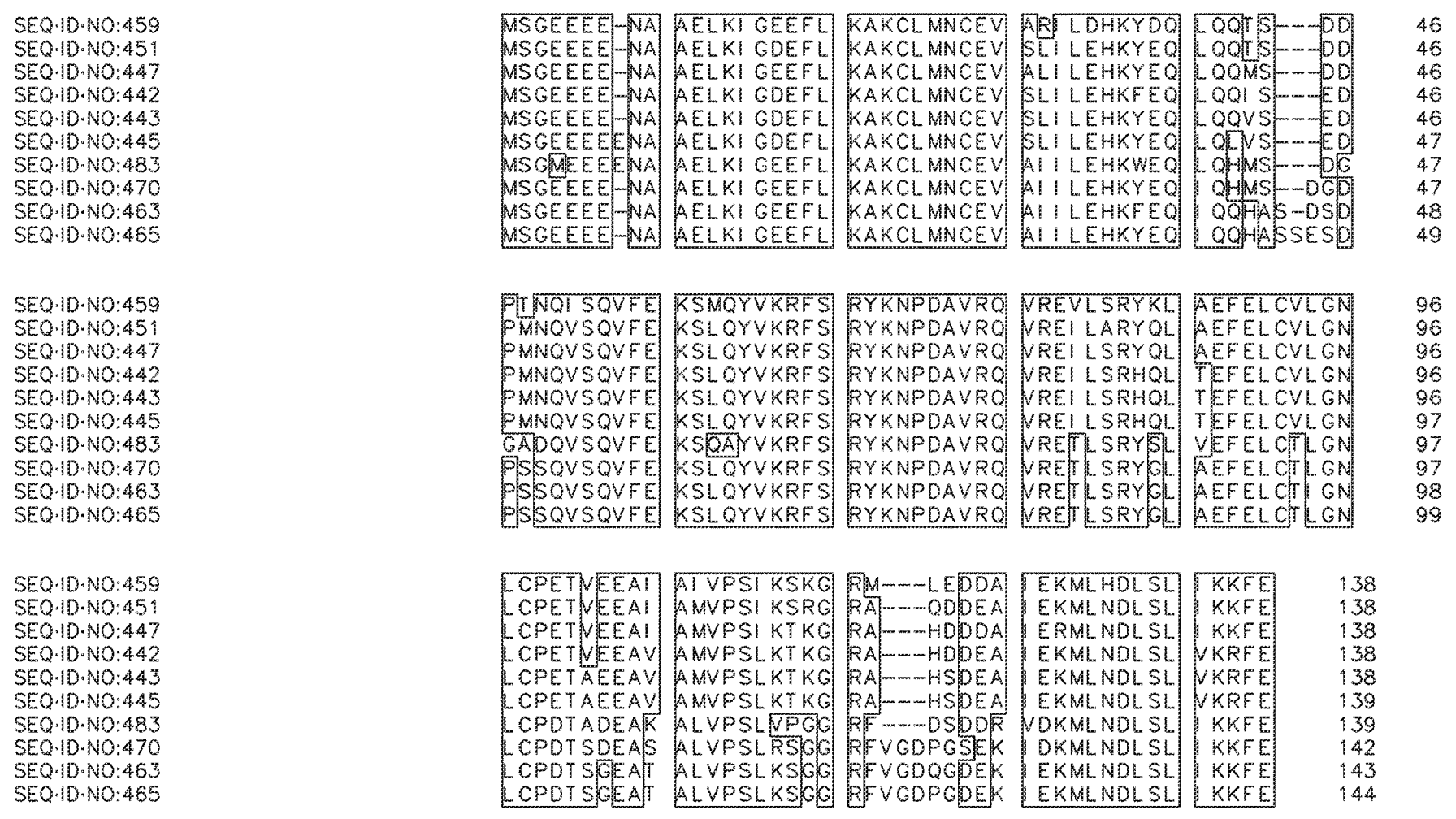

Examples of amino acid sequences of functional homologs of the polypeptide set forth in SEQ ID NO:442 are provided in FIG. 1 and in the sequence listing. Such functional homologs include Public GI ID no. 72384401 (SEQ ID NO:443), Ceres CLONE ID no. 1079382 (SEQ ID NO:445), Ceres CLONE ID no. 1853461 (SEQ ID NO:447), Ceres CLONE ID no. 1626485 (SEQ ID NO:451), Ceres CLONE ID no. 1713920 (SEQ ID NO:459), Ceres CLONE ID no. 1772747 (SEQ ID NO:463), Ceres CLONE ID no. 225960 (SEQ ID NO:465), Public GI ID no. 115443807 (SEQ ID NO:470), and Ceres CLONE ID no. 569388 (SEQ ID NO:483). Other functional homologs of SEQ ID NO:442 include Ceres CLONE ID no. 1915549 (SEQ ID NO:449), Ceres CLONE ID no. 529871 (SEQ ID NO:453), Ceres CLONE ID no. 1067079 (SEQ ID NO:455), Ceres CLONE ID no. 1079572 (SEQ ID NO:457), Ceres ANNOT ID no. 1456550 (SEQ ID NO:461), Ceres CLONE ID no. 1437889 (SEQ ID NO:469), Ceres CLONE ID no. 2014249 (SEQ ID NO:472), Ceres CLONE ID no. 2033133 (SEQ ID NO:474), Ceres CLONE ID no. 707404 (SEQ ID NO:476), Ceres CLONE ID no. 1770680 (SEQ ID NO:478), Ceres ANNOT ID no. 1450989 (SEQ ID NO:480), Public GI ID no. 72384445 (SEQ ID NO:481), Ceres CLONE ID no. 1059299 (SEQ ID NO:485), and Ceres ANNOT ID no. 6008086 (SEQ ID NO:487). In some cases, a functional homolog of SEQ ID NO:442 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:442.

Figure 2:
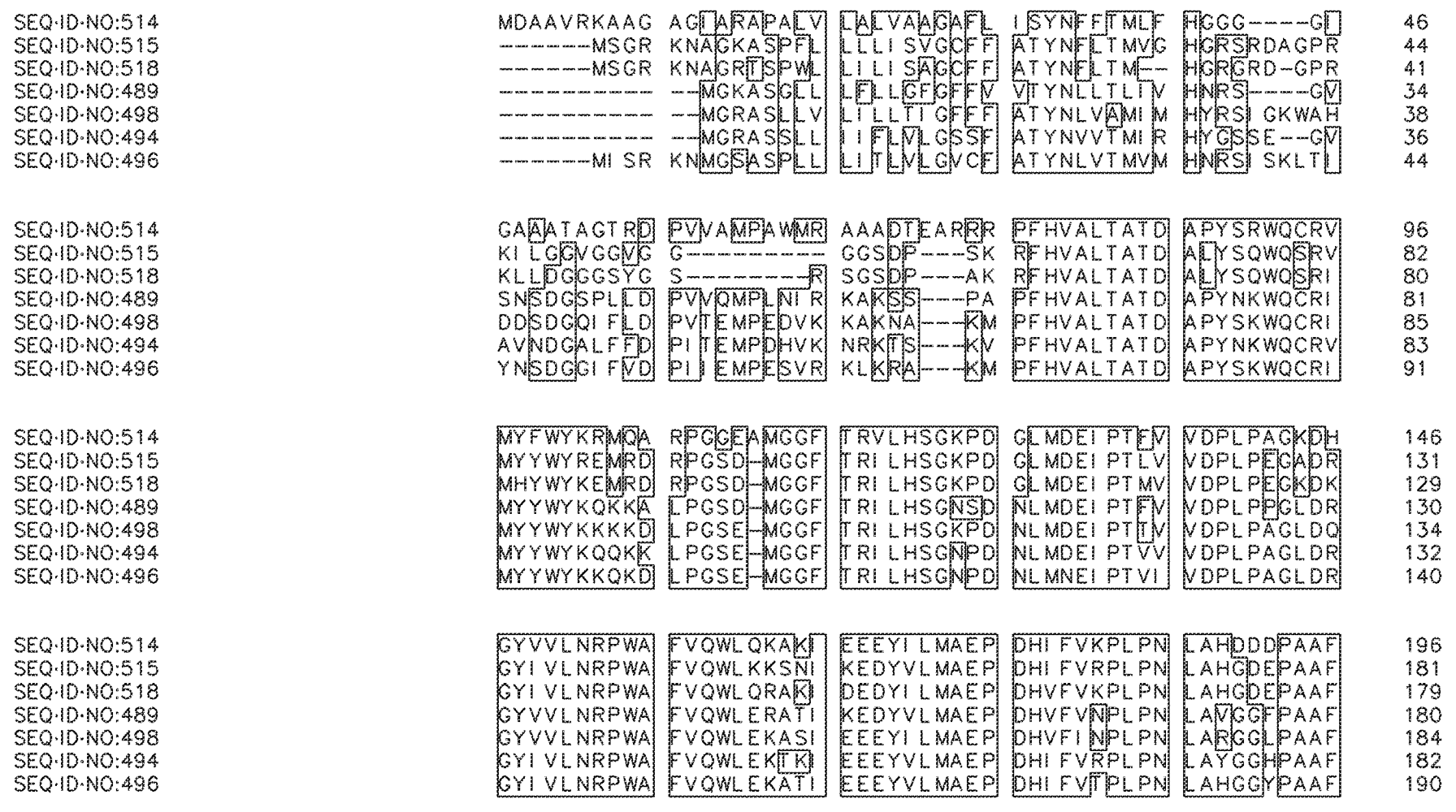
Figure 2:
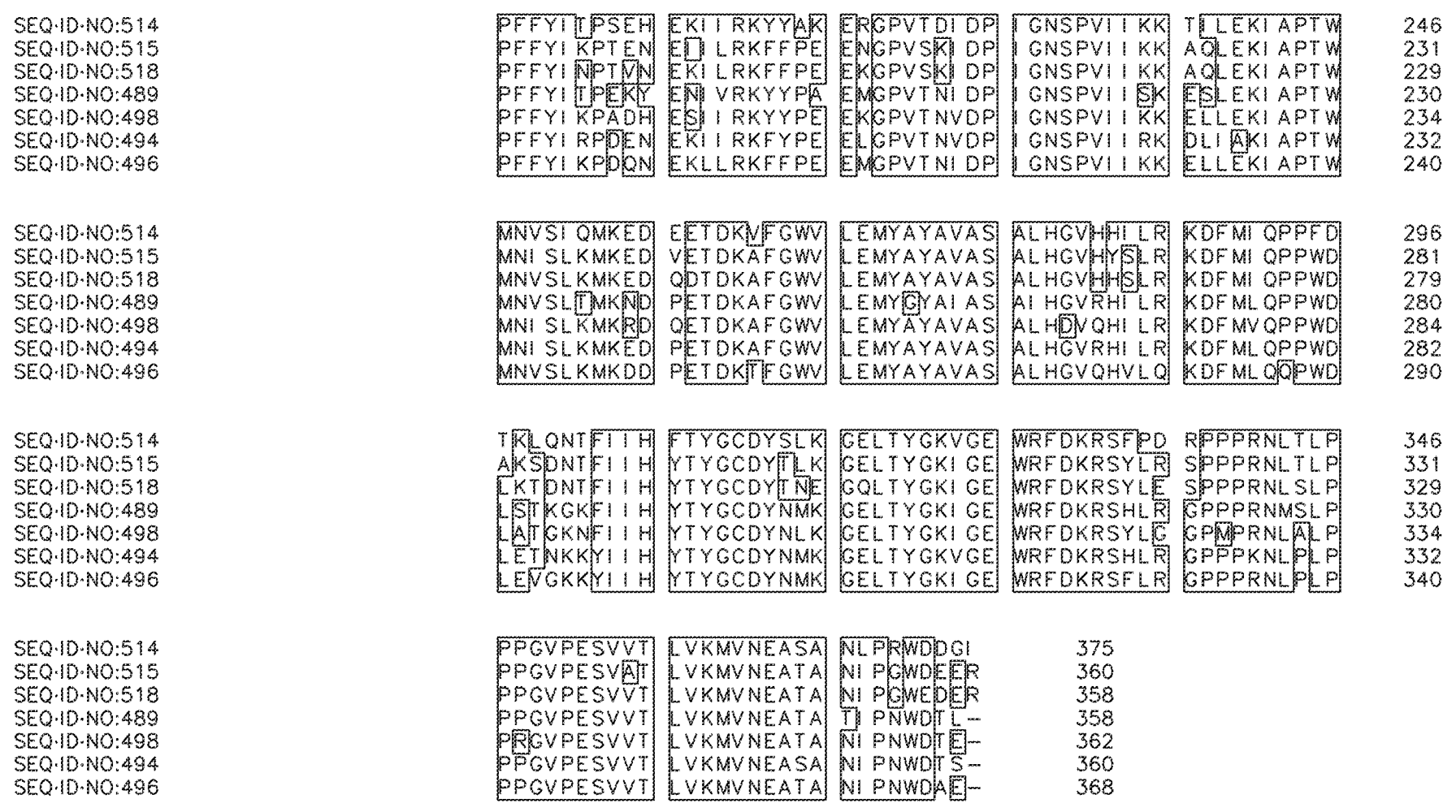

Examples of amino acid sequences of functional homologs of the polypeptide set forth in SEQ ID NO:489 are provided in FIG. 2 and in the sequence listing. Such functional homologs include Ceres CLONE ID no. 571200 (SEQ ID NO:494), Ceres CLONE ID no. 1928532 (SEQ ID NO:496), Ceres ANNOT ID no. 1490637 (SEQ ID NO:498), Ceres CLONE ID no. 295496 (SEQ ID NO:514), Public GI ID no. 115463637 (SEQ ID NO:515), and Ceres CLONE ID no. 1999444 (SEQ ID NO:518). Other functional homologs of SEQ ID NO:489 include Public GI ID no. 147844794 (SEQ ID NO:490), Public GI ID no. 147842279 (SEQ ID NO:491), Public GI ID no. 145355441 (SEQ ID NO:492), Ceres ANNOT ID no. 1461381 (SEQ ID NO:500), Ceres ANNOT ID no. 1440313 (SEQ ID NO:502), Ceres ANNOT ID no. 1448275 (SEQ ID NO:504), Ceres ANNOT ID no. 1437838 (SEQ ID NO:506), Ceres ANNOT ID no. 1501275 (SEQ ID NO:508), Ceres CLONE ID no. 1644562 (SEQ ID NO:510), Ceres CLONE ID no. 1925967 (SEQ ID NO:512), Public GI ID no. 115435904 (SEQ ID NO:516), Public GI ID no. 125552168 (SEQ ID NO:519), Public GI ID no. 125594093 (SEQ ID NO:520), Ceres CLONE ID no. 221188 (SEQ ID NO:522), Ceres ANNOT ID no. 1477714 (SEQ ID NO:524), Ceres CLONE ID no. 1787953 (SEQ ID NO:526), Ceres ANNOT ID no. 1531210 (SEQ ID NO:528), Ceres CLONE ID no. 521176 (SEQ ID NO:530), Public GI ID no. 22327055 (SEQ ID NO:531), Ceres ANNOT ID no. 1508824 (SEQ ID NO:533), Ceres CLONE ID no. 38879 (SEQ ID NO:535), Public GI ID no. 42569309 (SEQ ID NO:536), Ceres CLONE ID no. 1817784 (SEQ ID NO:538), Ceres CLONE ID no. 284637 (SEQ ID NO:540), Public GI ID no. 125596251 (SEQ ID NO:541), Public GI ID no. 125554300 (SEQ ID NO:543), Ceres CLONE ID no. 1935437 (SEQ ID NO:545), Ceres ANNOT ID no. 1455622 (SEQ ID NO:547), Public GI ID no. 55771354 (SEQ ID NO:548), Ceres ANNOT ID no. 1514655 (SEQ ID NO:550), Ceres CLONE ID no. 1848736 (SEQ ID NO:552), Public GI ID no. 125569872 (SEQ ID NO:553), Ceres CLONE ID no. 1645078 (SEQ ID NO:555), Ceres CLONE ID no. 1790573 (SEQ ID NO:557), Public GI ID no. 4567251 (SEQ ID NO:558), Ceres CLONE ID no. 444113 (SEQ ID NO:561), Public GI ID no. 125525355 (SEQ ID NO:562), Ceres ANNOT ID no. 6028854 (SEQ ID NO:564), and Ceres ANNOT ID no. 6115356 (SEQ ID NO:566). In some cases, a functional homolog of SEQ ID NO:489 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:489.

Examples of amino acid sequences of functional homologs of the polypeptide set forth in SEQ ID NO:568 are provided in FIG. 3 and in the sequence listing. Such functional homologs include Ceres CLONE ID no. 695006 (SEQ ID NO:578) and Ceres ANNOT ID no. 1527488 (SEQ ID NO:584). Other functional homologs of SEQ ID NO:568 include Public GI ID no. 79318519 (SEQ ID NO:569), Public GI ID no. 79318537 (SEQ ID NO:570), Ceres CLONE ID no. 956998 (SEQ ID NO:572), Ceres CLONE ID no. 978154 (SEQ ID NO:574), Ceres CLONE ID no. 1035628 (SEQ ID NO:576), Ceres CLONE ID no. 464169 (SEQ ID NO:580), Ceres ANNOT ID no. 1474075 (SEQ ID NO:582), Ceres ANNOT ID no. 1474073 (SEQ ID NO:586), and Ceres ANNOT ID no. 1527486 (SEQ ID NO:588). In some cases, a functional homolog of SEQ ID NO:568 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:568.

Figure 4:
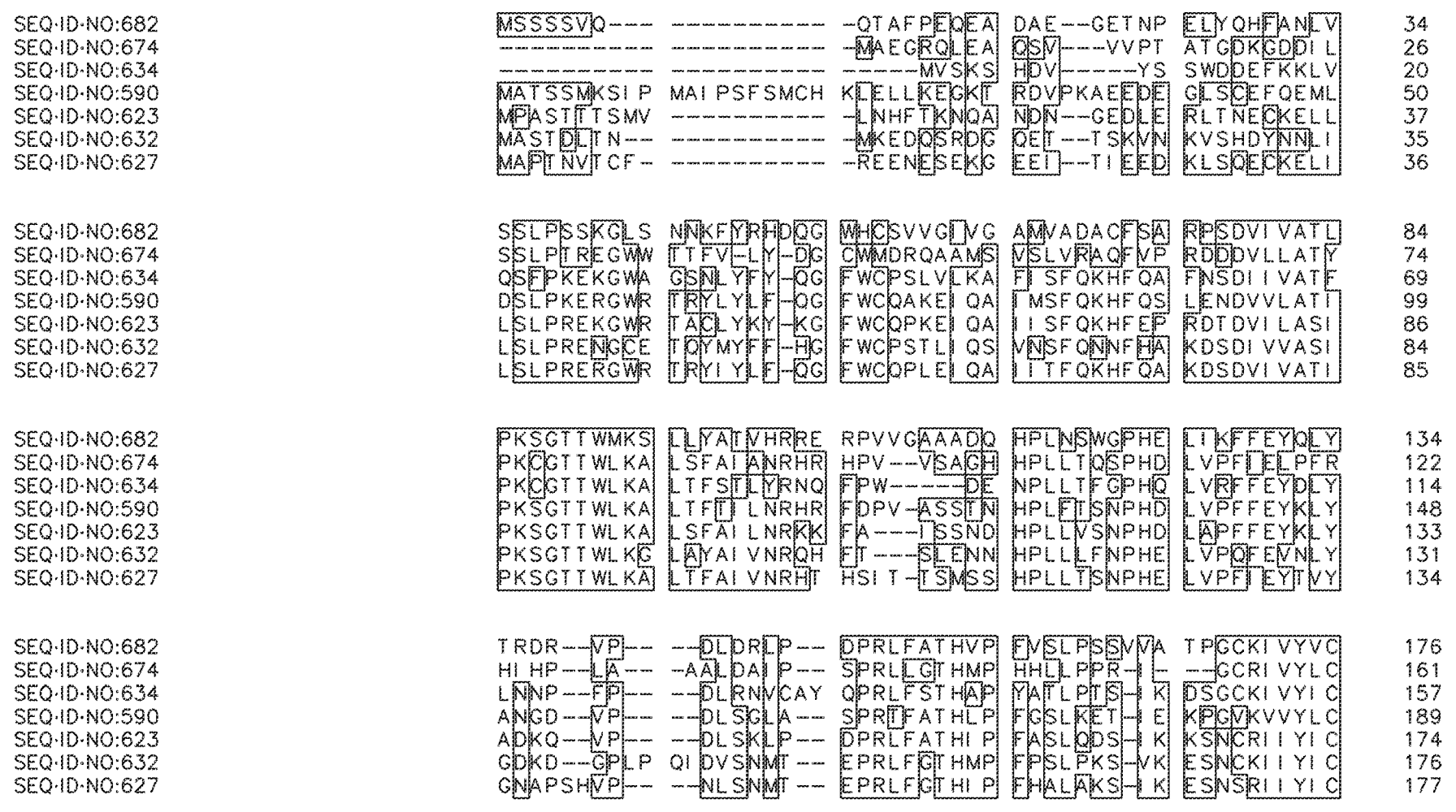
Figure 4:
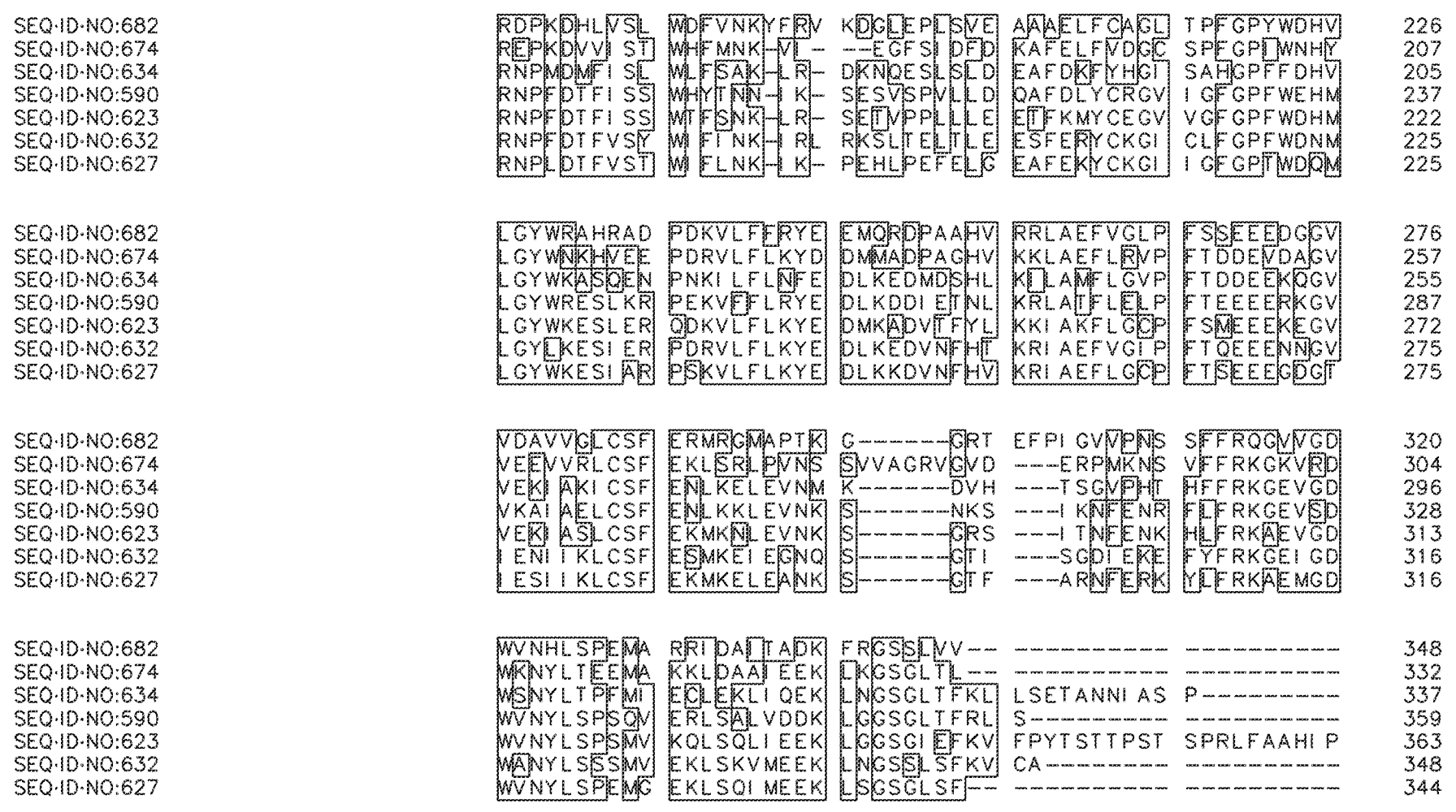

Examples of amino acid sequences of functional homologs of the polypeptide set forth in SEQ ID NO:590 are provided in FIG. 4 and in the sequence listing. Such functional homologs include Ceres ANNOT ID no. 1501305 (SEQ ID NO:623), Ceres CLONE ID no. 607280 (SEQ ID NO:627), Public GI ID no. 92887174 (SEQ ID NO:632), Ceres CLONE ID no. 1857162 (SEQ ID NO:634), Public GI ID no. 115477272 (SEQ ID NO:674), and Ceres CLONE ID no. 264002 (SEQ ID NO:682). Other functional homologs of SEQ ID NO:590 include Public GI ID no. 147822456 (SEQ ID NO:591), Public GI ID no. 144923935 (SEQ ID NO:592), Public GI ID no. 140038730 (SEQ ID NO:593), Public GI ID no. 78708014 (SEQ ID NO:594), Public GI ID no. 115481362 (SEQ ID NO:595), Public GI ID no. 125531350 (SEQ ID NO:596), Public GI ID no. 125525598 (SEQ ID NO:597), Public GI ID no. 77548630 (SEQ ID NO:598), Public GI ID no. 46798895 (SEQ ID NO:599), Public GI ID no. 125564653 (SEQ ID NO:600), Ceres CLONE ID no. 998865 (SEQ ID NO:602), Public GI ID no. 125556140 (SEQ ID NO:603), Public GI ID no. 125534482 (SEQ ID NO:604), Public GI ID no. 125550135 (SEQ ID NO:605), Ceres CLONE ID no. 639816 (SEQ ID NO:607), Public GI ID no. 125562170 (SEQ ID NO:608), Ceres CLONE ID no. 1797059 (SEQ ID NO:610), Ceres CLONE ID no. 1031510 (SEQ ID NO:612), Ceres CLONE ID no. 1973081 (SEQ ID NO:614), Public GI ID no. 125561002 (SEQ ID NO:615), Public GI ID no. 125541732 (SEQ ID NO:616), Public GI ID no. 125560677 (SEQ ID NO:617), Public GI ID no. 125559115 (SEQ ID NO:618), Public GI ID no. 15809903 (SEQ ID NO:619), Public GI ID no. 30681703 (SEQ ID NO:620), Public GI ID no. 9759556 (SEQ ID NO:621), Ceres ANNOT ID no. 1448303 (SEQ ID NO:625), Ceres ANNOT ID no. 1448305 (SEQ ID NO:629), Ceres ANNOT ID no. 1448307 (SEQ ID NO:631), Public GI ID no. 92888243 (SEQ ID NO:635), Public GI ID no. 92879395 (SEQ ID NO:636), Ceres CLONE ID no. 528876 (SEQ ID NO:638), Ceres ANNOT ID no. 1448352 (SEQ ID NO:640), Ceres ANNOT ID no. 1437745 (SEQ ID NO:642), Ceres ANNOT ID no. 1464146 (SEQ ID NO:644), Ceres ANNOT ID no. 1437744 (SEQ ID NO:646), Public GI ID no. 92894684 (SEQ ID NO:647), Ceres CLONE ID no. 3964 (SEQ ID NO:650), Public GI ID no. 13272389 (SEQ ID NO:651), Ceres ANNOT ID no. 1481203 (SEQ ID NO:653), Public GI ID no. 15227699 (SEQ ID NO:654), Public GI ID no. 92886084 (SEQ ID NO:655), Public GI ID no. 15239947 (SEQ ID NO:656), Ceres CLONE ID no. 34878 (SEQ ID NO:658), Ceres CLONE ID no. 150484 (SEQ ID NO:660), Public GI ID no. 21553545 (SEQ ID NO:661), Public GI ID no. 15222843 (SEQ ID NO:662), Public GI ID no. 38230552 (SEQ ID NO:663), Public GI ID no. 3420008 (SEQ ID NO:664), Public GI ID no. 15230602 (SEQ ID NO:665), Public GI ID no. 3420004 (SEQ ID NO:666), Public GI ID no. 2129586 (SEQ ID NO:667), Public GI ID no. 15217849 (SEQ ID NO:668), Public GI ID no. 15227704 (SEQ ID NO:669), Ceres ANNOT ID no. 1465750 (SEQ ID NO:671), Ceres CLONE ID no. 1983975 (SEQ ID NO:673), Public GI ID no. 15226028 (SEQ ID NO:675), Public GI ID no. 115459524 (SEQ ID NO:676), Ceres CLONE ID no. 1793353 (SEQ ID NO:678), Ceres ANNOT ID no. 1467399 (SEQ ID NO:680), Ceres CLONE ID no. 1982930 (SEQ ID NO:684), Public GI ID no. 125540700 (SEQ ID NO:685), Ceres ANNOT ID no. 1448743 (SEQ ID NO:687), Public GI ID no. 50251910 (SEQ ID NO:688), Ceres CLONE ID no. 1836748 (SEQ ID NO:690), Public GI ID no. 3420006 (SEQ ID NO:691), Public GI ID no. 92879376 (SEQ ID NO:692), Ceres CLONE ID no. 838941 (SEQ ID NO:694), Ceres ANNOT ID no. 1437746 (SEQ ID NO:696), Ceres ANNOT ID no. 6017241 (SEQ ID NO:698), Ceres ANNOT ID no. 6085947 (SEQ ID NO:700), and Ceres ANNOT ID no. 6017242 (SEQ ID NO:702). In some cases, a functional homolog of SEQ ID NO:590 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:590.

Examples of amino acid sequences of functional homologs of the polypeptide set forth in SEQ ID NO:705 are provided in FIG. 5 and in the sequence listing. Such functional homologs include Public GI ID no. 79320952 (SEQ ID NO:706) and Public GI ID no. 79320957 (SEQ ID NO:707). Other functional homologs of SEQ ID NO:705 include Public GI ID no. 6692094 (SEQ ID NO:708) and Public GI ID no. 145323049 (SEQ ID NO:709). In some cases, a functional homolog of SEQ ID NO:705 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:705.

Examples of amino acid sequences of functional homologs of the polypeptide set forth in SEQ ID NO:711 are provided in FIG. 6 and in the sequence listing. Such functional homologs include Ceres CLONE ID no. 964616 (SEQ ID NO:714), Ceres CLONE ID no. 100009667 (SEQ ID NO:715), Ceres ANNOT ID no. 1444568 (SEQ ID NO:719), Ceres CLONE ID no. 719489 (SEQ ID NO:725), Ceres CLONE ID no. 587748 (SEQ ID NO:733), Public GI ID no. 125528114 (SEQ ID NO:734), and Ceres CLONE ID no. 274172 (SEQ ID NO:737). Other functional homologs of SEQ ID NO:711 include Public GI ID no. 144923134 (SEQ ID NO:712), Ceres ANNOT ID no. 1471437 (SEQ ID NO:717), Ceres CLONE ID no. 1270484 (SEQ ID NO:721), Ceres CLONE ID no. 1075098 (SEQ ID NO:723), Public GI ID no. 18412211 (SEQ ID NO:727), Ceres CLONE ID no. 20358 (SEQ ID NO:729), Ceres CLONE ID no. 1915503 (SEQ ID NO:731), Public GI ID no. 115440619 (SEQ ID NO:735), Public GI ID no. 125572387 (SEQ ID NO:738), and Ceres ANNOT ID no. 6015812 (SEQ ID NO:740). In some cases, a functional homolog of SEQ ID NO:711 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:711.

Examples of amino acid sequences of functional homologs of the polypeptide set forth in SEQ ID NO:742 are provided in FIG. 7 and in the sequence listing. Such functional homologs include Public GI ID no. 147783026 (SEQ ID NO: 743), Public GI ID no. 119367488 (SEQ ID NO: 744), Public GI ID no. 147860340 (SEQ ID NO: 745), Public GI ID no. 115477170 (SEQ ID NO: 757), Ceres CLONE ID no. 1620215 (SEQ ID NO: 759), Ceres CLONE ID no. 1931889 (SEQ ID NO: 761), Ceres CLONE ID no. 1798756 (SEQ ID NO: 763), Ceres CLONE ID no. 1918424 (SEQ ID NO: 767), Ceres CLONE ID no. 1845154 (SEQ ID NO: 771), Public GI ID no. 38016527 (SEQ ID NO: 796), Ceres Clone ID no. 1084216 (SEQ ID NO: 797), Public GI ID no. 113196593 (SEQ ID NO: 798), Public GI ID no. 75133829 (SEQ ID NO: 799), Ceres ANNOT ID no. 1460527 (SEQ ID NO: 801), Ceres Annot ID no. 8644540 (SEQ ID NO: 805), Ceres ANNOT ID no. 1450673 (SEQ ID NO: 807), Public GI ID no. 116778802 (SEQ ID NO: 808), Public GI ID no. 116778893 (SEQ ID NO: 809), Public GI ID no. 116778998 (SEQ ID NO: 810), Public GI ID no. 157849766 (SEQ ID NO: 811), Public GI ID no. 159474166 (SEQ ID NO: 812), Public GI ID no. 168036656 (SEQ ID NO: 813), Ceres ANNOT ID no. 1456578 (SEQ ID NO: 815), Public GI ID no. 168053490 (SEQ ID NO: 816), Public GI ID no. 193237563 (SEQ ID NO: 817), Ceres Clone ID no. 100879386 (SEQ ID NO: 819), Ceres Clone ID no. 2055733 (SEQ ID NO: 823), Ceres Clone ID no. 2056478 (SEQ ID NO: 825), Ceres CLONE ID no. 13007 (SEQ ID NO: 832), Ceres CLONE ID no. 5522 (SEQ ID NO: 834), Ceres CLONE ID no. 30543 (SEQ ID NO: 836), Ceres CLONE ID no. 14203 (SEQ ID NO: 839), Ceres CLONE ID no. 975913 (SEQ ID NO: 846), Ceres CLONE ID no. 967417 (SEQ ID NO: 848), Public GI ID no. 119720772 (SEQ ID NO: 857), Ceres CLONE ID no. 708446 (SEQ ID NO: 859), Ceres CLONE ID no. 1614593 (SEQ ID NO: 863), Ceres CLONE ID no. 2025938 (SEQ ID NO: 885), Public GI ID no. 92896423 (SEQ ID NO: 892), Ceres CLONE ID no. 634261 (SEQ ID NO: 900), Ceres CLONE ID no. 1387149 (SEQ ID NO: 912), Ceres CLONE ID no. 1423851 (SEQ ID NO: 918), Ceres CLONE ID no. 1589047 (SEQ ID NO: 939), Ceres CLONE ID no. 1748922 (SEQ ID NO: 944), Public GI ID no. 5031281 (SEQ ID NO: 953), Ceres CLONE ID no. 1775820 (SEQ ID NO: 955), Ceres CLONE ID no. 1787151 (SEQ ID NO: 957), Ceres CLONE ID no. 1765871 (SEQ ID NO: 973), Ceres CLONE ID no. 1990071 (SEQ ID NO: 977), Public GI ID no. 35187687 (SEQ ID NO: 988), Public GI ID no. 125556051 (SEQ ID NO: 989), Public GI ID no. 125561658 (SEQ ID NO: 990), Public GI ID no. 115468934 (SEQ ID NO: 991), Public GI ID no. 115470773 (SEQ ID NO: 992), Public GI ID no. 115444813 (SEQ ID NO: 993), Public GI ID no. 112819496 (SEQ ID NO: 999), Public GI ID no. 118424243 (SEQ ID NO: 1000), Ceres ANNOT ID no. 6063957 (SEQ ID NO: 1010), Public GI ID no. 169363 (SEQ ID NO:1215), Ceres CLONE ID no. 24255 (SEQ ID NO: 1242), Ceres Clone ID no. 1030374 (SEQ ID NO: 1306), Ceres Clone ID no. 1738028 (SEQ ID NO: 1308), Public GI ID no. 115455855 (SEQ ID NO: 1309), and Public GI ID no. 193237563 (SEQ ID NO: 1310). In some cases, a functional homolog of SEQ ID NO:742 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:742.

Examples of amino acid sequences of functional homologs of the polypeptide set forth in SEQ ID NO:1012 are provided in FIG. 8 and in the sequence listing. Such functional homologs include Ceres CLONE ID no. 287430 (SEQ ID NO:1018), Ceres ANNOT ID no. 451889 (SEQ ID NO:1020), Ceres CLONE ID no. 936084 (SEQ ID NO:1055), Ceres CLONE ID no. 1792501 (SEQ ID NO:1066), Ceres ANNOT ID no. 1437875 (SEQ ID NO:1068), Public GI ID no. 1853968 (SEQ ID NO:1093), Public GI ID no. 27530032 (SEQ ID NO:1094), Ceres CLONE ID no. 1834483 (SEQ ID NO:1110), Public GI ID no. 84579418 (SEQ ID NO:1113), Public GI ID no. 15077030 (SEQ ID NO:1117), and Public GI ID no. 13752458 (SEQ ID NO:1118). Other functional homologs of SEQ ID NO:1012 include Public GI ID no. 147865685 (SEQ ID NO:1013), Public GI ID no. 119503368 (SEQ ID NO:1014), Public GI ID no. 72161874 (SEQ ID NO:1015), Public GI ID no. 91780661 (SEQ ID NO:1016), Ceres ANNOT ID no. 835908 (SEQ ID NO:1022), Public GI ID no. 38326750 (SEQ ID NO:1023), Ceres CLONE ID no. 1939396 (SEQ ID NO:1025), Ceres CLONE ID no. 403637 (SEQ ID NO:1027), Public GI ID no. 42539907 (SEQ ID NO:1028), Ceres CLONE ID no. 1836494 (SEQ ID NO:1030), Public GI ID no. 15192945 (SEQ ID NO:1031), Ceres CLONE ID no. 1607947 (SEQ ID NO:1033), Ceres CLONE ID no. 115880 (SEQ ID NO:1035), Ceres CLONE ID no. 1074009 (SEQ ID NO:1037), Ceres CLONE ID no. 476073 (SEQ ID NO:1039), Ceres CLONE ID no. 554053 (SEQ ID NO:1041), Ceres CLONE ID no. 391449 (SEQ ID NO:1045), Ceres CLONE ID no. 1846400 (SEQ ID NO:1048), Ceres ANNOT ID no. 1475185 (SEQ ID NO:1050), Public GI ID no. 115457148 (SEQ ID NO:1051), Ceres ANNOT ID no. 1454960 (SEQ ID NO:1053), Public GI ID no. 50346893 (SEQ ID NO:1056), Ceres CLONE ID no. 1931526 (SEQ ID NO:1058), Ceres ANNOT ID no. 1454260 (SEQ ID NO:1061), Public GI ID no. 115456131 (SEQ ID NO:1062), Ceres CLONE ID no. 159151 (SEQ ID NO:1064), Ceres CLONE ID no. 1842801 (SEQ ID NO:1071), Ceres CLONE ID no. 533030 (SEQ ID NO:1073), Ceres CLONE ID no. 1931881 (SEQ ID NO:1075), Ceres ANNOT ID no. 1480006 (SEQ ID NO:1077), Ceres CLONE ID no. 1895007 (SEQ ID NO:1079), Public GI ID no. 3598863 (SEQ ID NO:1080), Ceres ANNOT ID no. 1471735 (SEQ ID NO:1082), Ceres CLONE ID no. 1937530 (SEQ ID NO:1084), Ceres CLONE ID no. 1833050 (SEQ ID NO:1086), Ceres CLONE ID no. 644213 (SEQ ID NO:1088), Ceres CLONE ID no. 568154 (SEQ ID NO:1090), Ceres CLONE ID no. 527598 (SEQ ID NO:1092), Ceres ANNOT ID no. 1487614 (SEQ ID NO:1096), Ceres ANNOT ID no. 1541881 (SEQ ID NO:1098), Ceres ANNOT ID no. 1488465 (SEQ ID NO:1100), Ceres ANNOT ID no. 1488468 (SEQ ID NO:1102), Ceres ANNOT ID no. 1541884 (SEQ ID NO:1104), Ceres ANNOT ID no. 1454972 (SEQ ID NO:1106), Ceres ANNOT ID no. 1475186 (SEQ ID NO:1108), Ceres CLONE ID no. 686198 (SEQ ID NO:1112), Public GI ID no. 84579420 (SEQ ID NO:1114), Ceres CLONE ID no. 605144 (SEQ ID NO:1116), Public GI ID no. 15077028 (SEQ ID NO:1119), Ceres ANNOT ID no. 1454963 (SEQ ID NO:1121), Ceres ANNOT ID no. 6030208 (SEQ ID NO:1123), and Ceres ANNOT ID no. 6076767 (SEQ ID NO:1125). In some cases, a functional homolog of SEQ ID NO:1012 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1012.

Examples of amino acid sequences of functional homologs of the polypeptide set forth in SEQ ID NO:1129 are provided in FIG. 9 and in the sequence listing. Such functional homologs include Public GI ID no. 72255610 (SEQ ID NO:933), Ceres SEEDLINE ID no. ME20095 (SEQ ID NO:1129), Ceres CLONE ID no. 1562633 (SEQ ID NO:1140), Ceres ANNOT ID no. 1692728 (SEQ ID NO:1142), Ceres CLONE ID no. 921110 (SEQ ID NO:1144), Ceres CLONE ID no. 1791180 (SEQ ID NO:1146), Ceres CLONE ID no. 527891 (SEQ ID NO:1148), Ceres ANNOT ID no. 1522414 (SEQ ID NO:1150), and Public GI ID no. 51458330 (SEQ ID NO:1182). Other functional homologs of SEQ ID NO:1129 include Public GI ID no. 18399940 (SEQ ID NO:63), Ceres ANNOT ID no. 6107929 (SEQ ID NO:73), Ceres ANNOT ID no. 1473094 (SEQ ID NO:96), Ceres ANNOT ID no. 1503955 (SEQ ID NO:127), Ceres ANNOT ID no. 1526501 (SEQ ID NO:139), Public GI ID no. 15235713 (SEQ ID NO:179), Public GI ID no. 15234552 (SEQ ID NO:180), Ceres ANNOT ID no. 1520801 (SEQ ID NO:209), Ceres ANNOT ID no. 1443434 (SEQ ID NO:467), Public GI ID no. 30696058 (SEQ ID NO:559), Ceres ANNOT ID no. 1509601 (SEQ ID NO:648), Ceres ANNOT ID no. 1451912 (SEQ ID NO:726), Ceres ANNOT ID no. 6017545 (SEQ ID NO:741), Ceres ANNOT ID no. 1504999 (SEQ ID NO:765), Ceres ANNOT ID no. 1456402 (SEQ ID NO:773), Ceres ANNOT ID no. 1496359 (SEQ ID NO:781), Ceres ANNOT ID no. 1447260 (SEQ ID NO:842), Ceres ANNOT ID no. 1469023 (SEQ ID NO:861), Ceres ANNOT ID no. 1474186 (SEQ ID NO:865), Ceres ANNOT ID no. 1527596 (SEQ ID NO:867), Ceres CLONE ID no. 1919624 (SEQ ID NO:896), Ceres CLONE ID no. 677797 (SEQ ID NO:916), Public GI ID no. 7960729 (SEQ ID NO:932), Ceres CLONE ID no. 941845 (SEQ ID NO:1043), Public GI ID no. 30683008 (SEQ ID NO:1046), Public GI ID no. 42568786 (SEQ ID NO:1059), Ceres CLONE ID no. 255364 (SEQ ID NO:1069), Public GI ID no. 147771549 (SEQ ID NO:1130), Public GI ID no. 144924741 (SEQ ID NO:1131), Public GI ID no. 121594508 (SEQ ID NO:1132), Public GI ID no. 91202290 (SEQ ID NO:1133), Public GI ID no. 89900939 (SEQ ID NO:1134), Public GI ID no. 77917672 (SEQ ID NO:1135), Public GI ID no. 77165252 (SEQ ID NO:1136), Public GI ID no. 115375374 (SEQ ID NO:1137), Public GI ID no. 110602449 (SEQ ID NO:1138), Public GI ID no. 125540573 (SEQ ID NO:1151), Public GI ID no. 125561519 (SEQ ID NO:1152), Public GI ID no. 125528345 (SEQ ID NO:1153), Public GI ID no. 116310408 (SEQ ID NO:1154), Public GI ID no. 115483332 (SEQ ID NO:1156), Public GI ID no. 125575640 (SEQ ID NO:1157), Public GI ID no. 115476368 (SEQ ID NO:1158), Public GI ID no. 115478841 (SEQ ID NO:1159), Public GI ID no. 115467158 (SEQ ID NO:1160), Public GI ID no. 72384477 (SEQ ID NO:1161), Public GI ID no. 116054703 (SEQ ID NO:1162), Ceres CLONE ID no. 1786317 (SEQ ID NO:1164), Ceres CLONE ID no. 1791336 (SEQ ID NO:1166), Ceres CLONE ID no. 1877752 (SEQ ID NO:1168), Ceres CLONE ID no. 1821191 (SEQ ID NO:1170), Ceres CLONE ID no. 446838 (SEQ ID NO:1172), Ceres CLONE ID no. 1556915 (SEQ ID NO:1174), Public GI ID no. 90200725 (SEQ ID NO:1175), Ceres CLONE ID no. 1580247 (SEQ ID NO:1177), Ceres CLONE ID no. 644201 (SEQ ID NO:1179), Ceres CLONE ID no. 538689 (SEQ ID NO:1181), Ceres CLONE ID no. 817225 (SEQ ID NO:1184), and Ceres CLONE ID no. 923842 (SEQ ID NO:1186). In some cases, a functional homolog of SEQ ID NO:1129 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1129.

Examples of amino acid sequences of functional homologs of the polypeptide set forth in SEQ ID NO:60 are provided in FIG. 10 and in the sequence listing. Such functional homologs include Ceres CLONE ID no. 872030 (SEQ ID NO:62), Ceres CLONE ID no. 100029223 (SEQ ID NO:74), Ceres CLONE ID no. 1939845 (SEQ ID NO:98), Ceres CLONE ID no. 2015383 (SEQ ID NO:102), Ceres CLONE ID no. 1607893 (SEQ ID NO:104), Ceres CLONE ID no. 1075133 (SEQ ID NO:152), and Ceres CLONE ID no. 1218065 (SEQ ID NO:915). Other functional homologs of SEQ ID NO:60 include Public GI ID no. 15227919 (SEQ ID NO:64), Public GI ID no. 9843641 (SEQ ID NO:65), Public GI ID no. 124294789 (SEQ ID NO:66), Public GI ID no. 15233446 (SEQ ID NO:67), Public GI ID no. 115477679 (SEQ ID NO:68), Public GI ID no. 42407552 (SEQ ID NO:69), Public GI ID no. 125562450 (SEQ ID NO:70), Public GI ID no. 115469980 (SEQ ID NO:71), Ceres ANNOT ID no. 1442539 (SEQ ID NO:76), Ceres ANNOT ID no. 1442538 (SEQ ID NO:78), Ceres ANNOT ID no. 1460661 (SEQ ID NO:80), Ceres ANNOT ID no. 1452884 (SEQ ID NO:82), Ceres ANNOT ID no. 1450523 (SEQ ID NO:84), Ceres ANNOT ID no. 1442257 (SEQ ID NO:86), Ceres ANNOT ID no. 1541121 (SEQ ID NO:88), Ceres ANNOT ID no. 1480481 (SEQ ID NO:90), Ceres ANNOT ID no. 1487713 (SEQ ID NO:92), Ceres ANNOT ID no. 1456204 (SEQ ID NO:94), Ceres CLONE ID no. 1387402 (SEQ ID NO:100), Ceres CLONE ID no. 972919 (SEQ ID NO:106), Ceres CLONE ID no. 1645860 (SEQ ID NO:108), Ceres CLONE ID no. 1042804 (SEQ ID NO:110), Ceres CLONE ID no. 1606678 (SEQ ID NO:112), Ceres CLONE ID no. 684496 (SEQ ID NO:114), Ceres CLONE ID no. 1062366 (SEQ ID NO:116), Ceres CLONE ID no. 1722931 (SEQ ID NO:118), Ceres CLONE ID no. 746169 (SEQ ID NO:120), Ceres CLONE ID no. 1050475 (SEQ ID NO:122), Ceres CLONE ID no. 1728904 (SEQ ID NO:124), Ceres CLONE ID no. 1698538 (SEQ ID NO:126), Ceres CLONE ID no. 1762328 (SEQ ID NO:130), Ceres CLONE ID no. 1590072 (SEQ ID NO:132), Ceres CLONE ID no. 471593 (SEQ ID NO:134), Ceres CLONE ID no. 1031667 (SEQ ID NO:136), Ceres CLONE ID no. 1826085 (SEQ ID NO:138), Ceres CLONE ID no. 373932 (SEQ ID NO:142), Ceres CLONE ID no. 1797836 (SEQ ID NO:144), Ceres CLONE ID no. 1102774 (SEQ ID NO:146), Ceres CLONE ID no. 842287 (SEQ ID NO:148), Ceres CLONE ID no. 568205 (SEQ ID NO:150), Ceres ANNOT ID no. 6108997 (SEQ ID NO:154), Ceres ANNOT ID no. 6023609 (SEQ ID NO:156), and Ceres ANNOT ID no. 6017906 (SEQ ID NO:158). In some cases, a functional homolog of SEQ ID NO:60 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:60.

Examples of amino acid sequences of functional homologs of the polypeptide set forth in SEQ ID NO:364 are provided in FIG. 11 and in the sequence listing. Such functional homologs include Ceres ANNOT ID no. 1455221 (SEQ ID NO:407), Public GI ID no. 729774 (SEQ ID NO:408), Ceres CLONE ID no. 1414288 (SEQ ID NO:410), Public GI ID no. 115482048 (SEQ ID NO:413), and Public GI ID no. 56117815 (SEQ ID NO:421). Other functional homologs of SEQ ID NO:364 include Ceres ANNOT ID no. 1485538 (SEQ ID NO:366), Ceres ANNOT ID no. 1538505 (SEQ ID NO:368), Public GI ID no. 8347238 (SEQ ID NO:369), Public GI ID no. 125542955 (SEQ ID NO:370), Public GI ID no. 115446219 (SEQ ID NO:371), Ceres CLONE ID no. 1597127 (SEQ ID NO:373), Ceres CLONE ID no. 1584568 (SEQ ID NO:375), Ceres CLONE ID no. 286056 (SEQ ID NO:377), Ceres ANNOT ID no. 1543432 (SEQ ID NO:379), Ceres CLONE ID no. 1728062 (SEQ ID NO:381), Ceres ANNOT ID no. 1448950 (SEQ ID NO:383), Ceres CLONE ID no. 771500 (SEQ ID NO:385), Ceres ANNOT ID no. 1485096 (SEQ ID NO:387), Ceres CLONE ID no. 1646104 (SEQ ID NO:389), Public GI ID no. 111184724 (SEQ ID NO:390), Ceres CLONE ID no. 1362475 (SEQ ID NO:392), Ceres CLONE ID no. 597906 (SEQ ID NO:394), Ceres CLONE ID no. 615781 (SEQ ID NO:396), Ceres CLONE ID no. 538713 (SEQ ID NO:398), Ceres CLONE ID no. 1794141 (SEQ ID NO:400), Public GI ID no. 5821138 (SEQ ID NO:401), Public GI ID no. 886742 (SEQ ID NO:402), Ceres CLONE ID no. 1814498 (SEQ ID NO:404), Public GI ID no. 7158882 (SEQ ID NO:405), Ceres ANNOT ID no. 1452564 (SEQ ID NO:412), Public GI ID no. 125557431 (SEQ ID NO:414), Ceres ANNOT ID no. 1442880 (SEQ ID NO:416), Ceres ANNOT ID no. 1463437 (SEQ ID NO:418), Public GI ID no. 42415865 (SEQ ID NO:419), Public GI ID no. 33087081 (SEQ ID NO:420), Public GI ID no. 115521217 (SEQ ID NO:422), Public GI ID no. 115521211 (SEQ ID NO:423), Public GI ID no. 115521215 (SEQ ID NO:424), Ceres ANNOT ID no. 1454376 (SEQ ID NO:426), Ceres CLONE ID no. 835571 (SEQ ID NO:428), Ceres ANNOT ID no. 1500046 (SEQ ID NO:430), Public GI ID no. 110738569 (SEQ ID NO:431), Public GI ID no. 125542510 (SEQ ID NO:432), Public GI ID no. 30686034 (SEQ ID NO:433), Public GI ID no. 125570883 (SEQ ID NO:434), Public GI ID no. 42562463 (SEQ ID NO:435), Ceres CLONE ID no. 100043265 (SEQ ID NO:436), Ceres ANNOT ID no. 6089790 (SEQ ID NO:438), and Ceres ANNOT ID no. 6043635 (SEQ ID NO:440). In some cases, a functional homolog of SEQ ID NO:364 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:364.

Examples of amino acid sequences of functional homologs of the polypeptide set forth in SEQ ID NO:311 are provided in FIG. 12 and in the sequence listing. Such functional homologs include Ceres ANNOT ID no. 1538958 (SEQ ID NO:319), Public GI ID no. 115521213 (SEQ ID NO:320), Public GI ID no. 42415865 (SEQ ID NO:321), Public GI ID no. 729775 (SEQ ID NO:322), Public GI ID no. 11386827 (SEQ ID NO:323), Public GI ID no. 115456675 (SEQ ID NO:326), and Public GI ID no. 89274218 (SEQ ID NO:335). Other functional homologs of SEQ ID NO:311 include Public GI ID no. 125546035 (SEQ ID NO:312), Ceres CLONE ID no. 125228 (SEQ ID NO:314), Public GI ID no. 115465055 (SEQ ID NO:315), Public GI ID no. 125553080 (SEQ ID NO:316), Public GI ID no. 8920606 (SEQ ID NO:317), Ceres CLONE ID no. 1919643 (SEQ ID NO:325), Public GI ID no. 429155 (SEQ ID NO:327), Ceres CLONE ID no. 1194199 (SEQ ID NO:329), Public GI ID no. 15236631 (SEQ ID NO:330), Ceres ANNOT ID no. 1523420 (SEQ ID NO:332), Ceres ANNOT ID no. 1447046 (SEQ ID NO:334), Public GI ID no. 25296101 (SEQ ID NO:336), Public GI ID no. 15228440 (SEQ ID NO:337), Public GI ID no. 6624612 (SEQ ID NO:338), Public GI ID no. 125588688 (SEQ ID NO:339), Public GI ID no. 115470859 (SEQ ID NO:340), Public GI ID no. 15228865 (SEQ ID NO:341), Ceres CLONE ID no. 1571069 (SEQ ID NO:343), Public GI ID no. 115455903 (SEQ ID NO:344), Ceres ANNOT ID no. 1459422 (SEQ ID NO:346), Ceres CLONE ID no. 1577511 (SEQ ID NO:348), Public GI ID no. 115451657 (SEQ ID NO:349), Public GI ID no. 15225255 (SEQ ID NO:350), Public GI ID no. 125545695 (SEQ ID NO:351), Ceres ANNOT ID no. 1471817 (SEQ ID NO:353), Ceres ANNOT ID no. 1440896 (SEQ ID NO:355), Public GI ID no. 119393868 (SEQ ID NO:356), Ceres ANNOT ID no. 1517025 (SEQ ID NO:358), Ceres ANNOT ID no. 1512410 (SEQ ID NO:360), and Ceres ANNOT ID no. 6035498 (SEQ ID NO:362). In some cases, a functional homolog of SEQ ID NO:311 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:311.

Examples of amino acid sequences of functional homologs of the polypeptide set forth in SEQ ID NO:160 are provided in FIG. 13 and in the sequence listing. Such functional homologs include Ceres CLONE ID no. 1837065 (SEQ ID NO:162), Ceres ANNOT ID no. 1531178 (SEQ ID NO:184), Ceres CLONE ID no. 470694 (SEQ ID NO:242), Public GI ID no. 92867368 (SEQ ID NO:253), Ceres CLONE ID no. 859707 (SEQ ID NO:256), Ceres CLONE ID no. 392275 (SEQ ID NO:268), Ceres CLONE ID no. 1828394 (SEQ ID NO:282), and Public GI ID no. 115466694 (SEQ ID NO:294). Other functional homologs of SEQ ID NO:160 include Ceres CLONE ID no. 1895763 (SEQ ID NO:164), Ceres CLONE ID no. 1850460 (SEQ ID NO:166), Ceres CLONE ID no. 1808074 (SEQ ID NO:168), Ceres CLONE ID no. 1832882 (SEQ ID NO:170), Ceres CLONE ID no. 1978977 (SEQ ID NO:172), Ceres CLONE ID no. 1918742 (SEQ ID NO:174), Ceres CLONE ID no. 1940023 (SEQ ID NO:176), Ceres CLONE ID no. 1923495 (SEQ ID NO:178), Ceres CLONE ID no. 1851388 (SEQ ID NO:182), Ceres ANNOT ID no. 1477681 (SEQ ID NO:186), Ceres ANNOT ID no. 1508800 (SEQ ID NO:188), Ceres ANNOT ID no. 1455597 (SEQ ID NO:190), Ceres ANNOT ID no. 1532016 (SEQ ID NO:192), Ceres ANNOT ID no. 1478526 (SEQ ID NO:194), Ceres ANNOT ID no. 1492567 (SEQ ID NO:196), Ceres ANNOT ID no. 1515273 (SEQ ID NO:198), Ceres ANNOT ID no. 1461979 (SEQ ID NO:200), Ceres ANNOT ID no. 1439702 (SEQ ID NO:202), Ceres ANNOT ID no. 1448044 (SEQ ID NO:204), Ceres ANNOT ID no. 1483370 (SEQ ID NO:206), Ceres ANNOT ID no. 1445651 (SEQ ID NO:208), Ceres ANNOT ID no. 1490863 (SEQ ID NO:212), Ceres ANNOT ID no. 1501043 (SEQ ID NO:214), Ceres ANNOT ID no. 1527507 (SEQ ID NO:216), Ceres ANNOT ID no. 1498633 (SEQ ID NO:218), Ceres ANNOT ID no. 1465403 (SEQ ID NO:220), Ceres ANNOT ID no. 1510956 (SEQ ID NO:222), Ceres ANNOT ID no. 1457735 (SEQ ID NO:224), Public GI ID no. 15224711 (SEQ ID NO:225), Ceres CLONE ID no. 40062 (SEQ ID NO:228), Public GI ID no. 15220315 (SEQ ID NO:229), Ceres CLONE ID no. 36480 (SEQ ID NO:231), Ceres CLONE ID no. 2443 (SEQ ID NO:233), Public GI ID no. 30685375 (SEQ ID NO:234), Public GI ID no. 126009434 (SEQ ID NO:235), Ceres CLONE ID no. 965753 (SEQ ID NO:237), Ceres CLONE ID no. 948834 (SEQ ID NO:239), Public GI ID no. 33347409 (SEQ ID NO:240), Ceres CLONE ID no. 643614 (SEQ ID NO:244), Ceres CLONE ID no. 1049362 (SEQ ID NO:246), Ceres CLONE ID no. 546675 (SEQ ID NO:248), Ceres CLONE ID no. 522046 (SEQ ID NO:250), Ceres CLONE ID no. 651076 (SEQ ID NO:252), Public GI ID no. 92897590 (SEQ ID NO:254), Ceres CLONE ID no. 634176 (SEQ ID NO:258), Ceres CLONE ID no. 1041432 (SEQ ID NO:260), Ceres CLONE ID no. 1065203 (SEQ ID NO:262), Ceres CLONE ID no. 555361 (SEQ ID NO:264), Ceres CLONE ID no. 704227 (SEQ ID NO:266), Ceres CLONE ID no. 100819945 (SEQ ID NO:269), Ceres CLONE ID no. 282584 (SEQ ID NO:271), Ceres CLONE ID no. 1448469 (SEQ ID NO:273), Ceres CLONE ID no. 241246 (SEQ ID NO:275), Ceres CLONE ID no. 234443 (SEQ ID NO:277), Ceres CLONE ID no. 293549 (SEQ ID NO:279), Public GI ID no. 109450926 (SEQ ID NO:280), Ceres CLONE ID no. 1803923 (SEQ ID NO:284), Ceres CLONE ID no. 2024557 (SEQ ID NO:286), Ceres CLONE ID no. 1820364 (SEQ ID NO:288), Public GI ID no. 125554274 (SEQ ID NO:289), Public GI ID no. 125531165 (SEQ ID NO:290), Public GI ID no. 125541514 (SEQ ID NO:291), Public GI ID no. 125557559 (SEQ ID NO:292), Public GI ID no. 125557844 (SEQ ID NO:293), Public GI ID no. 115449295 (SEQ ID NO:295), Public GI ID no. 115481182 (SEQ ID NO:296), Public GI ID no. 20177639 (SEQ ID NO:297), Public GI ID no. 115471021 (SEQ ID NO:298), Public GI ID no. 115456011 (SEQ ID NO:299), Public GI ID no. 125588290 (SEQ ID NO:300), Public GI ID no. 115477799 (SEQ ID NO:301), Public GI ID no. 115471385 (SEQ ID NO:302), Public GI ID no. 125599705 (SEQ ID NO:303), Public GI ID no. 115489810 (SEQ ID NO:304), Public GI ID no. 55276718 (SEQ ID NO:305), Ceres ANNOT ID no. 6025568 (SEQ ID NO:307), and Ceres ANNOT ID no. 6091128 (SEQ ID NO:309). In some cases, a functional homolog of SEQ ID NO:160 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:160.

Examples of amino acid sequences of functional homologs of the polypeptide set forth in SEQ ID NO:2 are provided in FIG. 14 and in the sequence listing. Such functional homologs include Public GI ID no. 115470807 (SEQ ID NO:5), Ceres CLONE ID no. 1842931 (SEQ ID NO:15), Ceres CLONE ID no. 321308 (SEQ ID NO:17), Ceres CLONE ID no. 1725811 (SEQ ID NO:19), Ceres CLONE ID no. 1357455 (SEQ ID NO:21), Ceres CLONE ID no. 943370 (SEQ ID NO:23), Ceres CLONE ID no. 1327712 (SEQ ID NO:25), Ceres CLONE ID no. 1764692 (SEQ ID NO:27), and Ceres ANNOT ID no. 1512656 (SEQ ID NO:41). Other functional homologs of SEQ ID NO:2 include Public GI ID no. 18403425 (SEQ ID NO:3), Public GI ID no. 11994285 (SEQ ID NO:4), Public GI ID no. 108706298 (SEQ ID NO:6), Public GI ID no. 15233585 (SEQ ID NO:7), Public GI ID no. 125599279 (SEQ ID NO:8), Public GI ID no. 115450865 (SEQ ID NO:9), Public GI ID no. 22773244 (SEQ ID NO:10), Public GI ID no. 92874749 (SEQ ID NO:11), Ceres CLONE ID no. 1857034 (SEQ ID NO:13), Ceres CLONE ID no. 1059300 (SEQ ID NO:29), Ceres CLONE ID no. 1804869 (SEQ ID NO:31), Ceres CLONE ID no. 378863 (SEQ ID NO:33), Ceres CLONE ID no. 1930271 (SEQ ID NO:35), Ceres CLONE ID no. 2034728 (SEQ ID NO:37), Ceres CLONE ID no. 1866421 (SEQ ID NO:39), Ceres ANNOT ID no. 1463492 (SEQ ID NO:43), Ceres ANNOT ID no. 1459391 (SEQ ID NO:45), Ceres ANNOT ID no. 1442920 (SEQ ID NO:47), Ceres ANNOT ID no. 6011447 (SEQ ID NO:49), Ceres ANNOT ID no. 6068218 (SEQ ID NO:51), Ceres ANNOT ID no. 6044121 (SEQ ID NO:53), and Ceres ANNOT ID no. 6100755 (SEQ ID NO:55). In some cases, a functional homolog of SEQ ID NO:2 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:2.

Examples of amino acid sequences of functional homologs of the polypeptide set forth in SEQ ID NO:749 are provided in FIG. 15 and in the sequence listing. Such functional homologs include Ceres CLONE ID no. 1847516 (SEQ ID NO:1195), Ceres CLONE ID no. 1961986 (SEQ ID NO:1201), and Ceres ANNOT ID no. 6091930 (SEQ ID NO:1207). Other functional homologs of SEQ ID NO:749 include Ceres CLONE ID no. 2025938 (SEQ ID NO:885), Ceres CLONE ID no. 1821214 (SEQ ID NO:1189), Ceres CLONE ID no. 1040399 (SEQ ID NO:1191), Ceres CLONE ID no. 1093691 (SEQ ID NO:1193), Ceres CLONE ID no. 974539 (SEQ ID NO:1197), Ceres CLONE ID no. 1832340 (SEQ ID NO:1199), Ceres CLONE ID no. 1933211 (SEQ ID NO:1203), Ceres CLONE ID no. 997558 (SEQ ID NO:1205), Ceres ANNOT ID no. 6041596 (SEQ ID NO:1209), Public GI ID no. 125564176 (SEQ ID NO:1210), Ceres CLONE ID no. 1836064 (SEQ ID NO:1212), Ceres CLONE ID no. 1909693 (SEQ ID NO:1214), Public GI ID no. 40287480 (SEQ ID NO:1216), Ceres CLONE ID no. 1765346 (SEQ ID NO:1218), Public GI ID no. 125546008 (SEQ ID NO:1219), Ceres CLONE ID no. 1950900 (SEQ ID NO:1221), Public GI ID no. 41350259 (SEQ ID NO:1222), Public GI ID no. 125588210 (SEQ ID NO:1223), Ceres CLONE ID no. 1954395 (SEQ ID NO:1225), Public GI ID no. 18403408 (SEQ ID NO:1226), Ceres CLONE ID no. 2010121 (SEQ ID NO:1228), Ceres ANNOT ID no. 6011486 (SEQ ID NO:1230), Public GI ID no. 25082726 (SEQ ID NO:1231), Public GI ID no. 113196593 (SEQ ID NO:1232), Ceres CLONE ID no. 1843021 (SEQ ID NO:1234), Ceres CLONE ID no. 1931194 (SEQ ID NO:1236), Ceres CLONE ID no. 1652996 (SEQ ID NO:1238), Ceres CLONE ID no. 1930044 (SEQ ID NO:1240), Ceres CLONE ID no. 24255 (SEQ ID NO:1242), Ceres ANNOT ID no. 6034955 (SEQ ID NO:1244), Ceres ANNOT ID no. 6119444 (SEQ ID NO:1246), Ceres ANNOT ID no. 6063956 (SEQ ID NO:1248), Ceres ANNOT ID no. 6015461 (SEQ ID NO:1250), Ceres CLONE ID no. 696244 (SEQ ID NO:1252), Ceres ANNOT ID no. 1468973 (SEQ ID NO:1254), Ceres CLONE ID no. 2019529 (SEQ ID NO:1256), and Ceres CLONE ID no. 1492169 (SEQ ID NO:1258). In some cases, a functional homolog of SEQ ID NO:749 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:749.

Examples of amino acid sequences of functional homologs of the polypeptide set forth in SEQ ID NO:1311 are provided in FIG. 16 and in the sequence listing. Such functional homologs include CeresClone:971761 (SEQ ID NO: 1313), CeresClone:1946574 (SEQ ID NO: 1331), CeresClone:2055551 (SEQ ID NO: 1340), CeresClone: 100045499 (SEQ ID NO: 1347), CeresClone:1465853 (SEQ ID NO: 1353), CeresClone:753982 (SEQ ID NO: 1360), CeresClone:1076093 (SEQ ID NO: 1315), CeresClone: 1627875 (SEQ ID NO: 1317), CeresAnnot:1508362 (SEQ ID NO: 1319), CeresAnnot:1526950 (SEQ ID NO: 1321), CeresClone:1832333 (SEQ ID NO: 1323), GI:74272607 (SEQ ID NO: 1324), GI:192910782 (SEQ ID NO: 1325), GI:157342563 (SEQ ID NO: 1326), GI:159483497 (SEQ ID NO: 1327), CeresClone:1839999 (SEQ ID NO: 1329), CeresClone:467335 (SEQ ID NO: 1333), GI:168010087 (SEQ ID NO: 1334), CeresClone:1728202 (SEQ ID NO: 1336), CeresClone:1994239 (SEQ ID NO: 1338), CeresAnnot:8704704 (SEQ ID NO: 1342), GI:115453877 (SEQ ID NO: 1343), CeresClone:1646411 (SEQ ID NO: 1345), CeresClone:100920260 (SEQ ID NO: 1349), GI:116786147 (SEQ ID NO: 1350), GI:116783944 (SEQ ID NO: 1351), GI:82623397 (SEQ ID NO: 1354), CeresAnnot:8656662 (SEQ ID NO: 1356), CeresClone:1417803 (SEQ ID NO: 1358), and GI:145345927 (SEQ ID NO: 1361). In some cases, a functional homolog of SEQ ID NO:1311 has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1311.

The identification of conserved regions in a heat and/or drought-tolerance polypeptide facilitates production of variants of heat and/or drought-tolerance polypeptides. Variants of heat and/or drought-tolerance polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1-16. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful heat and/or drought-tolerance polypeptides include those that fit a Hidden Markov Model based on the polypeptides set forth in any one of FIGS. 1-16. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate heat and/or drought-tolerance polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The heat and/or drought-tolerance polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a heat and/or drought-tolerance polypeptide discussed below is about 50%, 60%, 70%, 80%, 90%, or 95% of the HMM bit score of a functional homolog provided in Sequence Listing. In some embodiments, a heat and/or drought-tolerance polypeptide discussed below fits the indicated HMM with an HMM bit score greater than 20, and has a domain indicative of a heat and/or drought-tolerance polypeptide. In some embodiments, a heat and/or drought-tolerance polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-16.

Polypeptides are shown in the sequence listing that have HMM bit scores greater than 270 when fitted to an HMM generated from the amino acid sequences set forth in FIG. 1. Such polypeptides include Ceres SEEDLINE ID no. ME00029 (SEQ ID NO:442), Public GI ID no. 72384401 (SEQ ID NO:443), Ceres CLONE ID no. 1079382 (SEQ ID NO:445), Ceres CLONE ID no. 1853461 (SEQ ID NO:447), Ceres CLONE ID no. 1626485 (SEQ ID NO:451), Ceres CLONE ID no. 1713920 (SEQ ID NO:459), Ceres CLONE ID no. 1772747 (SEQ ID NO:463), Ceres CLONE ID no. 225960 (SEQ ID NO:465), Public GI ID no. 115443807 (SEQ ID NO:470), Ceres CLONE ID no. 569388 (SEQ ID NO:483), Ceres CLONE ID no. 1915549 (SEQ ID NO:449), Ceres CLONE ID no. 529871 (SEQ ID NO:453), Ceres CLONE ID no. 1067079 (SEQ ID NO:455), Ceres CLONE ID no. 1079572 (SEQ ID NO:457), Ceres ANNOT ID no. 1456550 (SEQ ID NO:461), Ceres CLONE ID no. 1437889 (SEQ ID NO:469), Ceres CLONE ID no. 2014249 (SEQ ID NO:472), Ceres CLONE ID no. 2033133 (SEQ ID NO:474), Ceres CLONE ID no. 707404 (SEQ ID NO:476), Ceres CLONE ID no. 1770680 (SEQ ID NO:478), Ceres ANNOT ID no. 1450989 (SEQ ID NO:480), Public GI ID no. 72384445 (SEQ ID NO:481), Ceres CLONE ID no. 1059299 (SEQ ID NO:485), and Ceres ANNOT ID no. 6008086 (SEQ ID NO:487).

Polypeptides are shown in the sequence listing that have HMM bit scores greater than 100 when fitted to an HMM generated from the amino acid sequences set forth in FIG. 2. Such polypeptides include Ceres SEEDLINE ID no. ME00045 (SEQ ID NO:489), Ceres CLONE ID no. 571200 (SEQ ID NO:494), Ceres CLONE ID no. 1928532 (SEQ ID NO:496), Ceres ANNOT ID no. 1490637 (SEQ ID NO:498), Ceres CLONE ID no. 295496 (SEQ ID NO:514), Public GI ID no. 115463637 (SEQ ID NO:515), Ceres CLONE ID no. 1999444 (SEQ ID NO:518), Public GI ID no. 147844794 (SEQ ID NO:490), Public GI ID no. 147842279 (SEQ ID NO:491), Public GI ID no. 145355441 (SEQ ID NO:492), Ceres ANNOT ID no. 1461381 (SEQ ID NO:500), Ceres ANNOT ID no. 1440313 (SEQ ID NO:502), Ceres ANNOT ID no. 1448275 (SEQ ID NO:504), Ceres ANNOT ID no. 1437838 (SEQ ID NO:506), Ceres ANNOT ID no. 1501275 (SEQ ID NO:508), Ceres CLONE ID no. 1644562 (SEQ ID NO:510), Ceres CLONE ID no. 1925967 (SEQ ID NO:512), Public GI ID no. 115435904 (SEQ ID NO:516), Public GI ID no. 125552168 (SEQ ID NO:519), Public GI ID no. 125594093 (SEQ ID NO:520), Ceres CLONE ID no. 221188 (SEQ ID NO:522), Ceres ANNOT ID no. 1477714 (SEQ ID NO:524), Ceres CLONE ID no. 1787953 (SEQ ID NO:526), Ceres ANNOT ID no. 1531210 (SEQ ID NO:528), Ceres CLONE ID no. 521176 (SEQ ID NO:530), Public GI ID no. 22327055 (SEQ ID NO:531), Ceres ANNOT ID no. 1508824 (SEQ ID NO:533), Ceres CLONE ID no. 38879 (SEQ ID NO:535), Public GI ID no. 42569309 (SEQ ID NO:536), Ceres CLONE ID no. 1817784 (SEQ ID NO:538), Ceres CLONE ID no. 284637 (SEQ ID NO:540), Public GI ID no. 125596251 (SEQ ID NO:541), Public GI ID no. 125554300 (SEQ ID NO:543), Ceres CLONE ID no. 1935437 (SEQ ID NO:545), Ceres ANNOT ID no. 1455622 (SEQ ID NO:547), Public GI ID no. 55771354 (SEQ ID NO:548), Ceres ANNOT ID no. 1514655 (SEQ ID NO:550), Ceres CLONE ID no. 1848736 (SEQ ID NO:552), Public GI ID no. 125569872 (SEQ ID NO:553), Ceres CLONE ID no. 1645078 (SEQ ID NO:555), Ceres CLONE ID no. 1790573 (SEQ ID NO:557), Public GI ID no. 4567251 (SEQ ID NO:558), Ceres CLONE ID no. 444113 (SEQ ID NO:561), Public GI ID no. 125525355 (SEQ ID NO:562), Ceres ANNOT ID no. 6028854 (SEQ ID NO:564), and Ceres ANNOT ID no. 6115356 (SEQ ID NO:566).

Polypeptides are shown in the sequence listing that have HMM bit scores greater than 150 when fitted to an HMM generated from the amino acid sequences set forth in FIG. 3. Such polypeptides include Ceres SEEDLINE ID no. ME02190 (SEQ ID NO:568), Ceres CLONE ID no. 695006 (SEQ ID NO:578), Ceres ANNOT ID no. 1527488 (SEQ ID NO:584), Public GI ID no. 79318519 (SEQ ID NO:569), Public GI ID no. 79318537 (SEQ ID NO:570), Ceres CLONE ID no. 956998 (SEQ ID NO:572), Ceres CLONE ID no. 978154 (SEQ ID NO:574), Ceres CLONE ID no. 1035628 (SEQ ID NO:576), Ceres CLONE ID no. 464169 (SEQ ID NO:580), Ceres ANNOT ID no. 1474075 (SEQ ID NO:582), Ceres ANNOT ID no. 1474073 (SEQ ID NO:586), and Ceres ANNOT ID no. 1527486 (SEQ ID NO:588).

Polypeptides are shown in the sequence listing that have HMM bit scores greater than 120 when fitted to an HMM generated from the amino acid sequences set forth in FIG. 4. Such polypeptides include Ceres SEEDLINE ID no. ME02549 (SEQ ID NO:590), Ceres ANNOT ID no. 1501305 (SEQ ID NO:623), Ceres CLONE ID no. 607280 (SEQ ID NO:627), Public GI ID no. 92887174 (SEQ ID NO:632), Ceres CLONE ID no. 1857162 (SEQ ID NO:634), Public GI ID no. 115477272 (SEQ ID NO:674), Ceres CLONE ID no. 264002 (SEQ ID NO:682), Public GI ID no. 147822456 (SEQ ID NO:591), Public GI ID no. 144923935 (SEQ ID NO:592), Public GI ID no. 140038730 (SEQ ID NO:593), Public GI ID no. 78708014 (SEQ ID NO:594), Public GI ID no. 115481362 (SEQ ID NO:595), Public GI ID no. 125531350 (SEQ ID NO:596), Public GI ID no. 125525598 (SEQ ID NO:597), Public GI ID no. 77548630 (SEQ ID NO:598), Public GI ID no. 46798895 (SEQ ID NO:599), Public GI ID no. 125564653 (SEQ ID NO:600), Ceres CLONE ID no. 998865 (SEQ ID NO:602), Public GI ID no. 125556140 (SEQ ID NO:603), Public GI ID no. 125534482 (SEQ ID NO:604), Public GI ID no. 125550135 (SEQ ID NO:605), Ceres CLONE ID no. 639816 (SEQ ID NO:607), Public GI ID no. 125562170 (SEQ ID NO:608), Ceres CLONE ID no. 1797059 (SEQ ID NO:610), Ceres CLONE ID no. 1031510 (SEQ ID NO:612), Ceres CLONE ID no. 1973081 (SEQ ID NO:614), Public GI ID no. 125561002 (SEQ ID NO:615), Public GI ID no. 125541732 (SEQ ID NO:616), Public GI ID no. 125560677 (SEQ ID NO:617), Public GI ID no. 125559115 (SEQ ID NO:618), Public GI ID no. 15809903 (SEQ ID NO:619), Public GI ID no. 30681703 (SEQ ID NO:620), Public GI ID no. 9759556 (SEQ ID NO:621), Ceres ANNOT ID no. 1448303 (SEQ ID NO:625), Ceres ANNOT ID no. 1448305 (SEQ ID NO:629), Ceres ANNOT ID no. 1448307 (SEQ ID NO:631), Public GI ID no. 92888243 (SEQ ID NO:635), Public GI ID no. 92879395 (SEQ ID NO:636), Ceres CLONE ID no. 528876 (SEQ ID NO:638), Ceres ANNOT ID no. 1448352 (SEQ ID NO:640), Ceres ANNOT ID no. 1437745 (SEQ ID NO:642), Ceres ANNOT ID no. 1464146 (SEQ ID NO:644), Ceres ANNOT ID no. 1437744 (SEQ ID NO:646), Public GI ID no. 92894684 (SEQ ID NO:647), Ceres CLONE ID no. 3964 (SEQ ID NO:650), Public GI ID no. 13272389 (SEQ ID NO:651), Ceres ANNOT ID no. 1481203 (SEQ ID NO:653), Public GI ID no. 15227699 (SEQ ID NO:654), Public GI ID no. 92886084 (SEQ ID NO:655), Public GI ID no. 15239947 (SEQ ID NO:656), Ceres CLONE ID no.

34878 (SEQ ID NO:658), Ceres CLONE ID no. 150484 (SEQ ID NO:660), Public GI ID no. 21553545 (SEQ ID NO:661), Public GI ID no. 15222843 (SEQ ID NO:662), Public GI ID no. 38230552 (SEQ ID NO:663), Public GI ID no. 3420008 (SEQ ID NO:664), Public GI ID no. 15230602 (SEQ ID NO:665), Public GI ID no. 3420004 (SEQ ID NO:666), Public GI ID no. 2129586 (SEQ ID NO:667), Public GI ID no. 15217849 (SEQ ID NO:668), Public GI ID no. 15227704 (SEQ ID NO:669), Ceres ANNOT ID no. 1465750 (SEQ ID NO:671), Ceres CLONE ID no. 1983975 (SEQ ID NO:673), Public GI ID no. 15226028 (SEQ ID NO:675), Public GI ID no. 115459524 (SEQ ID NO:676), Ceres CLONE ID no. 1793353 (SEQ ID NO:678), Ceres ANNOT ID no. 1467399 (SEQ ID NO:680), Ceres CLONE ID no. 1982930 (SEQ ID NO:684), Public GI ID no. 125540700 (SEQ ID NO:685), Ceres ANNOT ID no. 1448743 (SEQ ID NO:687), Public GI ID no. 50251910 (SEQ ID NO:688), Ceres CLONE ID no. 1836748 (SEQ ID NO:690), Public GI ID no. 3420006 (SEQ ID NO:691), Public GI ID no. 92879376 (SEQ ID NO:692), Ceres CLONE ID no. 838941 (SEQ ID NO:694), Ceres ANNOT ID no. 1437746 (SEQ ID NO:696), Ceres ANNOT ID no. 6017241 (SEQ ID NO:698), Ceres ANNOT ID no. 6085947 (SEQ ID NO:700), and Ceres ANNOT ID no. 6017242 (SEQ ID NO:702).

Polypeptides are shown in the sequence listing that have HMM bit scores greater than 55 when fitted to an HMM generated from the amino acid sequences set forth in FIG. 5. Such polypeptides include Ceres SEEDLINE ID no. ME02865 (SEQ ID NO:705), Public GI ID no. 79320952 (SEQ ID NO:706), Public GI ID no. 79320957 (SEQ ID NO:707), Public GI ID no. 6692094 (SEQ ID NO:708), and Public GI ID no. 145323049 (SEQ ID NO:709).

Polypeptides are shown in the sequence listing that have HMM bit scores greater than 185 when fitted to an HMM generated from the amino acid sequences set forth in FIG. 6. Such polypeptides include Ceres SEEDLINE ID no. ME03227 (SEQ ID NO:711), Ceres CLONE ID no. 964616 (SEQ ID NO:714), Ceres CLONE ID no. 100009667 (SEQ ID NO:715), Ceres ANNOT ID no. 1444568 (SEQ ID NO:719), Ceres CLONE ID no. 719489 (SEQ ID NO:725), Ceres CLONE ID no. 587748 (SEQ ID NO:733), Public GI ID no. 125528114 (SEQ ID NO:734), Ceres CLONE ID no. 274172 (SEQ ID NO:737), Public GI ID no. 144923134 (SEQ ID NO:712), Ceres ANNOT ID no. 1471437 (SEQ ID NO:717), Ceres CLONE ID no. 1270484 (SEQ ID NO:721), Ceres CLONE ID no. 1075098 (SEQ ID NO:723), Public GI ID no. 18412211 (SEQ ID NO:727), Ceres CLONE ID no. 20358 (SEQ ID NO:729), Ceres CLONE ID no. 1915503 (SEQ ID NO:731), Public GI ID no. 115440619 (SEQ ID NO:735), Public GI ID no. 125572387 (SEQ ID NO:738), and Ceres ANNOT ID no. 6015812 (SEQ ID NO:740).

Polypeptides are shown in the sequence listing that have HMM bit scores greater than 110 when fitted to an HMM generated from the amino acid sequences set forth in FIG. 7. Such polypeptides include Ceres SEEDLINE ID no. ME04477 (SEQ ID NO:742), Ceres CLONE ID no. 1620215 (SEQ ID NO: 759); Ceres CLONE ID no. 1798756 (SEQ ID NO: 763); Public GI ID no. 38016527 (SEQ ID NO: 796); Public GI ID no. 75133829 (SEQ ID NO: 799); Ceres ANNOT ID no. 1460527 (SEQ ID NO: 801); Public GI ID no. 119720772 (SEQ ID NO: 857); Ceres CLONE ID no. 708446 (SEQ ID NO: 859); Public GI ID no. 92896423 (SEQ ID NO: 892); Ceres CLONE ID no. 1387149 (SEQ ID NO: 912); Public GI ID no. 5031281 (SEQ ID NO: 953); Ceres CLONE ID no. 1775820 (SEQ ID NO: 955); Public GI ID no. 35187687 (SEQ ID NO: 988); Public GI ID no. 115468934 (SEQ ID NO: 991); Public GI ID no. 118424243 (SEQ ID NO: 1000); Ceres ANNOT ID no. 6063957 (SEQ ID NO: 1010); Public GI ID no. 113196593 (SEQ ID NO: 798); Public GI ID no. 112819496 (SEQ ID NO: 999); Public GI ID no. 147783026 (SEQ ID NO: 743); Public GI ID no. 119367488 (SEQ ID NO: 744); Public GI ID no. 147860340 (SEQ ID NO: 745); Public GI ID no. 115477170 (SEQ ID NO: 757); Ceres CLONE ID no. 1931889 (SEQ ID NO: 761); Ceres CLONE ID no. 1918424 (SEQ ID NO: 767); Ceres CLONE ID no. 1845154 (SEQ ID NO: 771); Ceres Clone ID no. 1084216 (SEQ ID NO: 797); Ceres Annot ID no. 8644540 (SEQ ID NO: 805); Ceres ANNOT ID no. 1450673 (SEQ ID NO: 807); Public GI ID no. 116778802 (SEQ ID NO: 808); Public GI ID no. 116778893 (SEQ ID NO: 809); and Public GI ID no. 116778998 (SEQ ID NO: 810); Public GI ID no. 157849766 (SEQ ID NO: 811); Public GI ID no. 159474166 (SEQ ID NO: 812); Public GI ID no. 168036656 (SEQ ID NO: 813); Ceres ANNOT ID no. 1456578 (SEQ ID NO: 815); Public GI ID no. 168053490 (SEQ ID NO: 816); Public GI ID no. 193237563 (SEQ ID NO: 817); Ceres Clone ID no. 100879386 (SEQ ID NO: 819); Ceres Clone ID no. 2055733 (SEQ ID NO: 823); Ceres Clone ID no. 2056478 (SEQ ID NO: 825); Ceres CLONE ID no. 13007 (SEQ ID NO: 832); Ceres CLONE ID no. 5522 (SEQ ID NO: 834); Ceres CLONE ID no. 30543 (SEQ ID NO: 836); Ceres CLONE ID no. 14203 (SEQ ID NO: 839); Ceres CLONE ID no. 975913 (SEQ ID NO: 846); Ceres CLONE ID no. 967417 (SEQ ID NO: 848); Ceres CLONE ID no. 1614593 (SEQ ID NO: 863); Ceres CLONE ID no. 2025938 (SEQ ID NO: 885); Ceres CLONE ID no. 634261 (SEQ ID NO: 900); Ceres CLONE ID no. 1423851 (SEQ ID NO: 918); Ceres CLONE ID no. 1589047 (SEQ ID NO: 939); Ceres CLONE ID no. 1748922 (SEQ ID NO: 944); Ceres CLONE ID no. 1787151 (SEQ ID NO: 957); Ceres CLONE ID no. 1765871 (SEQ ID NO: 973); Ceres CLONE ID no. 1990071 (SEQ ID NO: 977); Public GI ID no. 125556051 (SEQ ID NO: 989); Public GI ID no. 125561658 (SEQ ID NO: 990); Public GI ID no. 115470773 (SEQ ID NO: 992); Public GI ID no. 115444813 (SEQ ID NO: 993); GI ID no. 169363 (SEQ ID NO: 1215) and Ceres CLONE ID no. 24255 (SEQ ID NO: 1242).

Polypeptides are shown in the sequence listing that have HMM bit scores greater than 215 when fitted to an HMM generated from the amino acid sequences set forth in FIG. 8. Such polypeptides include Ceres SEEDLINE ID no. ME18396 (SEQ ID NO:1012), Ceres CLONE ID no. 287430 (SEQ ID NO:1018), Ceres ANNOT ID no. 451889 (SEQ ID NO:1020), Ceres CLONE ID no. 936084 (SEQ ID NO:1055), Ceres CLONE ID no. 1792501 (SEQ ID NO:1066), Ceres ANNOT ID no. 1437875 (SEQ ID NO:1068), Public GI ID no. 1853968 (SEQ ID NO:1093), Public GI ID no. 27530032 (SEQ ID NO:1094), Ceres CLONE ID no. 1834483 (SEQ ID NO:1110), Public GI ID no. 84579418 (SEQ ID NO:1113), Public GI ID no. 15077030 (SEQ ID NO:1117), Public GI ID no. 13752458 (SEQ ID NO:1118), Public GI ID no. 147865685 (SEQ ID NO:1013), Public GI ID no. 119503368 (SEQ ID NO:1014), Public GI ID no. 72161874 (SEQ ID NO:1015), Public GI ID no. 91780661 (SEQ ID NO:1016), Ceres ANNOT ID no. 835908 (SEQ ID NO:1022), Public GI ID no. 38326750 (SEQ ID NO:1023), Ceres CLONE ID no. 1939396 (SEQ ID NO:1025), Ceres CLONE ID no. 403637 (SEQ ID NO:1027), Public GI ID no. 42539907 (SEQ ID NO:1028), Ceres CLONE ID no. 1836494 (SEQ ID NO:1030), Public GI ID no. 15192945 (SEQ ID NO:1031), Ceres CLONE ID no. 1607947 (SEQ ID NO:1033), Ceres CLONE ID no.

115880 (SEQ ID NO:1035), Ceres CLONE ID no. 1074009 (SEQ ID NO:1037), Ceres CLONE ID no. 476073 (SEQ ID NO:1039), Ceres CLONE ID no. 554053 (SEQ ID NO:1041), Ceres CLONE ID no. 391449 (SEQ ID NO:1045), Ceres CLONE ID no. 1846400 (SEQ ID NO:1048), Ceres ANNOT ID no. 1475185 (SEQ ID NO:1050), Public GI ID no. 115457148 (SEQ ID NO:1051), Ceres ANNOT ID no. 1454960 (SEQ ID NO:1053), Public GI ID no. 50346893 (SEQ ID NO:1056), Ceres CLONE ID no. 1931526 (SEQ ID NO:1058), Ceres ANNOT ID no. 1454260 (SEQ ID NO:1061), Public GI ID no. 115456131 (SEQ ID NO:1062), Ceres CLONE ID no. 159151 (SEQ ID NO:1064), Ceres CLONE ID no. 1842801 (SEQ ID NO:1071), Ceres CLONE ID no. 533030 (SEQ ID NO:1073), Ceres CLONE ID no. 1931881 (SEQ ID NO:1075), Ceres ANNOT ID no. 1480006 (SEQ ID NO:1077), Ceres CLONE ID no. 1895007 (SEQ ID NO:1079), Public GI ID no. 3598863 (SEQ ID NO:1080), Ceres ANNOT ID no. 1471735 (SEQ ID NO:1082), Ceres CLONE ID no. 1937530 (SEQ ID NO:1084), Ceres CLONE ID no. 1833050 (SEQ ID NO:1086), Ceres CLONE ID no. 644213 (SEQ ID NO:1088), Ceres CLONE ID no. 568154 (SEQ ID NO:1090), Ceres CLONE ID no. 527598 (SEQ ID NO:1092), Ceres ANNOT ID no. 1487614 (SEQ ID NO:1096), Ceres ANNOT ID no. 1541881 (SEQ ID NO:1098), Ceres ANNOT ID no. 1488465 (SEQ ID NO:1100), Ceres ANNOT ID no. 1488468 (SEQ ID NO:1102), Ceres ANNOT ID no. 1541884 (SEQ ID NO:1104), Ceres ANNOT ID no. 1454972 (SEQ ID NO:1106), Ceres ANNOT ID no. 1475186 (SEQ ID NO:1108), Ceres CLONE ID no. 686198 (SEQ ID NO:1112), Public GI ID no. 84579420 (SEQ ID NO:1114), Ceres CLONE ID no. 605144 (SEQ ID NO:1116), Public GI ID no. 15077028 (SEQ ID NO:1119), Ceres ANNOT ID no. 1454963 (SEQ ID NO:1121), Ceres ANNOT ID no. 6030208 (SEQ ID NO:1123), and Ceres ANNOT ID no. 6076767 (SEQ ID NO:1125).

Polypeptides are shown in the sequence listing that have HMM bit scores greater than 105 when fitted to an HMM generated from the amino acid sequences set forth in FIG. 9. Such polypeptides include Ceres SEEDLINE ID no. ME20095 (SEQ ID NO:1129), Public GI ID no. 72255610 (SEQ ID NO:933), Ceres SEEDLINE ID no. ME20095 (SEQ ID NO:1129), Ceres CLONE ID no. 1562633 (SEQ ID NO:1140), Ceres ANNOT ID no. 1692728 (SEQ ID NO:1142), Ceres CLONE ID no. 921110 (SEQ ID NO:1144), Ceres CLONE ID no. 1791180 (SEQ ID NO:1146), Ceres CLONE ID no. 527891 (SEQ ID NO:1148), Ceres ANNOT ID no. 1522414 (SEQ ID NO:1150), Public GI ID no. 51458330 (SEQ ID NO:1182), Public GI ID no. 18399940 (SEQ ID NO:63), Ceres ANNOT ID no. 6107929 (SEQ ID NO:73), Ceres ANNOT ID no. 1473094 (SEQ ID NO:96), Ceres ANNOT ID no. 1503955 (SEQ ID NO:127), Ceres ANNOT ID no. 1526501 (SEQ ID NO:139), Public GI ID no. 15235713 (SEQ ID NO:179), Public GI ID no. 15234552 (SEQ ID NO:180), Ceres ANNOT ID no. 1520801 (SEQ ID NO:209), Ceres ANNOT ID no. 1443434 (SEQ ID NO:467), Public GI ID no. 30696058 (SEQ ID NO:559), Ceres ANNOT ID no. 1509601 (SEQ ID NO:648), Ceres ANNOT ID no. 1451912 (SEQ ID NO:726), Ceres ANNOT ID no. 6017545 (SEQ ID NO:741), Ceres ANNOT ID no. 1504999 (SEQ ID NO:765), Ceres ANNOT ID no. 1456402 (SEQ ID NO:773), Ceres ANNOT ID no. 1496359 (SEQ ID NO:781), Ceres ANNOT ID no. 1447260 (SEQ ID NO:842), Ceres ANNOT ID no. 1469023 (SEQ ID NO:861), Ceres ANNOT ID no. 1474186 (SEQ ID NO:865), Ceres ANNOT ID no. 1527596 (SEQ ID NO:867), Ceres CLONE ID no. 1919624 (SEQ ID NO:896), Ceres CLONE ID no. 677797 (SEQ ID NO:916), Public GI ID no. 7960729 (SEQ ID NO:932), Ceres CLONE ID no. 941845 (SEQ ID NO:1043), Public GI ID no. 30683008 (SEQ ID NO:1046), Public GI ID no. 42568786 (SEQ ID NO:1059), Ceres CLONE ID no. 255364 (SEQ ID NO:1069), Public GI ID no. 147771549 (SEQ ID NO:1130), Public GI ID no. 144924741 (SEQ ID NO:1131), Public GI ID no. 121594508 (SEQ ID NO:1132), Public GI ID no. 91202290 (SEQ ID NO:1133), Public GI ID no. 89900939 (SEQ ID NO:1134), Public GI ID no. 77917672 (SEQ ID NO:1135), Public GI ID no. 77165252 (SEQ ID NO:1136), Public GI ID no. 115375374 (SEQ ID NO:1137), Public GI ID no. 110602449 (SEQ ID NO:1138), Public GI ID no. 125540573 (SEQ ID NO:1151), Public GI ID no. 125561519 (SEQ ID NO:1152), Public GI ID no. 125528345 (SEQ ID NO:1153), Public GI ID no. 116310408 (SEQ ID NO:1154), Public GI ID no. 115483332 (SEQ ID NO:1156), Public GI ID no. 125575640 (SEQ ID NO:1157), Public GI ID no. 115476368 (SEQ ID NO:1158), Public GI ID no. 115478841 (SEQ ID NO:1159), Public GI ID no. 115467158 (SEQ ID NO:1160), Public GI ID no. 72384477 (SEQ ID NO:1161), Public GI ID no. 116054703 (SEQ ID NO:1162), Ceres CLONE ID no. 1786317 (SEQ ID NO:1164), Ceres CLONE ID no. 1791336 (SEQ ID NO:1166), Ceres CLONE ID no. 1877752 (SEQ ID NO:1168), Ceres CLONE ID no. 1821191 (SEQ ID NO:1170), Ceres CLONE ID no. 446838 (SEQ ID NO:1172), Ceres CLONE ID no. 1556915 (SEQ ID NO:1174), Public GI ID no. 90200725 (SEQ ID NO:1175), Ceres CLONE ID no. 1580247 (SEQ ID NO:1177), Ceres CLONE ID no. 644201 (SEQ ID NO:1179), Ceres CLONE ID no. 538689 (SEQ ID NO:1181), Ceres CLONE ID no. 817225 (SEQ ID NO:1184), and Ceres CLONE ID no. 923842 (SEQ ID NO:1186).

Polypeptides are shown in the sequence listing that have HMM bit scores greater than 55 when fitted to an HMM generated from the amino acid sequences set forth in FIG. 10. Such polypeptides include Ceres CLONE ID no. 31309 (SEQ ID NO:60), Ceres CLONE ID no. 872030 (SEQ ID NO:62), Ceres CLONE ID no. 100029223 (SEQ ID NO:74), Ceres CLONE ID no. 1939845 (SEQ ID NO:98), Ceres CLONE ID no. 2015383 (SEQ ID NO:102), Ceres CLONE ID no. 1607893 (SEQ ID NO:104), Ceres CLONE ID no. 1075133 (SEQ ID NO:152), Ceres CLONE ID no. 1218065 (SEQ ID NO:915), Public GI ID no. 15227919 (SEQ ID NO:64), Public GI ID no. 9843641 (SEQ ID NO:65), Public GI ID no. 124294789 (SEQ ID NO:66), Public GI ID no. 15233446 (SEQ ID NO:67), Public GI ID no. 115477679 (SEQ ID NO:68), Public GI ID no. 42407552 (SEQ ID NO:69), Public GI ID no. 125562450 (SEQ ID NO:70), Public GI ID no. 115469980 (SEQ ID NO:71), Ceres ANNOT ID no. 1442539 (SEQ ID NO:76), Ceres ANNOT ID no. 1442538 (SEQ ID NO:78), Ceres ANNOT ID no. 1460661 (SEQ ID NO:80), Ceres ANNOT ID no. 1452884 (SEQ ID NO:82), Ceres ANNOT ID no. 1450523 (SEQ ID NO:84), Ceres ANNOT ID no. 1442257 (SEQ ID NO:86), Ceres ANNOT ID no. 1541121 (SEQ ID NO:88), Ceres ANNOT ID no. 1480481 (SEQ ID NO:90), Ceres ANNOT ID no. 1487713 (SEQ ID NO:92), Ceres ANNOT ID no. 1456204 (SEQ ID NO:94), Ceres CLONE ID no. 1387402 (SEQ ID NO:100), Ceres CLONE ID no. 972919 (SEQ ID NO:106), Ceres CLONE ID no. 1645860 (SEQ ID NO:108), Ceres CLONE ID no. 1042804 (SEQ ID NO:110), Ceres CLONE ID no. 1606678 (SEQ ID NO:112), Ceres CLONE ID no. 684496 (SEQ ID NO:114), Ceres CLONE ID no. 1062366 (SEQ ID NO:116), Ceres CLONE ID no. 1722931

(SEQ ID NO:118), Ceres CLONE ID no. 746169 (SEQ ID NO:120), Ceres CLONE ID no. 1050475 (SEQ ID NO:122), Ceres CLONE ID no. 1728904 (SEQ ID NO:124), Ceres CLONE ID no. 1698538 (SEQ ID NO:126), Ceres CLONE ID no. 1762328 (SEQ ID NO:130), Ceres CLONE ID no. 1590072 (SEQ ID NO:132), Ceres CLONE ID no. 471593 (SEQ ID NO:134), Ceres CLONE ID no. 1031667 (SEQ ID NO:136), Ceres CLONE ID no. 1826085 (SEQ ID NO:138), Ceres CLONE ID no. 373932 (SEQ ID NO:142), Ceres CLONE ID no. 1797836 (SEQ ID NO:144), Ceres CLONE ID no. 1102774 (SEQ ID NO:146), Ceres CLONE ID no. 842287 (SEQ ID NO:148), Ceres CLONE ID no. 568205 (SEQ ID NO:150), Ceres ANNOT ID no. 6108997 (SEQ ID NO:154), Ceres ANNOT ID no. 6023609 (SEQ ID NO:156), and Ceres ANNOT ID no. 6017906 (SEQ ID NO:158).

Polypeptides are shown in the sequence listing that have HMM bit scores greater than 55 when fitted to an HMM generated from the amino acid sequences set forth in FIG. 11. Such polypeptides include Ceres LOCUS ID no. At2g26150 (SEQ ID NO:364), Ceres ANNOT ID no. 1455221 (SEQ ID NO:407), Public GI ID no. 729774 (SEQ ID NO:408), Ceres CLONE ID no. 1414288 (SEQ ID NO:410), Public GI ID no. 115482048 (SEQ ID NO:413), Public GI ID no. 56117815 (SEQ ID NO:421), Ceres ANNOT ID no. 1485538 (SEQ ID NO:366), Ceres ANNOT ID no. 1538505 (SEQ ID NO:368), Public GI ID no. 8347238 (SEQ ID NO:369), Public GI ID no. 125542955 (SEQ ID NO:370), Public GI ID no. 115446219 (SEQ ID NO:371), Ceres CLONE ID no. 1597127 (SEQ ID NO:373), Ceres CLONE ID no. 1584568 (SEQ ID NO:375), Ceres CLONE ID no. 286056 (SEQ ID NO:377), Ceres ANNOT ID no. 1543432 (SEQ ID NO:379), Ceres CLONE ID no. 1728062 (SEQ ID NO:381), Ceres ANNOT ID no. 1448950 (SEQ ID NO:383), Ceres CLONE ID no. 771500 (SEQ ID NO:385), Ceres ANNOT ID no. 1485096 (SEQ ID NO:387), Ceres CLONE ID no. 1646104 (SEQ ID NO:389), Public GI ID no. 111184724 (SEQ ID NO:390), Ceres CLONE ID no. 1362475 (SEQ ID NO:392), Ceres CLONE ID no. 597906 (SEQ ID NO:394), Ceres CLONE ID no. 615781 (SEQ ID NO:396), Ceres CLONE ID no. 538713 (SEQ ID NO:398), Ceres CLONE ID no. 1794141 (SEQ ID NO:400), Public GI ID no. 5821138 (SEQ ID NO:401), Public GI ID no. 886742 (SEQ ID NO:402), Ceres CLONE ID no. 1814498 (SEQ ID NO:404), Public GI ID no. 7158882 (SEQ ID NO:405), Ceres ANNOT ID no. 1452564 (SEQ ID NO:412), Public GI ID no. 125557431 (SEQ ID NO:414), Ceres ANNOT ID no. 1442880 (SEQ ID NO:416), Ceres ANNOT ID no. 1463437 (SEQ ID NO:418), Public GI ID no. 42415865 (SEQ ID NO:419), Public GI ID no. 33087081 (SEQ ID NO:420), Public GI ID no. 115521217 (SEQ ID NO:422), Public GI ID no. 115521211 (SEQ ID NO:423), Public GI ID no. 115521215 (SEQ ID NO:424), Ceres ANNOT ID no. 1454376 (SEQ ID NO:426), Ceres CLONE ID no. 835571 (SEQ ID NO:428), Ceres ANNOT ID no. 1500046 (SEQ ID NO:430), Public GI ID no. 110738569 (SEQ ID NO:431), Public GI ID no. 125542510 (SEQ ID NO:432), Public GI ID no. 30686034 (SEQ ID NO:433), Public GI ID no. 125570883 (SEQ ID NO:434), Public GI ID no. 42562463 (SEQ ID NO:435), Ceres CLONE ID no. 100043265 (SEQ ID NO:436), Ceres ANNOT ID no. 6089790 (SEQ ID NO:438), and Ceres ANNOT ID no. 6043635 (SEQ ID NO:440).

Polypeptides are shown in the sequence listing that have HMM bit scores greater than 50 when fitted to an HMM generated from the amino acid sequences set forth in FIG. 12. Such polypeptides include Ceres LOCUS ID no. At1g32330 (SEQ ID NO:311), Ceres ANNOT ID no. 1538958 (SEQ ID NO:319), Public GI ID no. 115521213 (SEQ ID NO:320), Public GI ID no. 42415865 (SEQ ID NO:321), Public GI ID no. 729775 (SEQ ID NO:322), Public GI ID no. 11386827 (SEQ ID NO:323), Public GI ID no. 115456675 (SEQ ID NO:326), Public GI ID no. 89274218 (SEQ ID NO:335), Public GI ID no. 125546035 (SEQ ID NO:312), Ceres CLONE ID no. 125228 (SEQ ID NO:314), Public GI ID no. 115465055 (SEQ ID NO:315), Public GI ID no. 125553080 (SEQ ID NO:316), Public GI ID no. 8920606 (SEQ ID NO:317), Ceres CLONE ID no. 1919643 (SEQ ID NO:325), Public GI ID no. 429155 (SEQ ID NO:327), Ceres CLONE ID no. 1194199 (SEQ ID NO:329), Public GI ID no. 15236631 (SEQ ID NO:330), Ceres ANNOT ID no. 1523420 (SEQ ID NO:332), Ceres ANNOT ID no. 1447046 (SEQ ID NO:334), Public GI ID no. 25296101 (SEQ ID NO:336), Public GI ID no. 15228440 (SEQ ID NO:337), Public GI ID no. 6624612 (SEQ ID NO:338), Public GI ID no. 125588688 (SEQ ID NO:339), Public GI ID no. 115470859 (SEQ ID NO:340), Public GI ID no. 15228865 (SEQ ID NO:341), Ceres CLONE ID no. 1571069 (SEQ ID NO:343), Public GI ID no. 115455903 (SEQ ID NO:344), Ceres ANNOT ID no. 1459422 (SEQ ID NO:346), Ceres CLONE ID no. 1577511 (SEQ ID NO:348), Public GI ID no. 115451657 (SEQ ID NO:349), Public GI ID no. 15225255 (SEQ ID NO:350), Public GI ID no. 125545695 (SEQ ID NO:351), Ceres ANNOT ID no. 1471817 (SEQ ID NO:353), Ceres ANNOT ID no. 1440896 (SEQ ID NO:355), Public GI ID no. 119393868 (SEQ ID NO:356), Ceres ANNOT ID no. 1517025 (SEQ ID NO:358), Ceres ANNOT ID no. 1512410 (SEQ ID NO:360), and Ceres ANNOT ID no. 6035498 (SEQ ID NO:362).

Polypeptides are shown in the sequence listing that have HMM bit scores greater than 25 when fitted to an HMM generated from the amino acid sequences set forth in FIG. 13. Such polypeptides include Ceres CLONE ID no. 41543 (SEQ ID NO:160) Ceres CLONE ID no. 1837065 (SEQ ID NO:162), Ceres ANNOT ID no. 1531178 (SEQ ID NO:184), Ceres CLONE ID no. 470694 (SEQ ID NO:242), Public GI ID no. 92867368 (SEQ ID NO:253), Ceres CLONE ID no. 859707 (SEQ ID NO:256), Ceres CLONE ID no. 392275 (SEQ ID NO:268), Ceres CLONE ID no. 1828394 (SEQ ID NO:282), Public GI ID no. 115466694 (SEQ ID NO:294), Ceres CLONE ID no. 1895763 (SEQ ID NO:164), Ceres CLONE ID no. 1850460 (SEQ ID NO:166), Ceres CLONE ID no. 1808074 (SEQ ID NO:168), Ceres CLONE ID no. 1832882 (SEQ ID NO:170), Ceres CLONE ID no. 1978977 (SEQ ID NO:172), Ceres CLONE ID no. 1918742 (SEQ ID NO:174), Ceres CLONE ID no. 1940023 (SEQ ID NO:176), Ceres CLONE ID no. 1923495 (SEQ ID NO:178), Ceres CLONE ID no. 1851388 (SEQ ID NO:182), Ceres ANNOT ID no. 1477681 (SEQ ID NO:186), Ceres ANNOT ID no. 1508800 (SEQ ID NO:188), Ceres ANNOT ID no. 1455597 (SEQ ID NO:190), Ceres ANNOT ID no. 1532016 (SEQ ID NO:192), Ceres ANNOT ID no. 1478526 (SEQ ID NO:194), Ceres ANNOT ID no. 1492567 (SEQ ID NO:196), Ceres ANNOT ID no. 1515273 (SEQ ID NO:198), Ceres ANNOT ID no. 1461979 (SEQ ID NO:200), Ceres ANNOT ID no. 1439702 (SEQ ID NO:202), Ceres ANNOT ID no. 1448044 (SEQ ID NO:204), Ceres ANNOT ID no. 1483370 (SEQ ID NO:206), Ceres ANNOT ID no. 1445651 (SEQ ID NO:208), Ceres ANNOT ID no. 1490863 (SEQ ID NO:212), Ceres ANNOT ID no. 1501043 (SEQ ID NO:214), Ceres ANNOT ID no. 1527507 (SEQ ID NO:216), Ceres ANNOT ID no. 1498633 (SEQ ID NO:218), Ceres ANNOT ID no. 1465403 (SEQ ID NO:220), Ceres ANNOT ID no. 1510956 (SEQ ID NO:222), Ceres ANNOT ID no. 1457735 (SEQ ID NO:224), Public GI ID no. 15224711 (SEQ ID NO:225), Ceres CLONE ID no. 40062 (SEQ ID NO:228), Public GI ID no. 15220315 (SEQ ID NO:229), Ceres CLONE ID no. 36480 (SEQ ID NO:231), Ceres CLONE ID no. 2443 (SEQ ID NO:233), Public GI ID no. 30685375 (SEQ ID NO:234), Public GI ID no. 126009434 (SEQ ID NO:235), Ceres CLONE ID no. 965753 (SEQ ID NO:237), Ceres CLONE ID no. 948834 (SEQ ID NO:239), Public GI ID no. 33347409 (SEQ ID NO:240), Ceres CLONE ID no. 643614 (SEQ ID NO:244), Ceres CLONE ID no. 1049362 (SEQ ID NO:246), Ceres CLONE ID no. 546675 (SEQ ID NO:248), Ceres CLONE ID no. 522046 (SEQ ID NO:250), Ceres CLONE ID no. 651076 (SEQ ID NO:252), Public GI ID no. 92897590 (SEQ ID NO:254), Ceres CLONE ID no. 634176 (SEQ ID NO:258), Ceres CLONE ID no. 1041432 (SEQ ID NO:260), Ceres CLONE ID no. 1065203 (SEQ ID NO:262), Ceres CLONE ID no. 555361 (SEQ ID NO:264), Ceres CLONE ID no. 704227 (SEQ ID NO:266), Ceres CLONE ID no. 100819945 (SEQ ID NO:269), Ceres CLONE ID no. 282584 (SEQ ID NO:271), Ceres CLONE ID no. 1448469 (SEQ ID NO:273), Ceres CLONE ID no. 241246 (SEQ ID NO:275), Ceres CLONE ID no. 234443 (SEQ ID NO:277), Ceres CLONE ID no. 293549 (SEQ ID NO:279), Public GI ID no. 109450926 (SEQ ID NO:280), Ceres CLONE ID no. 1803923 (SEQ ID NO:284), Ceres CLONE ID no. 2024557 (SEQ ID NO:286), Ceres CLONE ID no. 1820364 (SEQ ID NO:288), Public GI ID no. 125554274 (SEQ ID NO:289), Public GI ID no. 125531165 (SEQ ID NO:290), Public GI ID no. 125541514 (SEQ ID NO:291), Public GI ID no. 125557559 (SEQ ID NO:292), Public GI ID no. 125557844 (SEQ ID NO:293), Public GI ID no. 115449295 (SEQ ID NO:295), Public GI ID no. 115481182 (SEQ ID NO:296), Public GI ID no. 20177639 (SEQ ID NO:297), Public GI ID no. 115471021 (SEQ ID NO:298), Public GI ID no. 115456011 (SEQ ID NO:299), Public GI ID no. 125588290 (SEQ ID NO:300), Public GI ID no. 115477799 (SEQ ID NO:301), Public GI ID no. 115471385 (SEQ ID NO:302), Public GI ID no. 125599705 (SEQ ID NO:303), Public GI ID no. 115489810 (SEQ ID NO:304), Public GI ID no. 55276718 (SEQ ID NO:305), Ceres ANNOT ID no. 6025568 (SEQ ID NO:307), and Ceres ANNOT ID no. 6091128 (SEQ ID NO:309).

Polypeptides are shown in the sequence listing that have HMM bit scores greater than 85 when fitted to an HMM generated from the amino acid sequences set forth in FIG. 14. Such polypeptides include Ceres CLONE ID no. 14572 (SEQ ID NO:2), Public GI ID no. 115470807 (SEQ ID NO:5), Ceres CLONE ID no. 1842931 (SEQ ID NO:15), Ceres CLONE ID no. 321308 (SEQ ID NO:17), Ceres CLONE ID no. 1725811 (SEQ ID NO:19), Ceres CLONE ID no. 1357455 (SEQ ID NO:21), Ceres CLONE ID no. 943370 (SEQ ID NO:23), Ceres CLONE ID no. 1327712 (SEQ ID NO:25), Ceres CLONE ID no. 1764692 (SEQ ID NO:27), Ceres ANNOT ID no. 1512656 (SEQ ID NO:41), Public GI ID no. 18403425 (SEQ ID NO:3), Public GI ID no. 11994285 (SEQ ID NO:4), Public GI ID no. 108706298 (SEQ ID NO:6), Public GI ID no. 15233585 (SEQ ID NO:7), Public GI ID no. 125599279 (SEQ ID NO:8), Public GI ID no. 115450865 (SEQ ID NO:9), Public GI ID no. 22773244 (SEQ ID NO:10), Public GI ID no. 92874749 (SEQ ID NO:11), Ceres CLONE ID no. 1857034 (SEQ ID NO:13), Ceres CLONE ID no. 1059300 (SEQ ID NO:29), Ceres CLONE ID no. 1804869 (SEQ ID NO:31), Ceres CLONE ID no. 378863 (SEQ ID NO:33), Ceres CLONE ID no. 1930271 (SEQ ID NO:35), Ceres CLONE ID no. 2034728 (SEQ ID NO:37), Ceres CLONE ID no. 1866421 (SEQ ID NO:39), Ceres ANNOT ID no. 1463492 (SEQ ID NO:43), Ceres ANNOT ID no. 1459391 (SEQ ID NO:45), Ceres ANNOT ID no. 1442920 (SEQ ID NO:47), Ceres ANNOT ID no. 6011447 (SEQ ID NO:49), Ceres ANNOT ID no. 6068218 (SEQ ID NO:51), Ceres ANNOT ID no. 6044121 (SEQ ID NO:53), and Ceres ANNOT ID no. 6100755 (SEQ ID NO:55).

Polypeptides are shown in the sequence listing that have HMM bit scores greater than 70 when fitted to an HMM generated from the amino acid sequences set forth in FIG. 15. Such polypeptides include Ceres SEEDLINE ID no. ME02401 (SEQ ID NO:749), Ceres CLONE ID no. 1847516 (SEQ ID NO:1195), Ceres CLONE ID no. 1961986 (SEQ ID NO:1201), Ceres ANNOT ID no. 6091930 (SEQ ID NO:1207), Ceres CLONE ID no. 2025938 (SEQ ID NO:885), Ceres CLONE ID no. 1821214 (SEQ ID NO:1189), Ceres CLONE ID no. 1040399 (SEQ ID NO:1191), Ceres CLONE ID no. 1093691 (SEQ ID NO:1193), Ceres CLONE ID no. 974539 (SEQ ID NO:1197), Ceres CLONE ID no. 1832340 (SEQ ID NO:1199), Ceres CLONE ID no. 1933211 (SEQ ID NO:1203), Ceres CLONE ID no. 997558 (SEQ ID NO:1205), Ceres ANNOT ID no. 6041596 (SEQ ID NO:1209), Public GI ID no. 125564176 (SEQ ID NO:1210), Ceres CLONE ID no. 1836064 (SEQ ID NO:1212), Ceres CLONE ID no. 1909693 (SEQ ID NO:1214), Public GI ID no. 169363 (SEQ ID NO:1215), Public GI ID no. 40287480 (SEQ ID NO:1216), Ceres CLONE ID no. 1765346 (SEQ ID NO:1218), Public GI ID no. 125546008 (SEQ ID NO:1219), Ceres CLONE ID no. 1950900 (SEQ ID NO:1221), Public GI ID no. 41350259 (SEQ ID NO:1222), Public GI ID no. 125588210 (SEQ ID NO:1223), Ceres CLONE ID no. 1954395 (SEQ ID NO:1225), Public GI ID no. 18403408 (SEQ ID NO:1226), Ceres CLONE ID no. 2010121 (SEQ ID NO:1228), Ceres ANNOT ID no. 6011486 (SEQ ID NO:1230), Public GI ID no. 25082726 (SEQ ID NO:1231), Public GI ID no. 113196593 (SEQ ID NO:1232), Ceres CLONE ID no. 1843021 (SEQ ID NO:1234), Ceres CLONE ID no. 1931194 (SEQ ID NO:1236), Ceres CLONE ID no. 1652996 (SEQ ID NO:1238), Ceres CLONE ID no. 1930044 (SEQ ID NO:1240), Ceres CLONE ID no. 24255 (SEQ ID NO:1242), Ceres ANNOT ID no. 6034955 (SEQ ID NO:1244), Ceres ANNOT ID no. 6119444 (SEQ ID NO:1246), Ceres ANNOT ID no. 6063956 (SEQ ID NO:1248), Ceres ANNOT ID no. 6015461 (SEQ ID NO:1250), Ceres CLONE ID no. 696244 (SEQ ID NO:1252), Ceres ANNOT ID no. 1468973 (SEQ ID NO:1254), Ceres CLONE ID no. 2019529 (SEQ ID NO:1256), and Ceres CLONE ID no. 1492169 (SEQ ID NO:1258).

Polypeptides are shown in the sequence listing that have HMM bit scores greater than about 300 when fitted to an HMM generated from the amino acid sequences set forth in FIG. 16. Such polypeptides include Ceres SEEDLINE ID no. ME004246 (SEQ ID NO: 1311), CeresClone:971761 (SEQ ID NO: 1313), CeresClone:1946574 (SEQ ID NO: 1331), CeresClone:2055551 (SEQ ID NO: 1340), CeresClone:100045499 (SEQ ID NO: 1347), CeresClone:1465853 (SEQ ID NO: 1353), CeresClone:753982 (SEQ ID NO: 1360), CeresClone:1076093 (SEQ ID NO: 1315), CeresClone:1627875 (SEQ ID NO: 1317), CeresAnnot:1508362 (SEQ ID NO: 1319), CeresAnnot:1526950 (SEQ ID NO: 1321), CeresClone:1832333 (SEQ ID NO: 1323), GI:74272607 (SEQ ID NO: 1324), GI:192910782 (SEQ ID NO: 1325), GI:157342563 (SEQ ID NO: 1326), GI:159483497 (SEQ ID NO: 1327), CeresClone:1839999 (SEQ ID NO: 1329), CeresClone:467335 (SEQ ID NO: 1333), GI:168010087 (SEQ ID NO: 1334), CeresClone:

1728202 (SEQ ID NO: 1336), CeresClone:1994239 (SEQ ID NO: 1338), CeresAnnot:8704704 (SEQ ID NO: 1342), GI:115453877 (SEQ ID NO: 1343), CeresClone:1646411 (SEQ ID NO: 1345), CeresClone:100920260 (SEQ ID NO: 1349), GI:116786147 (SEQ ID NO: 1350), GI:116783944 (SEQ ID NO: 1351), GI:82623397 (SEQ ID NO: 1354), CeresAnnot:8656662 (SEQ ID NO: 1356), CeresClone: 1417803 (SEQ ID NO: 1358), and GI:145345927 (SEQ ID NO: 1361).

D. Percent Identity

In some embodiments, a heat and/or drought-tolerance polypeptide has an amino acid sequence with at least 20% sequence identity, e.g., 21%, 22%, 24%, 27%, 30%, 33%, 38%, 45%, 46%, 49%, 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:442, SEQ ID NO:489, SEQ ID NO:568, SEQ ID NO:590, SEQ ID NO:705, SEQ ID NO:711, SEQ ID NO:742, SEQ ID NO:1012, SEQ ID NO:1129, SEQ ID NO:60, SEQ ID NO:364, SEQ ID NO:311, SEQ ID NO:160, SEQ ID NO:2, SEQ ID NO:749, SEQ ID NO: 1131, and SEQ ID NO:57. Polypeptides having such a percent sequence identity often have a domain indicative of a heat and/or drought-tolerance polypeptide and/or have an HMM bit score that is greater than 20, as discussed above. Amino acid sequences of heat and/or drought-tolerance polypeptides having at least 20% sequence identity to one of the amino acid sequences set forth in SEQ ID NO:442, SEQ ID NO:489, SEQ ID NO:568, SEQ ID NO:590, SEQ ID NO:705, SEQ ID NO:711, SEQ ID NO:742, SEQ ID NO:1012, SEQ ID NO:1129, SEQ ID NO:60, SEQ ID NO:364, SEQ ID NO:311, SEQ ID NO:160, SEQ ID NO:2, SEQ ID NO: 1131, and SEQ ID NO:749 are provided in FIGS. 1-16.

"Percent sequence identity" refers to the degree of sequence identity between any given reference sequence, e.g., SEQ ID NO:2, and a candidate heat and/or drought-tolerance sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10; gap extension penalty: 0.5; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a drought-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:442. Amino acid sequences of polypeptides having greater than 40% sequence identity to the polypeptide set forth in SEQ ID NO:442 are provided in FIG. 1. Such polypeptides include Public GI ID no. 72384401 (SEQ ID NO:443), Ceres CLONE ID no. 1079382 (SEQ ID NO:445), Ceres CLONE ID no. 1853461 (SEQ ID NO:447), Ceres CLONE ID no. 1626485 (SEQ ID NO:451), Ceres CLONE ID no. 1713920 (SEQ ID NO:459), Ceres CLONE ID no. 1772747 (SEQ ID NO:463), Ceres CLONE ID no. 225960 (SEQ ID NO:465), Public GI ID no. 115443807 (SEQ ID NO:470), and Ceres CLONE ID no. 569388 (SEQ ID NO:483).

In some cases, a drought-tolerance polypeptide has an amino acid sequence with at least 30% sequence identity, e.g., 30%, 35%, 40%, 48%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:489 Amino acid sequences of polypeptides having greater than 30% sequence identity to the polypeptide set forth in SEQ ID NO:489 are provided in FIG. 2. Such polypeptides include Ceres CLONE ID no. 571200 (SEQ ID NO:494), Ceres CLONE ID no. 1928532 (SEQ ID NO:496), Ceres ANNOT ID no. 1490637 (SEQ ID NO:498), Ceres CLONE ID no. 295496 (SEQ ID NO:514), Public GI ID no. 115463637 (SEQ ID NO:515), and Ceres CLONE ID no. 1999444 (SEQ ID NO:518).

In some cases, a drought-tolerance polypeptide has an amino acid sequence with at least 35% sequence identity, e.g., 37%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:568. Amino acid sequences of polypeptides having greater than 35% sequence identity to the polypeptide set forth in SEQ ID NO:568 are provided in FIG. 3. Such polypeptides include Ceres CLONE ID no. 695006 (SEQ ID NO:578) and Ceres ANNOT ID no. 1527488 (SEQ ID NO:584).

In some cases, a drought-tolerance polypeptide has an amino acid sequence with at least 25% sequence identity, e.g., 28%, 32%, 40%, 44%, 48%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:590. Amino acid sequences of polypeptides having greater than 25% sequence identity to the polypeptide set forth in SEQ ID NO:590 are provided in FIG. 4. Such polypeptides include Ceres ANNOT ID no. 1501305 (SEQ ID NO:623), Ceres CLONE ID no. 607280 (SEQ ID NO:627), Public GI ID no. 92887174 (SEQ ID NO:632), Ceres CLONE ID no. 1857162 (SEQ ID NO:634), Public GI ID no. 115477272 (SEQ ID NO:674), and Ceres CLONE ID no. 264002 (SEQ ID NO:682).

In some cases, a drought-tolerance polypeptide has an amino acid sequence with at least 40% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:705. Amino acid sequences of polypeptides having greater than 40% sequence identity to the polypeptide set forth in SEQ ID NO:705 are provided in FIG. 5. Such polypeptides include Public GI ID no. 79320952 (SEQ ID NO:706) and Public GI ID no. 79320957 (SEQ ID NO:707).

In some cases, a drought-tolerance polypeptide has an amino acid sequence with at least 30% sequence identity, e.g., 33%, 41%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:711. Amino acid sequences of polypeptides having greater than 30% sequence identity to the polypeptide set forth in SEQ ID NO:711 are provided in FIG. 6. Such polypeptides include Ceres CLONE ID no. 964616 (SEQ ID NO:714), Ceres CLONE ID no. 100009667 (SEQ ID NO:715), Ceres ANNOT ID no. 1444568 (SEQ ID NO:719), Ceres CLONE ID no. 719489 (SEQ ID NO:725), Ceres CLONE ID no. 587748 (SEQ ID NO:733), Public GI ID no. 125528114 (SEQ ID NO:734), and Ceres CLONE ID no. 274172 (SEQ ID NO:737).

In some cases, a drought-tolerance polypeptide has an amino acid sequence with at least 30% sequence identity, e.g., 35%, 38%, 43%, 47%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:742 Amino acid sequences of polypeptides having greater than 30% sequence identity to the polypeptide set forth in SEQ ID NO:742 are provided in FIG. 7. Such polypeptides include Public GI ID no. 115477170 (SEQ ID NO:757), Ceres CLONE ID no. 1620215 (SEQ ID NO:759), Ceres CLONE ID no. 1931889 (SEQ ID NO:761), Ceres ANNOT ID no. 1460527 (SEQ ID NO:801), Ceres CLONE ID no. 975913 (SEQ ID NO:846), Ceres CLONE ID no. 708446 (SEQ ID NO:859), Ceres CLONE ID no. 1748922 (SEQ ID NO:944), Ceres CLONE ID no. 1775820 (SEQ ID NO:955), Public GI ID no. 115468934 (SEQ ID NO:991), and Public GI ID no. 118424243 (SEQ ID NO:1000).

In some cases, a drought-tolerance polypeptide has an amino acid sequence with at least 35% sequence identity, e.g., 36%, 40%, 47%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:1012 Amino acid sequences of polypeptides having greater than 35% sequence identity to the polypeptide set forth in SEQ ID NO:1012 are provided in FIG. 8. Such polypeptides include Ceres CLONE ID no. 287430 (SEQ ID NO:1018), Ceres ANNOT ID no. 451889 (SEQ ID NO:1020), Ceres CLONE ID no. 936084 (SEQ ID NO:1055), Ceres CLONE ID no. 1792501 (SEQ ID NO:1066), Ceres ANNOT ID no. 1437875 (SEQ ID NO:1068), Public GI ID no. 1853968 (SEQ ID NO:1093), Public GI ID no. 27530032 (SEQ ID NO:1094), Ceres CLONE ID no. 1834483 (SEQ ID NO:1110), Public GI ID no. 84579418 (SEQ ID NO:1113), Public GI ID no. 15077030 (SEQ ID NO:1117), and Public GI ID no. 13752458 (SEQ ID NO:1118).

In some cases, a drought-tolerance polypeptide has an amino acid sequence with at least 30% sequence identity, e.g., 31%, 35%, 40%, 41%, 49%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:1129 Amino acid sequences of polypeptides having greater than 30% sequence identity to the polypeptide set forth in SEQ ID NO:1129 are provided in FIG. 9. Such polypeptides include Public GI ID no. 72255610 (SEQ ID NO:933), Ceres SEEDLINE ID no. ME20095 (SEQ ID NO:1129), Ceres CLONE ID no. 1562633 (SEQ ID NO:1140), Ceres ANNOT ID no. 1692728 (SEQ ID NO:1142), Ceres CLONE ID no. 921110 (SEQ ID NO:1144), Ceres CLONE ID no. 1791180 (SEQ ID NO:1146), Ceres CLONE ID no. 527891 (SEQ ID NO:1148), Ceres ANNOT ID no. 1522414 (SEQ ID NO:1150), and Public GI ID no. 51458330 (SEQ ID NO:1182). In some cases, a heat-tolerance polypeptide has an amino acid sequence with at least 25% sequence identity, e.g., 26%, 27%, 30%, 32%, 40%, 42%, 47%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:60 Amino acid sequences of polypeptides having greater than 25% sequence identity to the polypeptide set forth in SEQ ID NO:60 are provided in FIG. 10. Such polypeptides include Ceres CLONE ID no. 872030 (SEQ ID NO:62), Ceres CLONE ID no. 100029223 (SEQ ID NO:74), Ceres CLONE ID no. 1939845 (SEQ ID NO:98), Ceres CLONE ID no. 2015383 (SEQ ID NO:102), Ceres CLONE ID no. 1607893 (SEQ ID NO:104), Ceres CLONE ID no. 1075133 (SEQ ID NO:152), and Ceres CLONE ID no. 1218065 (SEQ ID NO:915).

In some cases, a heat-tolerance polypeptide has an amino acid sequence with at least 25% sequence identity, e.g., 27%, 28%, 31%, 36%, 44%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:364 Amino acid sequences of polypeptides having greater than 25% sequence identity to the polypeptide set forth in SEQ ID NO:364 are provided in FIG. 11. Such polypeptides include Ceres ANNOT ID no. 1455221 (SEQ ID NO:407), Public GI ID no. 729774 (SEQ ID NO:408), Ceres CLONE ID no. 1414288 (SEQ ID NO:410), Public GI ID no. 115482048 (SEQ ID NO:413), and Public GI ID no. 56117815 (SEQ ID NO:421).

In some cases, a heat-tolerance polypeptide has an amino acid sequence with at least 25% sequence identity, e.g., 29%, 35%, 40%, 47%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:311. Amino acid sequences of polypeptides having greater than 25% sequence identity to the polypeptide set forth in SEQ ID NO:311 are provided in FIG. 12. Such polypeptides include Ceres ANNOT ID no. 1538958 (SEQ ID NO:319), Public GI ID no. 115521213 (SEQ ID NO:320), Public GI ID no. 42415865 (SEQ ID NO:321), Public GI ID no. 729775 (SEQ ID NO:322), Public GI ID no. 11386827 (SEQ ID NO:323), Public GI ID no. 115456675 (SEQ ID NO:326), and Public GI ID no. 89274218 (SEQ ID NO:335).

In some cases, a heat-tolerance polypeptide has an amino acid sequence with at least 25% sequence identity, e.g., 30%, 33%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:160. Amino acid sequences of polypeptides having greater than 25% sequence identity to the polypeptide set forth in SEQ ID NO:160 are provided in FIG. 13. Such polypeptides include Ceres CLONE ID no. 1837065 (SEQ ID NO:162), Ceres ANNOT ID no. 1531178 (SEQ ID NO:184), Ceres CLONE ID no. 470694 (SEQ ID NO:242), Public GI ID no. 92867368 (SEQ ID NO:253), Ceres CLONE ID no. 859707 (SEQ ID NO:256), Ceres CLONE ID no. 392275 (SEQ ID NO:268), Ceres CLONE ID no. 1828394 (SEQ ID NO:282), and Public GI ID no. 115466694 (SEQ ID NO:294).

In some cases, a heat-tolerance polypeptide has an amino acid sequence with at least 20% sequence identity, e.g., 21%, 22%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:2. Amino acid sequences of polypeptides having greater than 20% sequence identity to the polypeptide set forth in SEQ ID NO:2 are provided in FIG. 14. Such polypeptides include Public GI ID no. 115470807 (SEQ ID NO:5), Ceres CLONE ID no. 1842931 (SEQ ID NO:15), Ceres CLONE ID no. 321308 (SEQ ID NO:17), Ceres CLONE ID no. 1725811 (SEQ ID NO:19), Ceres CLONE ID no. 1357455 (SEQ ID NO:21), Ceres CLONE ID no. 943370 (SEQ ID NO:23), Ceres CLONE ID no. 1327712 (SEQ ID NO:25), Ceres CLONE ID no. 1764692 (SEQ ID NO:27), and Ceres ANNOT ID no. 1512656 (SEQ ID NO:41).

In some cases, a drought-tolerance polypeptide has an amino acid sequence with at least 20% sequence identity, e.g., 22%, 23%, 30%, 35%, 40%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:749. Amino acid sequences of polypeptides having greater than 20% sequence identity to the polypeptide set forth in SEQ ID NO:749 are provided in FIG. 15. Such polypeptides include Ceres CLONE ID no. 1847516 (SEQ ID NO:1195), Ceres CLONE ID no. 1961986 (SEQ ID NO:1201), and Ceres ANNOT ID no. 6091930 (SEQ ID NO:1207).

In some cases, a drought-tolerance polypeptide has an amino acid sequence with at least 30% sequence identity, e.g., 31%, 35%, 40%, 41%, 49%, 50%, 52%, 56%, 59%, 61%, 65%, 70%, 75%, 80%, 85%, 90%, 95%, 97%, 98%, or 99% sequence identity, to the amino acid sequence set forth in SEQ ID NO:1311 Amino acid sequences of polypeptides having greater than 30% sequence identity to the polypeptide set forth in SEQ ID NO:1311 are provided in FIG. 16. Such polypeptides include CeresClone:971761 (SEQ ID NO: 1313), CeresClone:1946574 (SEQ ID NO: 1331), CeresClone:2055551 (SEQ ID NO: 1340), CeresClone:100045499 (SEQ ID NO: 1347), CeresClone:1465853 (SEQ ID NO: 1353), CeresClone:753982 (SEQ ID NO: 1360), CeresClone:1076093 (SEQ ID NO: 1315), CeresClone:1627875 (SEQ ID NO: 1317), CeresAnnot:1508362 (SEQ ID NO: 1319), CeresAnnot:1526950 (SEQ ID NO: 1321), CeresClone:1832333 (SEQ ID NO: 1323), GI:74272607 (SEQ ID NO: 1324), GI:192910782 (SEQ ID NO: 1325), GI:157342563 (SEQ ID NO: 1326), GI:159483497 (SEQ ID NO: 1327), CeresClone:1839999 (SEQ ID NO: 1329), CeresClone:467335 (SEQ ID NO: 1333), GI:168010087 (SEQ ID NO: 1334), CeresClone:1728202 (SEQ ID NO: 1336), CeresClone:1994239 (SEQ ID NO: 1338), CeresAnnot:8704704 (SEQ ID NO: 1342), GI:115453877 (SEQ ID NO: 1343), CeresClone:1646411 (SEQ ID NO: 1345), CeresClone:100920260 (SEQ ID NO: 1349), GI:116786147 (SEQ ID NO: 1350), GI:116783944 (SEQ ID NO: 1351), GI:82623397 (SEQ ID NO: 1354), CeresAnnot:8656662 (SEQ ID NO: 1356), CeresClone:1417803 (SEQ ID NO: 1358), and GI:145345927 (SEQ ID NO: 1361).

E. Other Sequences

It should be appreciated that a heat and/or drought-tolerance polypeptide can include additional amino acids that are not involved in heat and/or drought-tolerance, and thus such a polypeptide can be longer than would otherwise be the case. For example, a heat and/or drought-tolerance polypeptide can include a purification tag, a chloroplast transit peptide, a mitochondrial transit peptide, an amyloplast peptide, or a leader sequence added to the amino or carboxy terminus. In some embodiments, a heat and/or drought-tolerance polypeptide includes an amino acid sequence that functions as a reporter, e.g., a green fluorescent protein or yellow fluorescent protein.

III. NUCLEIC ACIDS

Nucleic acids described herein include nucleic acids that are effective to increase heat and/or drought tolerance when transcribed in a plant or plant cell. Such nucleic acids include those that encode a heat and/or drought-tolerance polypeptide.

A. Nucleic Acids Encoding Heat and/or Drought-Tolerance Polypeptides

Nucleic acids encoding heat and/or drought-tolerance polypeptides are described herein. Such nucleic acids include SEQ ID NO:441, SEQ ID NO:488, SEQ ID NO:567, SEQ ID NO:589, SEQ ID NO:703, SEQ ID NO:704, SEQ ID NO:710, SEQ ID NO:1241, SEQ ID NO:1260, SEQ ID NO:1126, SEQ ID NO:1127, SEQ ID NO:1128, SEQ ID NO:58, SEQ ID NO:59, SEQ ID NO:363, SEQ ID NO:310, SEQ ID NO:159, SEQ ID NO:1, and SEQ ID NO:56, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:441, SEQ ID NO:488, SEQ ID NO:567, SEQ ID NO:589, SEQ ID NO:703, SEQ ID NO:704, SEQ ID NO:710, SEQ ID NO:1241, SEQ ID NO:1260, SEQ ID NO:1126, SEQ ID NO:1127, SEQ ID NO:1128, SEQ ID NO:58, SEQ ID NO:59, SEQ ID NO:363, SEQ ID NO:310, SEQ ID NO:159, SEQ ID NO:1, SEQ ID NO:1008, and SEQ ID NO:56.

A drought-tolerance nucleic acid can comprise the nucleotide sequence set forth in SEQ ID NO:441. Alternatively, a drought-tolerance nucleic acid can be a variant of the nucleic acid having the nucleotide sequence set forth in SEQ ID NO:441. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:441 or a functional homolog thereof such as those identified in the sequence listing.

A drought-tolerance nucleic acid can comprise the nucleotide sequence set forth in SEQ ID NO:488. Alternatively, a drought-tolerance nucleic acid can be a variant of the nucleic acid having the nucleotide sequence set forth in SEQ ID NO:488. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:488 or a functional homolog thereof such as those identified in the sequence listing.

A drought-tolerance nucleic acid can comprise the nucleotide sequence set forth in SEQ ID NO:567. Alternatively, a drought-tolerance nucleic acid can be a variant of the nucleic acid having the nucleotide sequence set forth in SEQ ID NO:567. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:567 or a functional homolog thereof such as those identified in the sequence listing.

A drought-tolerance nucleic acid can comprise the nucleotide sequence set forth in SEQ ID NO:589. Alternatively, a drought-tolerance nucleic acid can be a variant of the nucleic acid having the nucleotide sequence set forth in SEQ ID NO:589. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:589 or a functional homolog thereof such as those identified in the sequence listing.

A drought-tolerance nucleic acid can comprise the nucleotide sequence set forth in SEQ ID NO:703. Alternatively, a drought-tolerance nucleic acid can be a variant of the nucleic acid having the nucleotide sequence set forth in SEQ ID NO:703. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:703 or a functional homolog thereof such as those identified in the sequence listing.

A drought-tolerance nucleic acid can comprise the nucleotide sequence set forth in SEQ ID NO:710. Alternatively, a drought-tolerance nucleic acid can be a variant of the nucleic acid having the nucleotide sequence set forth in SEQ ID NO:710. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:710 or a functional homolog thereof such as those identified in the sequence listing.

A drought-tolerance nucleic acid can comprise the nucleotide sequence set forth in SEQ ID NO:1241. Alternatively, a drought-tolerance nucleic acid can be a variant of the nucleic acid having the nucleotide sequence set forth in SEQ ID NO:1241. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1241 or a functional homolog thereof such as those identified in the sequence listing.

A drought-tolerance nucleic acid can comprise the nucleotide sequence set forth in SEQ ID NO:1260. Alternatively, a drought-tolerance nucleic acid can be a variant of the nucleic acid having the nucleotide sequence set forth in SEQ ID NO:1260. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1260 or a functional homolog thereof such as those identified in the sequence listing.

A drought-tolerance nucleic acid can comprise the nucleotide sequence set forth in SEQ ID NO:1126. Alternatively, a drought-tolerance nucleic acid can be a variant of the nucleic acid having the nucleotide sequence set forth in SEQ ID NO:1126. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1126 or a functional homolog thereof such as those identified in the sequence listing.

A heat-tolerance nucleic acid can comprise the nucleotide sequence set forth in SEQ ID NO:58. Alternatively, a heat-tolerance nucleic acid can be a variant of the nucleic acid having the nucleotide sequence set forth in SEQ ID NO:58. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:58 or a functional homolog thereof such as those identified in the sequence listing.

A heat-tolerance nucleic acid can comprise the nucleotide sequence set forth in SEQ ID NO:363. Alternatively, a heat-tolerance nucleic acid can be a variant of the nucleic acid having the nucleotide sequence set forth in SEQ ID NO:363. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:363 or a functional homolog thereof such as those identified in the sequence listing.

A heat-tolerance nucleic acid can comprise the nucleotide sequence set forth in SEQ ID NO:310. Alternatively, a heat-tolerance nucleic acid can be a variant of the nucleic acid having the nucleotide sequence set forth in SEQ ID NO:310. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:310 or a functional homolog thereof such as those identified in the sequence listing.

A heat-tolerance nucleic acid can comprise the nucleotide sequence set forth in SEQ ID NO:159. Alternatively, a heat-tolerance nucleic acid can be a variant of the nucleic acid having the nucleotide sequence set forth in SEQ ID NO:159. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:159 or a functional homolog thereof such as those identified in the sequence listing.

A heat-tolerance nucleic acid can comprise the nucleotide sequence set forth in SEQ ID NO:1. Alternatively, a heat-tolerance nucleic acid can be a variant of the nucleic acid having the nucleotide sequence set forth in SEQ ID NO:1. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1 or a functional homolog thereof such as those identified in the sequence listing.

A drought-tolerance nucleic acid can comprise the nucleotide sequence set forth in SEQ ID NO:1008. Alternatively, a drought-tolerance nucleic acid can be a variant of the nucleic acid having the nucleotide sequence set forth in SEQ ID NO:1008. For example, a drought-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1008 or a functional homolog thereof such as those identified in the sequence listing.

A heat-tolerance nucleic acid can comprise the nucleotide sequence set forth in SEQ ID NO:56. Alternatively, a heat-tolerance nucleic acid can be a variant of the nucleic acid having the nucleotide sequence set forth in SEQ ID NO:56. For example, a heat-tolerance nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:56.

A drought-tolerance nucleic acid can comprise the nucleotide sequence set forth in SEQ ID NO:1362. Alternatively, a drought-tolerance nucleic acid can be a variant of the nucleic acid having the nucleotide sequence set forth in SEQ ID NO:1362. For example, a drought-tolerance nucleic acid can have a nucleotide sequence with at least 30% sequence identity, e.g., 35%, 40%, 45%, 50%, 55%, 60%, 65%, 70%, 75%, 80%, 85%, 90%, 95%, 97%, 98%, or 99% sequence identity, to the nucleotide sequence set forth in SEQ ID NO:1362 or a functional homolog thereof such as those identified in the sequence listing.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides

Expression of a Heat and/or Drought-Tolerance Polypeptide

A nucleic acid encoding one of the heat and/or drought-tolerance polypeptides described herein can be used to express the polypeptide in a plant species of interest, typically by transforming a plant cell with a nucleic acid having the coding sequence for the polypeptide operably linked in sense orientation to one or more regulatory regions. Suitable polynucleotides include full-length nucleic acids encoding heat and/or drought-tolerance polypeptides or fragments of such full-length nucleic acids. In some embodiments, a complement of the full-length nucleic acid or a fragment thereof can be used. Typically, a fragment is at least 50 nucleotides, e.g., at least 50, 55, 60, 75, 100, 200, 300, 500, 600, 700, 1000, 2000 nucleotides or more.

It will be appreciated that because of the degeneracy of the genetic code, a number of nucleic acids can encode a particular heat and/or drought-tolerance polypeptide; i.e., for many amino acids, there is more than one nucleotide triplet that serves as the codon for the amino acid. Thus, codons in the coding sequence for a given heat and/or drought-tolerance polypeptide can be modified such that optimal expression in a particular plant species is obtained, using appropriate codon bias tables for that species.

In some cases, expression of a heat and/or drought-tolerance polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

C. Constructs/Vectors

Recombinant constructs provided herein can be used to transform plants or plant cells in order to increase drought and/or heat tolerance. A recombinant nucleic acid construct can comprise a nucleic acid encoding a heat and/or drought-tolerance polypeptide as described herein, operably linked to a regulatory region suitable for expressing the heat and/or drought-tolerance polypeptide in the plant or cell. Thus, a nucleic acid can comprise a coding sequence that encodes any of the heat and/or drought-tolerance polypeptides as set forth in SEQ ID NO: 2, 3, 4, 5, 6, 7, 8, 9, 10, 11, 13, 15, 17, 19, 21, 23, 25, 27, 29, 31, 33, 35, 37, 39, 41, 43, 45, 47, 49, 51, 53, 55, 57, 60, 62, 63, 64, 65, 66, 67, 68, 69, 70, 71, 73, 74, 76, 78, 80, 82, 84, 86, 88, 90, 92, 94, 96, 98, 100, 102, 104, 106, 108, 110, 112, 114, 116, 118, 120, 122, 124, 126, 127, 130, 132, 134, 136, 138, 139, 142, 144, 146, 148, 150, 152, 154, 156, 158, 160, 162, 164, 166, 168, 170, 172, 174, 176, 178, 179, 180, 182, 184, 186, 188, 190, 192, 194, 196, 198, 200, 202, 204, 206, 208, 209, 212, 214, 216, 218, 220, 222, 224, 225, 228, 229, 231, 233, 234, 235, 237, 239, 240, 242, 244, 246, 248, 250, 252, 253, 254, 256, 258, 260, 262, 264, 266, 268, 269, 271, 273, 275, 277, 279, 280, 282, 284, 286, 288, 289, 290, 291, 292, 293, 294, 295, 296, 297, 298, 299, 300, 301, 302, 303, 304, 305, 307, 309, 311, 312, 314, 315, 316, 317, 319, 320, 321, 322, 323, 325, 326, 327, 329, 330, 332, 334, 335, 336, 337, 338, 339, 340, 341, 343, 344, 346, 348, 349, 350, 351, 353, 355, 356, 358, 360, 362, 364, 366, 368, 369, 370, 371, 373, 375, 377, 379, 381, 383, 385, 387, 389, 390, 392, 394, 396, 398, 400, 401, 402, 404, 405, 407, 408, 410, 412, 413, 414, 416, 418, 419, 420, 421, 422, 423, 424, 426, 428, 430, 431, 432, 433, 434, 435, 436, 438, 440, 442, 443, 445, 447, 449, 451, 453, 455, 457, 459, 461, 463, 465, 467, 469, 470, 472, 474, 476, 478, 480, 481, 483, 485, 487, 489, 490, 491, 492, 494, 496, 498, 500, 502, 504, 506, 508, 510, 512, 514, 515, 516, 518, 519, 520, 522, 524, 526, 528, 530, 531, 533, 535, 536, 538, 540, 541, 543, 545, 547, 548, 550, 552, 553, 555, 557, 558, 559, 561, 562, 564, 566, 568, 569, 570, 572, 574, 576, 578, 580, 582, 584, 586, 588, 590, 591, 592, 593, 594, 595, 596, 597, 598, 599, 600, 602, 603, 604, 605, 607, 608, 610, 612, 614, 615, 616, 617, 618, 619, 620, 621, 623, 625, 627, 629, 631, 632, 634, 635, 636, 638, 640, 642, 644, 646, 647, 648, 650, 651, 653, 654, 655, 656, 658, 660, 661, 662, 663, 664, 665, 666, 667, 668, 669, 671, 673, 674, 675, 676, 678, 680, 682, 684, 685, 687, 688, 690, 691, 692, 694, 696, 698, 700, 702, 705, 706, 707, 708, 709, 711, 712, 714, 715, 717, 719, 721, 723, 725, 726, 727, 729, 731, 733, 734, 735, 737, 738, 740, 741, 742, 743, 744, 745, 746, 747, 748, 749, 751, 752, 753, 754, 755, 756, 757, 759, 760, 761, 763, 765, 767, 768, 769, 771, 773, 774, 775, 777, 779, 781, 783, 785, 787, 789, 791, 793, 795, 796, 797, 798, 799, 801, 803, 805, 807, 808, 809, 810, 811, 812, 813, 815, 816, 817, 819, 821, 823, 825, 827, 829, 832, 834, 836, 839, 840, 841, 842, 843, 844, 845, 846, 848, 849, 850, 851, 852, 853, 854, 856, 857, 859, 861, 863, 865, 867, 869, 870, 871, 872, 873, 874, 876, 878, 880, 882, 885, 886, 887, 888, 889, 890, 891, 892, 893, 894, 896, 897, 898, 900, 901, 902, 904, 906, 908, 910, 912, 913, 914, 915, 916, 918, 920, 922, 924, 926, 929, 931, 932, 933, 935, 937, 939, 941, 943, 944, 945, 947, 949, 951, 952, 953, 955, 957, 958, 959, 960, 961, 962, 963, 964, 966, 968, 969, 970, 971, 973, 974, 975, 977, 978, 979, 980, 981, 983, 985, 987, 988, 989, 990, 991, 992, 993, 995, 997, 998, 999, 1000, 1001, 1003, 1005, 1007, 1010, 1012, 1013, 1014, 1015, 1016, 1018, 1020, 1022, 1023, 1025, 1027, 1028, 1030, 1031, 1033, 1035, 1037, 1039, 1041, 1043, 1045, 1046, 1048, 1050, 1051, 1053, 1055, 1056, 1058, 1059, 1061, 1062, 1064, 1066, 1068, 1069, 1071, 1073, 1075, 1077, 1079, 1080, 1082, 1084, 1086, 1088, 1090, 1092, 1093, 1094, 1096, 1098, 1100, 1102, 1104, 1106, 1108, 1110, 1112, 1113, 1114, 1116, 1117, 1118, 1119, 1121, 1123, 1125, 1129, 1130, 1131, 1132, 1133, 1134, 1135, 1136, 1137, 1138, 1140, 1142, 1144, 1146, 1148, 1150, 1151, 1152, 1153, 1154, 1156, 1157, 1158, 1159, 1160, 1161, 1162, 1164, 1166, 1168, 1170, 1172, 1174, 1175, 1177, 1179, 1181, 1182, 1184, 1186, 1188, 1189, 1191, 1193, 1195, 1197, 1199, 1201, 1203, 1205, 1207, 1209, 1210, 1212, 1214, 1215, 1216, 1218, 1219, 1221, 1222, 1223, 1225, 1226, 1228, 1230, 1231, 1232, 1234, 1236, 1238, 1240, 1242, 1244, 1246, 1248, 1250, 1252, 1254, 1256, 1258, 1262, 1264, 1265, 1267, 1269, 1271, 1273, 1274, 1276, 1277, 1279, 1281, 1283, 1285, 1286, 1287, 1288, 1290, 1292, 1293, 1294, 1296, 1298, 1300, 1302, 1304, 1305, 1311, 1313, 1315, 1317, 1319, 1321, 1323, 1324, 1325, 1326, 1327, 1329, 1331, 1333, 1334, 1336, 1338, 1340, 1342, 1343, 1345, 1347, 1349, 1350, 1351, 1353, 1354, 1356, 1358, 1360, or 1361. The heat and/or drought-tolerance polypeptide encoded by a recombinant nucleic acid can be a native heat and/or drought-tolerance polypeptide, or can be heterologous to the cell. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al., *Nature Biotech* 17: 287-291 (1999)).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al., *Journal of New Seeds* 5:209-221 (2003)).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a heat and/or drought-tolerance polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous heat and/or drought-tolerance polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a heat and/or drought-tolerance polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as increased drought tolerance or increased heat tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in heat and/or drought tolerance relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp. or hybrids thereof, *Sorghum* spp. or hybrids thereof, sudangrass, *Miscanthus* spp. or hybrids thereof, *Saccharum* spp. or hybrids thereof, *Erianthus* spp., *Populus* spp., *Andropogon gerardii* (big bluestem), *Pennisetum purpureum* (elephant grass) or hybrids thereof (e.g., *Pennisetum purpureum* x *Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrids thereof, *Secale cereale* (rye), *Salix* spp. (willow), *Eucalyptus* spp. (eucalyptus), *Triticosecale* (*Triticum*—wheat X rye), *Tripsicum dactyloides* (Eastern gammagrass), *Leymus cinereus* (basin wildrye), *Leymus condensatus* (giant wildrye), and bamboo.

In some embodiments, a suitable species can be a wild, weedy, or cultivated sorghum species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoi-*

*deum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x *sudangrass* or *Sorghum* x *drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea spp., Andrographis paniculata, Atropa belladonna, Datura stomonium, Berberis* spp., *Cephalotaxus* spp., *Ephedra sinica, Ephedra* spp *Erythroxylum coca, Galanthus wornorii, Scopolia* spp., *Lycopodium serratum* (=*Huperzia serrata*), *Lycopodium* spp *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. x *Miscanthus* sp., *Saccharum* sp. x *Sorghum* sp., *Panicum virgatum* x *Panicum amarum, Panicum virgatum* x *Panicum amarulum*, and *Pennisetum purpureum* x *Pennisetum typhoidum*).

D. Transgenic Plant Phenotypes

In some embodiments, a plant in which expression of a heat and/or drought-tolerance polypeptide is modulated can have increased heat tolerance or drought tolerance. In some cases, a plant in which expression of a heat and/or drought-tolerance polypeptide is modulated can exhibit both heat tolerance and drought tolerance. The phenotype of a transgenic plant in which expression of a heat and/or drought-tolerance polypeptide is modulated and a corresponding control plant that either lacks the transgene or does not express the transgene can be evaluated under particular environmental conditions that are useful for simulating drought conditions. The phenotype of a transgenic plant in which expression of a heat and/or drought-tolerance polypeptide is modulated and a corresponding control plant can also be evaluated under heat shock conditions.

For example, a heat and/or drought-tolerance polypeptide described herein can be expressed in a transgenic plant, resulting in increased growth as compared to a plant that does not express the polypeptide when grown under drought conditions or heat shock conditions, or following such conditions. Growth can be assessed with physiological parameters such as, for example, plant height, number of new shoots, number of new leaves, leaf length, seedling area, or seed number.

In some cases, a transgenic plant expressing a heat and/or drought tolerance polypeptide described herein can exhibit a height that is from about 5% to about 100% greater (e.g., about 5% to about 12%; about 5% to about 40%; about 5% to about 80%; about 7% to about 20%; about 10% to about 15%; about 10% to about 50%; about 10% to about 90%; about 20% to about 25%; about 20% to about 45%; about 20% to about 75%; about 25% to about 60%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than a plant not expressing the polypeptide when grown under drought conditions or heat shock conditions, or following such conditions.

In some instances, a transgenic plant expressing a heat and/or drought-tolerance polypeptide can exhibit greater leaf area or greater leaf length than a corresponding control plant that does not express the polypeptide when grown under heat shock conditions or drought conditions, or following such conditions. For example, a transgenic plant expressing a heat and/or drought-tolerance polypeptide can have a leaf area that is 5% to about 100% greater (e.g., about 5% to about 7%; about 5% to about 20%; about 8% to about 80%; about 10% to about 20%; about 10% to about 25%; about 10% to about 50%; about 10% to about 90%; about 15% to about 25%; about 20% to about 45%; about 20% to about 70%; about 25% to about 40%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%;

or about 95% to about 100% greater) than a corresponding control plant that does not express the polypeptide when grown under heat shock conditions or drought conditions, or following such conditions. In another example, a transgenic plant expressing a heat and/or drought-tolerance polypeptide can have a leaf length that is from about 5% to about 100% greater (e.g., about 5% to about 12%; about 5% to about 40%; about 5% to about 80%; about 7% to about 20%; about 10% to about 15%; about 10% to about 50%; about 10% to about 90%; about 20% to about 25%; about 20% to about 45%; about 20% to about 75%; about 25% to about 60%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than a corresponding control plant that does not express the polypeptide when grown under heat shock conditions or drought conditions, or following such conditions.

In other cases, when a polypeptide described herein is expressed in a transgenic plant, the transgenic plant can exhibit a seed number (number of seeds per plant) from about 10% to about 95% greater (e.g., from about 10% to about 20%; from about 10% to about 50%; from about 10% to about 70%; from about 20% to about 60%; from about 20% to about 75%; from about 25% to about 85%; from about 30% to about 70%; from about 35% to about 90%; from about 40% to about 60%; from about 40% to about 85%; from about 50% to about 80%; from about 50% to about 90%; or from about 70% to about 90% greater) than a control plant not expressing the polypeptide when grown under heat shock conditions or drought conditions. In certain cases, when a polypeptide described herein is expressed in a transgenic plant, the transgenic plant can exhibit an increase in seed weight per plant from about 5% to about 100% greater (e.g., about 5% to about 12%; about 5% to about 40%; about 5% to about 80%; about 7% to about 20%; about 10% to about 15%; about 10% to about 50%; about 10% to about 90%; about 20% to about 25%; about 20% to about 45%; about 20% to about 75%; about 25% to about 60%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than the seed weight in a plant not expressing the polypeptide when grown under heat shock conditions or drought conditions.

Transgenic plants expressing a heat and/or drought-tolerance polypeptide also can exhibit a lower transpiration rate compared to control plants of the same genetic background. Transpiration rate is another physiological parameter that is indicative of how well a plant can tolerate drought conditions. For example, plants with a low transpiration rate are expected to lose water more slowly than plants with higher transpiration rates and therefore would be expected to better withstand drought conditions (i.e., have better drought tolerance). When a polypeptide described herein is expressed in a transgenic plant, the transgenic plant can exhibit a transpiration rate that is reduced by about 0.25% to 100% (e.g., 0.27%, 0.3%, 0.43%, 0.55%, 0.7%, 0.99%, 1%, 2%, 4%, 6%, 8%, 10%, 12%, 15%, 18%, 22%, 28%, 35%, 37%, 42%, 45%, 47%, 50%, 55%, 64%, 68%, 71%, 75%, 77%, 80%, 83%, 86%, 89%, 90%, 92%, 95%, 98%, or 99%) as compared to the transpiration rate in a corresponding control plant when grown under drought conditions.

In some cases, a transgenic plant expressing a heat and/or drought-tolerance polypeptide described herein can exhibit a decreased change in photosynthetic activity ($\Delta Fv/Fm$) after exposure to heat shock conditions as compared to a corresponding control plant that does not express the polypeptide when grown under the same conditions. In some cases, a transgenic plant expressing a heat and/or drought-tolerance polypeptide described herein can exhibit an increased change in photosynthetic activity ($\Delta Fv/Fm-D_2$) two days post heat-shock treatment as compared to a corresponding control plant that does not express the polypeptide when grown under the same conditions. For example, a transgenic plant expressing a heat and/or drought-tolerance polypeptide can exhibit a $\Delta Fv/Fm$ of from about 0.1 to about 0.8 (e.g., about 0.2 to about 0.28; about 0.2 to about 0.32; about 0.22 to about 0.35; about 0.29 to about 0.4; about 0.3 to about 0.45; about 0.33 to about 0.41; about 0.35 to about 0.5; about 0.4 to about 0.8; about 0.46 to about 0.52; about 0.5 to about 0.65; about 0.5 to about 0.8; about 0.6 to about 0.7; about 0.6 to about 0.9; about 0.65 to about 0.75; about 0.7 to about 0.9; or about 0.75 to about 0.8) or a $\Delta Fv/Fm-D_2$ range of from about 0.03 to about 0.8 (e.g., about 0.03 to about 0.08; about 0.03 to about 0.032; about 0.04 to about 0.05; about 0.09 to about 0.4; about 0.05 to about 0.5; about 0.075 to about 0.1; about 0.08 to about 0.2; about 0.3 to about 0.45; about 0.33 to about 0.41; about 0.35 to about 0.5; about 0.4 to about 0.8; about 0.46 to about 0.52; about 0.5 to about 0.65; about 0.5 to about 0.8; about 0.6 to about 0.7; about 0.6 to about 0.9; about 0.65 to about 0.75; about 0.7 to about 0.9; about 0.75 to about 0.85; or about 0.8 to about 0.9). In some embodiments, photosynthetic activity can be reduced by about 0.25% to about 100% (e.g., about 0.25% to about 0.4%, about 0.25% to about 1%, about 0.25% to about 5%, about 0.5% to about 10%, about 1% to about 5%, about 1% to about 10%, about 2% to about 8%, about 3% to about 20%, about 5% to about 7%; about 5% to about 20%; about 5% to about 45%, about 8% to about 80%; about 10% to about 20%; about 10% to about 25%; about 10% to about 50%; about 10% to about 90%; about 15% to about 25%; about 20% to about 45%; about 20% to about 70%; about 25% to about 40%; about 25% to about 99%; about 30% to about 50%; about 30% to about 70%; about 40% to about 50%; about 45% to about 60%; about 50% to about 80%; about 55% to about 75%; about 60% to about 80%; about 60% to about 95%; about 75% to about 99%; about 80% to about 99%; about 90% to about 95%; or about 95% to about 100%) as compared to the photosynthetic activity in a corresponding control plant following heat shock conditions.

Typically, a difference in the heat and/or drought tolerance in a transgenic plant relative to a control plant is considered statistically significant at $p \leq 0.05$ with an appropriate parametric or non-parametric statistic, e.g., Chi-square test, Student's t-test, Mann-Whitney test, or F-test. In some embodiments, a difference in the heat and/or drought tolerance is statistically significant at $p<0.1$, $p<0.05$, or $p<0.01$.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.1%, or 0.01%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can increase heat and/or drought tolerance is useful in plant breeding, because genetic polymorphisms exhibiting a degree of linkage with loci for such polypeptides are more likely to be correlated with variation in heat and/or drought tolerance. For example, genetic polymorphisms linked to the loci for such polypeptides are more likely to be useful in marker-assisted breeding programs to create lines having increased heat and/or drought tolerance.

Thus, one aspect of the invention includes methods of identifying whether one or more genetic polymorphisms are associated with heat and/or drought tolerance. Such methods involve determining whether genetic polymorphisms in a given population exhibit linkage with the locus for one of the polypeptides depicted in FIGS. 1-16 and/or a functional homolog thereof. The correlation is measured between variation in heat and/or drought tolerance in plants of the population and the presence of the genetic polymorphism(s) in plants of the population, thereby identifying whether or not the genetic polymorphism(s) are associated with variation for the trait. If the presence of a particular allele is statistically significantly correlated with a modulation in heat and/or drought tolerance, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, U. H. Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescin) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., PstI). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have increased heat and/or drought tolerance. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, other biofuel molecules, and/or sugar-derived co-products per kilogram of plant material, relative to control plants. By providing higher yields higher yields under environmentally stressful conditions such as drought conditions and/or heat shock conditions, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. EXAMPLES

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

Nucleic acids were isolated from *Arabidopsis thaliana* plants, and cloned into a Ti plasmid vector, CRS338, under the control of a 35S promoter, p32449 promoter, or p326 promoter, as indicated. Each construct contained a phosphinothricin acetyltransferase gene which confers Finale™ resistance to transformed plants. Wild-type *Arabidopsis thaliana* ecotype Wassilewskija (Ws) plants were transformed separately with each construct. The transformations were performed essentially as described in Bechtold et al., *C. R. Acad. Sci. Paris,* 316:1194-1199 (1993).

Transgenic *Arabidopsis* lines containing SEQ ID NO:441, SEQ ID NO:488, SEQ ID NO:567, SEQ ID NO:589, SEQ ID NO:704, SEQ ID NO:710, SEQ ID NO:1241, SEQ ID NO:1260, SEQ ID NO:1128, SEQ ID NO:59, SEQ ID NO:363, SEQ ID NO:310, SEQ ID NO:159, SEQ ID NO:1, SEQ ID NO:1008, or SEQ ID NO:56 were designated ME00029, ME00045, ME02190, ME02549, ME02865, ME03227, ME04477, ME18396, ME20095, ME02932, ME18240, ME20867, ME03268, ME06551, Ceres Clone ID No. 100021678, or ME06919, respectively. The presence of each vector containing a nucleic acid described above in the respective transgenic *Arabidopsis* line transformed with the vector was confirmed by Finale™ resistance, PCR amplification from green leaf tissue extract, and/or sequencing of PCR products.

Example 2—Screening for Drought Tolerance in Transgenic *Arabidopsis* Seedlings Soil was made from 60% Sunshine Mix #5 (Sun Gro; Bellevue, Wash., USA) and 40% vermiculite. For each superpool, 3 flats were seeded with about 3000 seeds. Prior to seeding, each flat was watered with 2 L of filtered water and the surface was misted. The flats were covered with a humidity dome and kept in the dark at 4° C. for 3 days.

After 3 days of cold treatment, the flats covered with humidity domes were transferred to a greenhouse and covered with a shade cloth (day 1). The humidity domes were removed on day 4, or when cotyledons are fully expanded. Each flat was watered with 2 L water within 1 day of removing the humidity domes by adding filtered water to the bottom of the flat and allowing 30-45 minutes for absorption of the water. On days 6 and 8, the flats were assessed for Finale™ resistance. On day 10, the no-hole flats were removed from the bottom of each flat to speed soil drying. The flats were watered in no-hole flats as above after 2.5 weeks and 4 weeks. Candidates with increased height, increased branching, normal siliques, larger rosettes, and persistent flowering, as compared to the wild-type Ws seedlings that were grown and treated in the same conditions were selected for analysis in a chronic soil drought assay.

Chronic Soil Drought Assay

Soil was made from 60% Sunshine Mix #5 (Sun Gro; Bellevue, Wash., USA) and 40% vermiculite. For each candidate event, 24 pots were prepared in a 24-pot no-hole flat with 28 grams of dry soil in each pot, and 4 L of filtered water was added to the tray. The water was allowed to soak into the soil and the soil surface was misted before seeding. For each candidate event, 18 pots were seeded with 3-5 seeds each of candidate seeds and 6 pots were seeded with 3-5 seeds each of wild-type control seeds. The seeded pots were covered with a humidity dome and kept in the dark at 4° C. for 3 days.

After 3 days of cold treatment, the pots covered with humidity domes were transferred to a Conviron® growth chamber set at 22° C., 16:8 hour light:dark cycle, 70% humidity, and 120 µE light intensity. The humidity domes were removed on day 5, or when cotyledons are fully expanded. After removal of the domes, each pot was irrigated to saturation with 0.5× Hoagland's solution, allowing the excess solution to drain. Seedlings were then thinned to 1 per pot. On day 8 or 9, the pots were irrigated to saturation with filtered water, allowing the excess water to drain after about 30 minutes of soaking, and the weight of each 24-pot flat was recorded. Each pot contained about 107 g water at saturation. Each pot was allowed to dry to about 15% of saturation between waterings. 30 g of water was added at each watering. Rosette area was measured at day 19. On day 24, plants were staked and measurements were taken of the longest leaf and the plant height. Terminal plant height was measured at the cease of flowering. The plants were allowed to dry and seed weight was measured. Finale resistance of a cauline leaf was determined at day 24. Significance of drought tolerance measurements was assessed using a one-tailed Student's t-test, assuming unequal variance, at $p \leq 0.5$.

Example 3—Screening for Heat Tolerance in Transgenic *Arabidopsis* Seedlings Agar plates were made from the media composed of 2.15 g/L MS salt (PhytoTechnology Laboratories®), 5 g/L sucrose (Sigma), 0.7% agar (PhytoTechnology Laboratories®), pH 5.7. For each superpool, 3000 seeds were sterilized using 30% Clorox containing 0.1% Triton X-100 and plated onto two agar plates at a density of 1500 seeds per plate. The plates were wrapped with vent tape and kept in the dark at 4° C. for 3 days.

After 3 days of stratification, the plates were transferred to a Conviron® growth chamber set at 22° C., 16:8 hour light:dark cycle, 70% humidity, and 60 µE light intensity. The seedlings were grown in the chamber for 3.5-4 days. For heat shock, the plates were placed in an incubator set at 47° C. for 2 hours. After heat shock, the plates were transferred back to the Conviron® growth chamber and the seedlings were allowed to recover and grow for several days (about 7 days). Candidates with enhanced root growth and greenness of leaves, faster emergence of photosynthetically active true leaves and increased size of rosettes, as compared to the wild-type Ws seedlings that were grown and treated in the same conditions were selected for analysis in a heat shock assay.

Heat Shock I Assay

Seeds were plated on heat germination agar plates containing 45 mL of half-strength MS medium (2.15 g MS salt (PhytoTechnology Laboratories®), 5 g sucrose (Sigma), and 0.7% agar (PhytoTechnology Laboratories®) per liter, pH 5.7) per Petri dish (square, 100 mm×15 mm) One transgenic event (40 seeds) and 9 wild-type Ws control seeds were plated on each plate. Plates were wrapped with vent tape and placed in the dark at 4° C. for 3 days. Plates were then transferred into a Conviron® growth chamber set at 22° C., 16:8 hour light:dark cycle, and 70% humidity with fluorescent lamps emitting a light intensity of about 60 µE.

After the plants were grown in the Conviron® growth chamber for 3-4 days, the plates were treated at 47° C. in a Yamato IC800 incubator for 1 hour 50 minutes. Following the heat treatment, the plates were placed immediately back into the Conviron® growth chamber. On the 7th, 9th, and 11th day at 22° C. after the heat treatment, the plates were scanned using Epson Perfection 4870 scanner. The area of each seedling (green area) was quantified using the Win-Rhizo software (Regent Instruments). The transgenic status of each plant was assessed by Finale™ resistance.

The seedling area (a measure of growth after heat treatment) of transgenic plants was compared to that of the pooled controls comprising non-transgenic segregants and wild-type Ws controls grown on the same plate. Significance of heat tolerance was assessed using a one-tailed Student's t-test, assuming unequal variance, at $p \leq 0.5$.

Heat Shock II Assay

Seeds were plated on heat germination agar plates containing 45 mL of half-strength MS medium (2.15 g MS salt (PhytoTechnology Laboratories®), 5 g sucrose (Sigma-Aldrich®), and 0.7% agar (PhytoTechnology Laboratories®) per liter, pH 5.7) per Petri dish (square, 100 mm×15 mm) One transgenic event (30 seeds), 4 wild-type Ws control seeds, and 2 seeds of a transgenic positive control were plated on each plate. Plates were wrapped with vent tape and placed in the dark at 4° C. for 3 days. Plates were then transferred into a Conviron® growth chamber set at 22° C., 16:8 hour light:dark cycle, and 70% humidity with fluorescent lamps emitting a light intensity of about 60 µE.

After the plants were grown in the Conviron® growth chamber for 11 days, the plates were scanned using a CF imager (Technologica) to record the PSII operating efficiency ($\Delta\Phi_{PSII}$) and seedling area. The plates were then transferred to a Conviron® reach-in heat chamber set at 42° C. for 5 hours. Following the heat treatment, the plants were immediately scanned using the CF imager, and then transferred back into the Conviron® growth chamber. After 2 and 4 days of recovery in the growth chamber, the plates were scanned using the CF imager again. The transgenic status of each plant was assessed by Finale™ resistance.

The differences in the PSII operating efficiency and seedling size prior to heat shock, immediately after heat shock, and after recovery following heat shock were calculated. The differences in the PSII operating efficiency and seedling size of transgenic plants were compared to the pooled controls comprising non-transgenic segregants and wild-type Ws controls grown on the same plate. Significance of heat tolerance was assessed using a one-tailed Student's t-test, assuming unequal variance, at p≤0.5.

Example 4—Results for ME00029 Events $T_2$ and $T_3$ seed from two events of ME00029 containing SEQ ID NO:441 under control of a p32449 promoter was analyzed for rosette area, terminal plant height, and seed yield as described in Example 2. The results are provided in Table 1.

TABLE 1

Chronic drought response of seedlings from ME00029

| Plants | Measurement | Control Population | |
|---|---|---|---|
| | | Internal | Pooled |
| $T_2$ seedlings from event-01 of ME00029 | Rosette Area | N.S. | Sig. |
| $T_2$ seedlings from event-04 of ME00029 | Rosette Area | N.A. | Sig. |
| $T_2$ seedlings from event-01 of ME00029 | Longest Leaf | N.S. | Sig. |
| $T_2$ seedlings from event-01 of ME00029 | Terminal Plant Height | Sig. | Sig. |
| $T_3$ seedlings from event-01 of ME00029 | Terminal Plant Height | Sig. | Sig. |
| $T_2$ seedlings from event-04 of ME00029 | Terminal Plant Height | N.A. | Sig. |
| $T_3$ seedlings from event-04 of ME00029 | Terminal Plant Height | N.A. | Sig. |
| $T_3$ seedlings from event-01 of ME00029 | Seed Yield | N.S. | Sig. |

N.A.—results not available due to insufficient sample size (n < 5);
N.S.—not significant;
Sig.—significant (p ≤ 0.5).

Example 5—Results for ME00045 Events $T_2$ and $T_3$ seed from three events of ME00045 containing SEQ ID NO:488 under control of a p32449 promoter was analyzed for rosette area, terminal plant height, longest leaf length, and seed yield as described in Example 2. The results are provided in Table 2.

TABLE 2

Chronic drought response of seedlings from ME00045

| Plants | Measurement | Control Population | | |
|---|---|---|---|---|
| | | Internal | Pooled | Ws |
| $T_3$ seedlings from event-02 of ME00045 | Rosette Area | N.S. | N.S. | Sig. |
| $T_3$ seedlings from event-02 of ME00045 | Rosette Area | N.S. | N.S. | N.S. |
| $T_2$ seedlings from event-07 of ME00045 | Rosette Area | N.A. | N.S. | Sig. |
| $T_2$ seedlings from event-07 of ME00045 | Rosette Area | N.S. | N.S. | Sig. |
| $T_2$ seedlings from event-08 of ME00045 | Rosette Area | N.A. | N.S. | Sig. |
| $T_2$ seedlings from event-08 of ME00045 | Rosette Area | N.S. | N.S. | N.S. |
| $T_3$ seedlings from event-02 of ME00045 | Longest Leaf | Sig. | Sig. | Sig. |
| $T_3$ seedlings from event-02 of ME00045 | Longest Leaf | N.S. | N.S. | N.S. |
| $T_2$ seedlings from event-07 of ME00045 | Longest Leaf | N.A. | N.S. | Sig. |
| $T_2$ seedlings from event-07 of ME00045 | Longest Leaf | N.S. | N.S. | N.S. |
| $T_2$ seedlings from event-08 of ME00045 | Longest Leaf | N.A. | N.S. | Sig. |
| $T_2$ seedlings from event-08 of ME00045 | Longest Leaf | N.S. | N.S. | N.S. |
| $T_3$ seedlings from event-02 of ME00045 | Terminal Plant Height | N.S. | N.S. | N.S. |
| $T_3$ seedlings from event-02 of ME00045 | Terminal Plant Height | N.S. | N.S. | N.S.* |
| $T_2$ seedlings from event-07 of ME00045 | Terminal Plant Height | N.A. | Sig. | Sig. |
| $T_2$ seedlings from event-07 of ME00045 | Terminal Plant Height | N.S. | Sig. | Sig. |
| $T_2$ seedlings from event-08 of ME00045 | Terminal Plant Height | N.A. | N.S.* | N.S. |
| $T_2$ seedlings from event-08 of ME00045 | Terminal Plant Height | N.S. | N.S. | Sig. |
| $T_3$ seedlings from event-02 of ME00045 | Seed Yield | Sig. | N.S.* | Sig. |
| $T_3$ seedlings from event-02 of ME00045 | Seed Yield | N.S. | N.S. | N.S. |
| $T_2$ seedlings from event-07 of ME00045 | Seed Yield | N.A. | N.S. | N.S. |
| $T_2$ seedlings from event-07 of ME00045 | Seed Yield | N.S. | N.S. | N.S. |
| $T_2$ seedlings from event-08 of ME00045 | Seed Yield | N.A. | N.S.* | Sig. |
| $T_2$ seedlings from event-08 of ME00045 | Seed Yield | N.S. | N.S. | Sig. |

N.A.—results not available due to insufficient sample size;
N.S.—not significant (p > 0.10);
N.S.*—not significant (0.5 < p < 0.10);
Sig.—significant (p < 0.5).
Data in bold represents a second independent replicate.

Example 6—Results for ME02190 Events $T_2$ and $T_4$ seed from two events of ME02190 containing SEQ ID NO:567 under control of a 35S promoter was analyzed for rosette area, terminal plant height, and longest leaf length as described in Example 2. The results are provided in Table 3.

TABLE 3

Chronic drought response of seedlings from ME02190

| Plants | Measurement | Control Population | |
|---|---|---|---|
| | | Internal | Pooled |
| $T_2$ seedlings from event-10 of ME02190 | Rosette Area | N.S. | Sig. |
| $T_4$ seedlings from event-02 of ME02190 | Longest Leaf | N.A. | Sig. |
| $T_2$ seedlings from event-10 of ME02190 | Longest Leaf | N.S. | Sig. |

TABLE 3-continued

Chronic drought response of seedlings from ME02190

| Plants | Measurement | Control Population | |
|---|---|---|---|
| | | Internal | Pooled |
| $T_4$ seedlings from event-02 of ME02190 | Terminal Plant Height | N.A. | Sig. |
| $T_2$ seedlings from event-10 of ME02190 | Terminal Plant Height | N.S. | Sig. |

N.A.—results not available due to insufficient sample size (n < 5);
N.S.—not significant;
Sig.—significant (p ≤ 0.5).

Example 7—Results for ME02549 Events $T_2$ and $T_3$ seed from three events of ME02549 containing SEQ ID NO:589 under control of a 35S promoter was analyzed for rosette area, terminal plant height, and longest leaf length as described in Example 2. The results are provided in Table 4.

TABLE 4

Chronic drought response of seedlings from ME02549

| Plants | Measurement | Control Population | | |
|---|---|---|---|---|
| | | Internal | Pooled | Ws |
| $T_2$ seedlings from event-01 of ME02549 | Rosette Area | Sig. | N.S. | Sig. |
| $T_3$ seedlings from event-01 of ME02549 | Rosette Area | Sig. | N.S. | N.S. |
| $T_2$ seedlings from event-02 of ME02549 | Rosette Area | N.S.* | N.S.* | Sig. |
| $T_3$ seedlings from event-02 of ME02549 | Rosette Area | N.S. | N.S. | Sig. |
| $T_2$ seedlings from event-05 of ME02549 | Rosette Area | N.A. | N.S. | Sig. |
| $T_3$ seedlings from event-05 of ME02549 | Rosette Area | N.S. | N.S.* | Sig. |
| $T_3$ seedlings from event-01 of ME02549 | Longest Leaf | N.S. | N.S. | Sig. |
| $T_3$ seedlings from event-02 of ME02549 | Longest Leaf | N.S. | N.S. | Sig. |
| $T_3$ seedlings from event-05 of ME02549 | Longest Leaf | N.S. | N.S. | Sig. |
| $T_2$ seedlings from event-01 of ME02549 | Terminal Plant Height | N.A. | N.S. | N.S. |
| $T_3$ seedlings from event-01 of ME02549 | Terminal Plant Height | N.S. | N.S. | Sig. |
| $T_3$ seedlings from event-02 of ME02549 | Terminal Plant Height | N.S. | Sig. | Sig. |
| $T_2$ seedlings from event-05 of ME02549 | Terminal Plant Height | N.A. | N.S. | N.S. |
| $T_3$ seedlings from event-05 of ME02549 | Terminal Plant Height | Sig. | N.S. | Sig. |

N.A.—results not available due to insufficient sample size (n < 5);
N.S.—not significant;
N.S.*—not significant (0.5 < p < 0.10);
Sig.—significant (p < 0.5).

Example 8—Results for ME02865 Events $T_2$ and $T_3$ seed from two events of ME02865 containing SEQ ID NO:704 under control of a 35S promoter was analyzed for rosette area, terminal plant height, longest leaf length, and seed weight as described in Example 2. The results are provided in Table 5.

TABLE 5

Chronic drought response of seedlings from ME02865

| Plants | Measurement | Control Population | |
|---|---|---|---|
| | | Internal | Pooled |
| $T_2$ seedlings from event-02 of ME02865 | Rosette Area | N.S. | N.S. |
| $T_3$ seedlings from event-02-01 of ME02865 | Rosette Area | — | N.S. |
| $T_3$ seedlings from event-02-02 of ME02865 | Rosette Area | N.S. | N.S. |
| $T_2$ seedlings from event-05 of ME02865 | Rosette Area | —. | Sig. |
| $T_3$ seedlings from event-05-01 of ME02865 | Rosette Area | — | Sig. |
| $T_3$ seedlings from event-05-02 of ME02865 | Rosette Area | N.S. | N.S. |
| $T_2$ seedlings from event-02 of ME02865 | Longest Leaf | N.S. | N.S. |
| $T_3$ seedlings from event-02-01 of ME02865 | Longest Leaf | — | N.S. |
| $T_3$ seedlings from event-02-02 of ME02865 | Longest Leaf | N.S.* | Sig. |
| $T_2$ seedlings from event-05 of ME02865 | Longest Leaf | — | Sig. |
| $T_3$ seedlings from event-05-01 of ME02865 | Longest Leaf | — | N.S. |
| $T_3$ seedlings from event-05-02 of ME02865 | Longest Leaf | N.S. | Sig. |
| $T_2$ seedlings from event-02 of ME02865 | Terminal Plant Height | Sig. | Sig. |
| $T_3$ seedlings from event-02-01 of ME02865 | Terminal Plant Height | — | N.S.* |
| $T_3$ seedlings from event-02-02 of ME02865 | Terminal Plant Height | N.S. | Sig. |
| $T_2$ seedlings from event-05 of ME02865 | Terminal Plant Height | — | Sig. |
| $T_3$ seedlings from event-05-01 of ME02865 | Terminal Plant Height | — | N.S.* |
| $T_3$ seedlings from event-05-02 of ME02865 | Terminal Plant Height | N.S.* | Sig. |
| $T_2$ seedlings from event-02 of ME02865 | Seed Weight | N.S. | N.S. |
| $T_3$ seedlings from event-02-01 of ME02865 | Seed Weight | — | N.S. |
| $T_3$ seedlings from event-02-02 of ME02865 | Seed Weight | Sig. | N.S. |
| $T_2$ seedlings from event-05 of ME02865 | Seed Weight | — | Sig. |
| $T_3$ seedlings from event-05-01 of ME02865 | Seed Weight | — | N.S. |
| $T_3$ seedlings from event-05-02 of ME02865 | Seed Weight | N.S. | N.S.* |

N.A.—results not available due to insufficient sample size (n < 5);
N.S.—not significant;
N.S.*—not significant (0.5 < p < 0.10);
Sig.—significant (p < 0.5).

The physical appearances of $T_1$ ME02865 plants were similar to those of corresponding control plants grown under standard conditions. There were no observable or statistically significant differences between $T_2$ plants from events −02 and −05 of ME02865 and control plants in germination, onset of flowering, rosette area, fertility, and general morphology/architecture when grown under standard conditions.

Example 9—Results for ME03227 Events $T_2$ and $T_3$ seed from two events of ME03227 containing SEQ ID NO:710 under control of a 35S promoter was analyzed for rosette area, terminal plant height, and longest leaf length as described in Example 2. The results are provided in Table 6.

TABLE 6

Chronic drought response of seedlings from ME03227

| Plants | Measurement | Control Population Internal | Control Population Pooled |
|---|---|---|---|
| $T_2$ seedlings from event-01 of ME03227 | Rosette Area | N.A. | Sig. |
| $T_3$ seedlings from event-01 of ME03227 | Rosette Area | N.A. | Sig. |
| $T_2$ seedlings from event-05 of ME03227 | Rosette Area | N.A. | Sig. |
| $T_3$ seedlings from event-05 of ME03227 | Rosette Area | N.A. | Sig. |
| $T_3$ seedlings from event-05 of ME03227 | Longest Leaf | N.A. | Sig. |
| $T_3$ seedlings from event-01 of ME03227 | Terminal Plant Height | N.A. | N.S.* |
| $T_3$ seedlings from event-05 of ME03227 | Terminal Plant Height | N.A. | N.S.* |

N.A.—results not available due to insufficient sample size (n < 5);
N.S.—not significant;
N.S.*—not significant (0.5 < p < 0.10);
Sig.—significant (p ≤ 0.5).

Example 10—Results for ME04477 Events $T_2$ seed from five events of ME04477 containing SEQ ID NO:1241 under control of a 35S promoter was analyzed for rosette area, terminal plant height, and longest leaf length as described in Example 2. The results are provided in Table 7.

TABLE 7

Chronic drought response of seedlings from ME04477

| Plants | Measurement | Control Population Internal | Control Population Pooled |
|---|---|---|---|
| $T_2$ seedlings from event-03 of ME04477 | Rosette Area | N.A. | Sig. |
| $T_2$ seedlings from event-01 of ME04477 | Longest Leaf | N.A. | Sig. |
| $T_2$ seedlings from event-02 of ME04477 | Longest Leaf | N.A. | Sig. |
| $T_2$ seedlings from event-03 of ME04477 | Longest Leaf | N.A. | Sig. |
| $T_2$ seedlings from event-04 of ME04477 | Longest Leaf | Sig. | Sig. |
| $T_2$ seedlings from event-05 of ME04477 | Longest Leaf | N.A. | Sig. |
| $T_2$ seedlings from event-01 of ME04477 | Terminal Plant Height | N.A. | Sig. |
| $T_2$ seedlings from event-02 of ME04477 | Terminal Plant Height | N.A. | Sig. |
| $T_2$ seedlings from event-03 of ME04477 | Terminal Plant Height | N.A. | Sig. |
| $T_2$ seedlings from event-04 of ME04477 | Terminal Plant Height | Sig. | Sig. |
| $T_2$ seedlings from event-05 of ME04477 | Terminal Plant Height | N.A. | Sig. |

N.A.—results not available due to insufficient sample size (n < 5);
N.S.—not significant;
Sig.—significant (p < 0.5).

Example 11—Results for ME18396 Events $T_2$ seed from one event of ME18396 containing SEQ ID NO:1260 under control of a p326 promoter was analyzed for rosette area and terminal plant height as described in Example 2. The results are provided in Table 8.

TABLE 8

Chronic drought response of seedlings from ME18396

| Plants | Measurement | Control Population Internal | Control Population Pooled |
|---|---|---|---|
| $T_2$ seedlings from event-02 of ME18396 | Rosette Area | N.S. | Sig. |
| $T_2$ seedlings from event-02 of ME18396 | Terminal Plant Height | Sig. | Sig. |

N.S.—not significant;
Sig.—significant (p < 0.5).

Example 12—Results for ME20095 Events $T_2$ and $T_3$ seed from two events of ME20095 containing SEQ ID NO:1128 under control of a 35S promoter was analyzed for rosette area, longest leaf length, terminal plant height, and seed yield as described in Example 2. The results are provided in Table 9.

TABLE 9

Chronic drought response of seedlings from ME20095

| Plants | Measurement | Control Population Internal | Control Population Pooled |
|---|---|---|---|
| $T_2$ seedlings from event-01 of ME20095 | Rosette Area | Sig. | Sig. |
| $T_3$ seedlings from event-01-01 of ME20095 | Rosette Area | N.S. | N.S. |
| $T_3$ seedlings from event-01-02 of ME20095 | Rosette Area | N.S. | N.S. |
| $T_2$ seedlings from event-04 of ME20095 | Rosette Area | Sig. | Sig. |
| $T_3$ seedlings from event-04-01 of ME20095 | Rosette Area | N.S. | N.S. |
| $T_3$ seedlings from event-04-02 of ME20095 | Rosette Area | N.S. | N.S.* |
| $T_2$ seedlings from event-01 of ME20095 | Longest Leaf | N.S. | Sig. |
| $T_3$ seedlings from event-01-01 of ME20095 | Longest Leaf | Sig. | Sig. |
| $T_3$ seedlings from event-01-02 of ME20095 | Longest Leaf | N.S. | N.S. |
| $T_2$ seedlings from event-04 of ME20095 | Longest Leaf | Sig. | Sig. |
| $T_3$ seedlings from event-04-01 of ME20095 | Longest Leaf | Sig. | Sig. |
| $T_3$ seedlings from event-04-02 of ME20095 | Longest Leaf | N.S.* | Sig. |
| $T_2$ seedlings from event-01 of ME20095 | Terminal Plant Height | N.S. | Sig. |
| $T_3$ seedlings from event-01-01 of ME20095 | Terminal Plant Height | N.S.* | Sig. |
| $T_3$ seedlings from event-01-02 of ME20095 | Terminal Plant Height | N.S. | N.S.* |
| $T_2$ seedlings from event-04 of ME20095 | Terminal Plant Height | Sig. | Sig. |
| $T_3$ seedlings from event-04-01 of ME20095 | Terminal Plant Height | Sig. | Sig. |
| $T_3$ seedlings from event-04-02 of ME20095 | Terminal Plant Height | N.S. | Sig. |
| $T_2$ seedlings from event-01 of ME20095 | Seed Weight | Sig. | Sig. |
| $T_3$ seedlings from event-01-01 of ME20095 | Seed Weight | Sig. | N.S.* |
| $T_3$ seedlings from event-01-02 of ME20095 | Seed Weight | Sig. | Sig. |
| $T_2$ seedlings from event-04 of ME20095 | Seed Weight | N.S. | N.S. |

TABLE 9-continued

Chronic drought response of seedlings from ME20095

| Plants | Measurement | Control Population | |
|---|---|---|---|
| | | Internal | Pooled |
| $T_3$ seedlings from event-04-01 of ME20095 | Seed Weight | N.S. | N.S. |
| $T_3$ seedlings from event-04-02 of ME20095 | Seed Weight | N.S. | N.S. |

N.S.—not significant;
N.S.*—not significant (0.5 < p < 0.10);
Sig.—significant (p < 0.5).

$T_1$ ME20095 plants showed delayed flowering and prolonged vegetative growth compared to corresponding control plants grown under standard conditions. There were no observable or statistically significant differences between $T_2$ plants from events −02 and −04 of ME20095 and control plants in germination, onset of flowering, fertility, and general morphology/architecture when grown under standard conditions. Rosette area in T2 plants from events −02 and −04 was significantly larger and seed yield was increased as compared to corresponding control plants grown under standard conditions.

Example 13—Results for ME02401 Events

T2 and T3 seed from two events of ME02401 containing SEQ ID NO:749 under control of a 35S promoter was analyzed for rosette area, terminal plant height, and longest leaf length as described in Example 2. The results are provided in Table 10.

TABLE 10

Chronic drought response of seedlings from ME02401

| Plants | Measurement | Control Population | |
|---|---|---|---|
| | | Internal | Pooled |
| $T_2$ seedlings from event-05 of ME02401 | Rosette Area | N.A. | N.S.* |
| $T_3$ seedlings from event-01 of ME02401 | Longest Leaf | N.S.* | Sig. |
| $T_2$ seedlings from event-05 of ME02401 | Longest Leaf | N.A. | Sig. |
| $T_3$ seedlings from event-01 of ME02401 | Terminal Plant Height | Sig. | Sig. |
| $T_2$ seedlings from event-05 of ME02401 | Terminal Plant Height | N.A. | Sig. |

N.A.—results not available due to insufficient sample size (n < 5);
N.S.—not significant;
N.S.*—not significant (0.5 < p < 0.10);
Sig.—significant (p < 0.5).

Example 14—Results for ME02932 Events $T_2$ and $T_3$ seed from two events of ME02932 containing SEQ ID NO:59 under control of a 35S promoter was analyzed for seedling area following a Heat Shock I assay as described in Example 3. The results are provided in Table 11.

TABLE 11

ME02932 seedling area following Heat Shock I assay

| Plants | Average seedling area | SE | N | p-value |
|---|---|---|---|---|
| $T_2$ seedlings from event-01 of ME02932 | 0.07 | 0.008 | 33 | 8.77E−04 |
| $T_2$ non-transgenic segregants of event-01 of ME02932 | 0.04 | 0.006 | 15 | |
| $T_3$ seedlings from event-01 of ME02932 | 0.10 | 0.003 | 40 | 2.21E−04 |
| $T_3$ non-transgenic segregants of event-01 of ME02932 | 0.07 | 0.007 | 9 | |
| $T_2$ seedlings from event-03 of ME02932 | 0.08 | 0.012 | 21 | 1.29E−02 |
| $T_2$ non-transgenic segregants of event-03 of ME02932 | 0.04 | 0.009 | 23 | |
| $T_3$ seedlings from event-03 of ME02932 | 0.09 | 0.004 | 36 | 1.54E−03 |
| $T_3$ non-transgenic segregants of event-03 of ME02932 | 0.07 | 0.005 | 13 | |

The physical appearances of $T_1$ ME02932 plants were similar to those of corresponding control plants grown under standard conditions. There were no observable or statistically significant differences between $T_2$ plants from events −01 and −03 of ME02932 and control plants in germination, onset of flowering, rosette area, fertility, and general morphology/architecture when grown under standard conditions.

Example 15—Results for ME18240 Events $T_2$ and $T_3$ seed from three events of ME18240 containing SEQ ID NO:363 under control of a 35S promoter was analyzed for seedling area following a Heat Shock I assay and change in photosynthetic activity during a Heat Shock II assay as described in Example 3. The results are provided in Tables 12 and 13.

TABLE 12

ME18240 seedling area following Heat Shock I assay

| Plants | Average seedling area | SE | N | p-value |
|---|---|---|---|---|
| $T_2$ seedlings from event-02 of ME18240 | 0.08 | 0.007 | 27 | 4.22E−08 |
| $T_2$ non-transgenic segregants of event-02 of ME18240 | 0.03 | 0.004 | 16 | |
| $T_3$ seedlings from event-02 of ME18240 | 0.14 | 0.007 | 31 | 5.83E−11 |
| $T_3$ non-transgenic segregants of event-02 of ME18240 | 0.06 | 0.007 | 14 | |
| $T_2$ seedlings from event-03 of ME18240 | 0.13 | 0.007 | 35 | 3.31E−05 |
| $T_2$ non-transgenic segregants of event-03 of ME18240 | 0.08 | 0.01 | 14 | |
| $T_3$ seedlings from event-03 of ME18240 | 0.14 | 0.008 | 28 | 5.13E−06 |
| $T_3$ non-transgenic segregants of event-03 o fME18240 | 0.09 | 0.008 | 19 | |
| $T_2$ seedlings from event-04 of ME18240 | 0.13 | 0.008 | 33 | 2.39E−07 |
| $T_2$ non-transgenic segregants of event-04 of ME18240 | 0.06 | 0.009 | 16 | |
| $T_3$ seedlings from event-04 of ME18240 | 0.13 | 0.008 | 29 | 4.68E−05 |
| $T_3$ non-transgenic segregants of event-04 of ME18240 | 0.08 | 0.008 | 18 | |

TABLE 13

ME18240 ΔFv/Fm in response to Heat Shock II assay

| Plants | Average ΔFv/Fm | SE | N | p-value |
|---|---|---|---|---|
| $T_2$ seedlings from event-02 of ME18240 | 0.24 | 0.013 | 47 | 3.64E−05 |
| $T_2$ non-transgenic segregants of event-02 of ME18240 | 0.32 | 0.016 | 25 | |
| $T_3$ seedlings from event-02 of ME18240 | 0.36 | 0.012 | 43 | 1.92E−04 |
| $T_3$ non-transgenic segregants of event-02 of ME18240 | 0.43 | 0.016 | 22 | |
| $T_2$ seedlings from event-03 of ME18240 | 0.24 | 0.010 | 41 | 9.27E−11 |
| $T_2$ non-transgenic segregants of event-03 of ME18240 | 0.37 | 0.011 | 28 | |
| $T_3$ seedlings from event-03 of ME18240 | 0.33 | 0.011 | 24 | 1.91E−02 |
| $T_3$ non-transgenic segregants of event-03 of ME18240 | 0.39 | 0.022 | 10 | |
| $T_2$ seedlings from event-04 of ME18240 | 0.21 | 0.009 | 43 | 5.55E−17 |
| $T_2$ non-transgenic segregants of event-04 of ME18240 | 0.40 | 0.007 | 29 | |
| $T_3$ seedlings from event-04 of ME18240 | 0.28 | 0.011 | 46 | 9.38E−11 |
| $T_3$ non-transgenic segregants of event-04 of ME18240 | 0.41 | 0.008 | 21 | |

Where ΔFv/Fm = Fv/Fm prior to heat shock − Fv/Fm after heat shock.

The physical appearances of $T_1$ ME18240 plants were similar to those of corresponding control plants grown under standard conditions. There were no observable or statistically significant differences between $T_2$ plants from events −02, −03, and −04 of ME18240 and control plants in germination, onset of flowering, rosette area, fertility, and general morphology/architecture when grown under standard conditions.

Example 16—Results for ME20867 Events $T_2$ and $T_3$ seed from four events of ME20867 containing SEQ ID NO:310 under control of a 35S promoter was analyzed for seedling area following a Heat Shock I assay and change in photosynthetic activity during a Heat Shock II assay as described in Example 3. The results are provided in Tables 14 and 15.

TABLE 14

ME20867 seedling area in response to Heat Shock I assay

| Plants | Average seedling area | SE | N | p-value |
|---|---|---|---|---|
| $T_2$ seedlings from event-01 of ME20867 | 0.14 | 0.008 | 28 | 4.86E−07 |
| $T_2$ non-transgenic segregants of event-01 of ME20867 | 0.07 | 0.011 | 12 | |
| $T_3$ seedlings from event-01 of ME20867 | 0.07 | 0.007 | 31 | 9.84E−10 |
| $T_3$ non-transgenic segregants of event-01 of ME20867 | 0.01 | 0.010 | 16 | |
| $T_2$ seedlings from event-02 of ME20867 | 0.13 | 0.006 | 37 | 1.03E−02 |
| $T_2$ non-transgenic segregants of event-02 of ME20867 | 0.08 | 0.024 | 3 | |
| $T_3$ seedlings from event-02 of ME20867 | 0.09 | 0.006 | 32 | 6.01E−07 |
| $T_3$ non-transgenic segregants of event-02 of ME20867 | 0.02 | 0.011 | 9 | |
| $T_2$ seedlings from event-04 of ME20867 | 0.12 | 0.006 | 31 | 1.47E−02 |
| $T_2$ non-transgenic segregants of event-04 of ME20867 | 0.10 | 0.010 | 9 | |
| $T_3$ seedlings from event-04 of ME20867 | 0.03 | 0.005 | 20 | 2.14E−04 |
| $T_3$ non-transgenic segregants of event-04 of ME20867 | 0.01 | 0.007 | 12 | |
| $T_2$ seedlings from event-05 of ME20867 | 0.11 | 0.009 | 30 | 1.51E−02 |
| $T_2$ non-transgenic segregants of event-05 of ME20867 | 0.08 | 0.012 | 10 | |
| $T_3$ seedlings from event-05 of ME20867 | 0.03 | 0.004 | 23 | 1.98E−04 |
| $T_3$ non-transgenic segregants of event-05 of ME20867 | 0.01 | 0.005 | 20 | |

TABLE 15

ME20867 ΔFv/Fm − $D_2$ in response to Heat Shock II assay

| Plants | Average ΔFv/Fm − $D_2$ | SE | N | p-value |
|---|---|---|---|---|
| $T_2$ seedlings from event-01 of ME20867 | 0.03 | 0.012 | 33 | 2.17E−08 |
| $T_2$ non-transgenic segregants of event-01 of ME20867 | −0.07 | 0.008 | 12 | |
| $T_3$ seedlings from event-01 of ME20867 | 0.21 | 0.010 | 44 | 3.71E−12 |
| $T_3$ non-transgenic segregants of event-01 of ME20867 | 0.06 | 0.015 | 22 | |
| $T_2$ seedlings from event-02 of ME20867 | 0.06 | 0.011 | 25 | 9.39E−11 |
| $T_2$ non-transgenic segregants of event-02 of ME20867 | −0.10 | 0.006 | 12 | |
| $T_3$ seedlings from event-02 of ME20867 | 0.25 | 0.012 | 50 | 4.79E−08 |
| $T_3$ non-transgenic segregants of event-02 of ME20867 | 0.06 | 0.029 | 16 | |
| $T_2$ seedlings from event-04 of ME20867 | 0.17 | 0.010 | 43 | 8.71E−11 |
| $T_2$ non-transgenic segregants of event-04 of ME20867 | 0.03 | 0.014 | 22 | |
| $T_3$ seedlings from event-04 of ME20867 | 0.16 | 0.011 | 24 | 1.39E−03 |
| $T_3$ non-transgenic segregants of event-04 of ME20867 | 0.06 | 0.027 | 9 | |
| $T_2$ seedlings from event-05 of ME20867 | 0.21 | 0.016 | 28 | 1.35E−09 |
| $T_2$ non-transgenic segregants of event-05 of ME20867 | 0.07 | 0.012 | 31 | |
| $T_3$ seedlings from event-05 of ME20867 | 0.24 | 0.015 | 19 | 3.72E−03 |
| $T_3$ non-transgenic segregants of event-05 of ME20867 | 0.18 | 0.015 | 14 | |

ΔFv/Fm − $D_2$ = Fv/Fm immediately after heat shock − Fv/Fm after 2 days recovery.

The physical appearances of $T_1$ ME20867 plants were similar to those of corresponding control plants grown under standard conditions. There were no observable or statistically significant differences between $T_2$ plants from events −01, −02, −04 and −05 of ME20867 and control plants in germination, onset of flowering, rosette area, fertility, and general morphology/architecture when grown under standard conditions.

Example 17—Results for ME03268 Events $T_2$ and $T_3$ seed from one event of ME03268, and $T_3$ and $T_4$ seed from one event of ME03268, each containing SEQ ID NO:159 under control of a 35S promoter, was analyzed for seedling area following a Heat Shock I assay as described in Example 3. The results are provided in Table 16.

TABLE 16

ME03268 seedling area in response to Heat Shock I assay

| Plants | Average seedling area | SE | N | p-value |
|---|---|---|---|---|
| $T_2$ seedlings from event-02 of ME03268 | 0.165 | 0.015 | 26 | 1.09E−03 |
| $T_2$ non-transgenic segregants of event-02 of ME03268 | 0.070 | 0.024 | 3 | |

TABLE 16-continued

ME03268 seedling area in response to Heat Shock I assay

| Plants | Average seedling area | SE | N | p-value |
|---|---|---|---|---|
| $T_3$ seedlings from event-02 of ME03268 | 0.137 | 0.009 | 40 | 1.97E−07 |
| $T_3$ non-transgenic segregants of event-02 of ME03268 | 0.048 | 0.012 | 9 | |
| $T_3$ seedlings from event-03 of ME03268 | 0.062 | 0.007 | 26 | 3.65E−02 |
| $T_3$ non-transgenic segregants of event-03 of ME03268 | 0.037 | 0.011 | 4 | |
| $T_4$ seedlings from event-03 of ME03268 | 0.094 | 0.008 | 30 | 3.96E−03 |
| $T_4$ non-transgenic segregants of event-03 of ME03268 | 0.054 | 0.012 | 10 | |

The physical appearances of $T_1$ ME03268 plants were similar to those of corresponding control plants grown under standard conditions. There were no observable or statistically significant differences between $T_2$ plants from events −02 and −03 of ME03268 and control plants in germination, onset of flowering, rosette area, fertility, and general morphology/architecture when grown under standard conditions.

Example 18—Results for ME06551 Events $T_3$ and $T_4$ seed from two events of ME06551 containing SEQ ID NO:1 under control of a 35S promoter was analyzed for change in photosynthetic activity during a Heat Shock II assay as described in Example 3. The results are provided in Table 17.

TABLE 17

ME06551 ΔFv/Fm in response to Heat Shock II assay

| Plants | Average ΔFv/Fm | SE | N | p-value |
|---|---|---|---|---|
| $T_3$ seedlings from event-04 of ME06551 | 0.42 | 0.016 | 11 | 1.32E−02 |
| $T_3$ non-transgenic segregants of event-04 of ME06551 | 0.47 | 0.012 | 15 | |
| $T_4$ seedlings from event-04 of ME06551 | 0.39 | 0.006 | 49 | 4.73E−03 |
| $T_4$ non-transgenic segregants of event-04 of ME06551 | 0.43 | 0.014 | 11 | |
| $T_3$ seedlings from event-05 of ME06551 | 0.39 | 0.013 | 11 | 4.21E−04 |
| $T_3$ non-transgenic segregants of event-05 of ME06551 | 0.46 | 0.010 | 13 | |
| $T_4$ seedlings from event-05 of ME06551 | 0.39 | 0.007 | 50 | 4.79E−02 |
| $T_4$ non-transgenic segregants of event-05 of ME06551 | 0.41 | 0.010 | 17 | |

Where ΔFv/Fm = Fv/Fm prior to heat shock − Fv/Fm after heat shock.

The physical appearances of $T_1$ ME06551 plants were similar to those of corresponding control plants grown under standard conditions. There were no observable or statistically significant differences between $T_2$ plants from events −04 and −05 of ME06551 and control plants in germination, onset of flowering, rosette area, fertility, and general morphology/architecture when grown under standard conditions.

Example 19—Results for ME06919 Events $T_2$ and $T_3$ seed from two events of ME06919 containing SEQ ID NO:56 under control of a 35S promoter was analyzed for change in photosynthetic activity during a Heat Shock II assay as described in Example 3. The results are provided in Table 18.

TABLE 18

ME06919 ΔFv/Fm in response to Heat Shock II assay

| Plants | Average ΔFv/Fm | SE | N | p-value |
|---|---|---|---|---|
| $T_2$ seedlings from event-03 of ME06919 | 0.433 | 0.007 | 65 | 2.55E−09 |
| $T_2$ non-transgenic segregants of event-03 of ME06919 | 0.497 | 0.008 | 37 | |
| $T_3$ seedlings from event-03 of ME06919 | 0.281 | 0.013 | 46 | 1.87E−03 |
| $T_3$ non-transgenic segregants of event-03 of ME06919 | 0.341 | 0.015 | 18 | |
| $T_2$ seedlings from event-04 of ME06919 | 0.490 | 0.007 | 21 | 3.06E−04 |
| $T_2$ non-transgenic segregants of event-04 of ME06919 | 0.531 | 0.009 | 26 | |
| $T_3$ seedlings from event-04 of ME06919 | 0.296 | 0.006 | 44 | 6.15E−08 |
| $T_3$ non-transgenic segregants of event-04 of ME06919 | 0.412 | 0.018 | 18 | |

Where ΔFv/Fm = Fv/Fm prior to heat shock − Fv/Fm after heat shock.

The physical appearances of $T_1$ ME06919 plants were similar to those of corresponding control plants grown under standard conditions. There were no observable or statistically significant differences between $T_2$ plants from events −03 and −04 of ME06919 and control plants in germination, onset of flowering, rosette area, fertility, and general morphology/architecture when grown under standard conditions.

Example 20—Results for ME04246 Events $T_2$ and $T_3$ seed from two events of ME04246 containing SEQ ID NO:1362 under control of a 35S promoter was analyzed for rosette area, terminal plant height, and longest leaf length as described in Example 2. The results are provided in Table 19.

TABLE 19

Chronic drought response of seedlings from ME04246

| | | Control Population | | |
|---|---|---|---|---|
| Plants | Measurement | Internal | Pooled | Ws |
| $T_2$ seedlings from event-01 of ME04246 | Longest Leaf | Sig. | Sig. | N.S. |
| $T_2$ seedlings from event-03 of ME04246 | Longest Leaf | N.S. | N.S. | N.S. |
| $T_2$ seedlings from event-04 of ME04246 | Longest Leaf | N.S. | N.S. | N.S. |
| $T_2$ seedlings from event-01 of ME04246 | Dry Biomass | N.A. | N.S.* | Sig. |
| $T_2$ seedlings from event-02 of ME04246 | Dry Biomass | N.A. | N.A. | N.S. |
| $T_2$ seedlings from event-04 of ME04246 | Dry Biomass | N.A. | N.S.* | Sig. |

N.A.—results not available due to insufficient sample size (n < 5);
N.S.—not significant;
N.S.*—not significant (0.5 < p < 0.10);
Sig.—significant (p < 0.5).

$T_2$ ME04246 plants showed increased vegetative biomass compared to corresponding control plants under water-limiting conditions as measured directly and to a lesser degree by longest leaf length. There were no observable or statistically significant differences between $T_1$ plants from events −01, −03 and −04 of ME04246 and control plants in germination, onset of flowering, fertility, and general morphology/architecture when grown under standard conditions.

Example 21—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA,* 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:442, SEQ ID NO:489, SEQ ID NO:568, SEQ ID NO:590, SEQ ID NO:705, SEQ ID NO:711, SEQ ID NO:742, SEQ ID NO:1012, SEQ ID NO:1129, SEQ ID NO:60, SEQ ID NO:364, SEQ ID NO:311, SEQ ID NO:160, SEQ ID NO:2, and SEQ ID NO:749 are shown in FIGS. 1-15, respectively.

Example 22—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:442.

The procedure above was repeated and an HMM was generated for each group of sequences shown in FIGS. 2-15 using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10604766B2). An electronic copy of the "Sequence Listing" will also be available from the USPTO upon request and payment of the fee set forth in 37 CFR 1.19(b)(3).

What is claimed is:

1. A method of producing a plant, said method comprising:

growing a plant comprising an exogenous nucleic acid, said exogenous nucleic acid comprising a regulatory region operably linked to a nucleotide sequence encoding a polypeptide having 95 percent or greater sequence identity to the amino acid sequence set forth in SEQ ID NO: 749;

applying limited water conditions for at least two weeks; and selecting for a plant having increased chronic drought tolerance compared to a control plant that does not comprise said nucleic acid.

2. A method of increasing chronic drought tolerance in a plant, said method comprising:
introducing into a plant cell an exogenous nucleic acid, said exogenous nucleic acid comprising a regulatory region operably linked to a nucleotide sequence encoding a polypeptide having 95 percent or greater sequence identity to the amino acid sequence set forth in SEQ ID NO: 749;
growing the plant cell comprising the exogenous nucleic acid to generate a plant comprising the exogenous nucleic acid;
applying limited water conditions to said plant for at least two weeks;
and selecting for a plant that has an increase in chronic drought tolerance compared to a control plant that does not comprise said nucleic acid.

3. The method of claim 1, wherein said plant having increased chronic drought tolerance further exhibits increased plant growth under limited water conditions.

4. The method of claim 3, wherein said increased plant growth comprises increased plant height.

5. The method of claim 2, wherein said increased chronic drought tolerance comprises an increase in plant growth under limited water conditions.

6. The method of claim 5, wherein said increased plant growth comprises increased plant height.

7. The method of claim 1, further comprising: growing the plant having increased chronic drought tolerance and producing seed from the plant.

8. The method of claim 1, further comprising: crossing the plant having increased chronic drought tolerance with itself to produce seed comprising the exogenous nucleic acid; and growing progeny plants from said seed.

9. The method of claim 2, further comprising: crossing the plant having increased chronic drought tolerance with itself to produce seed comprising the exogenous nucleic acid; and growing progeny plants from said seed.

10. The method of claim 1, wherein said polypeptide has 97 percent or greater sequence identity to the amino acid sequence set forth in SEQ ID NO:749.

11. The method of claim 1, wherein said polypeptide comprises the amino acid sequence set forth in SEQ ID NO:749.

12. The method of claim 2, wherein said polypeptide has 97 percent or greater sequence identity to the amino acid sequence set forth in SEQ ID NO:749.

13. The method of claim 2, wherein said polypeptide comprises the amino acid sequence set forth in SEQ ID NO:749.

* * * * *